US012751915B2

(12) United States Patent
Warren et al.

(10) Patent No.: US 12,751,915 B2
(45) Date of Patent: Oct. 6, 2026

(54) METHOD AND APPARATUS FOR DELIVERING AN API-CONTAINING LIQUID TO AN EDIBLE SUBSTRATE

(71) Applicant: Transport Authority, Inc., Dover, DE (US)

(72) Inventors: William Warren, Reno, NV (US); Walter Lee Smith, Danville, CA (US); Alan Rosdon George, San Jose, CA (US); Mark Frederick Senko, Henderson, NV (US)

(73) Assignee: Transport Authority, Inc., San Leandro, CA (US)

( * ) Notice: Subject to any disclaimer, the term of this patent is extended or adjusted under 35 U.S.C. 154(b) by 0 days.

(21) Appl. No.: 19/465,307

(22) Filed: Jan. 30, 2026

(65) Prior Publication Data

US 2026/0157958 A1 Jun. 11, 2026

Related U.S. Application Data

(63) Continuation of application No. PCT/US2025/049511, filed on Oct. 3, 2025.
(Continued)

(51) Int. Cl.
*A61K 9/00* (2006.01)
*A21D 13/28* (2017.01)
(Continued)

(52) U.S. Cl.
CPC ............ *A61K 9/0056* (2013.01); *A21D 13/28* (2017.01); *A23G 3/0091* (2013.01); *A23G 3/20* (2013.01);
(Continued)

(58) Field of Classification Search
CPC .............. A61K 9/0056; A61K 31/4045; A61K 31/658; A61K 36/3482; A21D 13/28;
(Continued)

(56) References Cited

U.S. PATENT DOCUMENTS 6,811,059 B2 * 11/2004 Piucci, Jr. ............ B05B 15/557 222/145.5
2022/0023228 A1 * 1/2022 Haynes .................. A61K 47/36
(Continued)

OTHER PUBLICATIONS

Cohen et al., Quantity of Melatonin and CBD in Melatonin Gummies Sold in the US, Journal of American Medical Association (JAMA), vol. 329, 1401-1402, Apr. 2023.
(Continued)

*Primary Examiner* — Frederick C Nicolas
(74) *Attorney, Agent, or Firm* — Gray Ice Higdon

(57) ABSTRACT

Disclosed are methods and apparatus for delivering an active pharmaceutical ingredient (API) to a substrate, such as an edible. In particular, an API-containing liquid is dosed from a dosing head in small increments. Because the volume of API-containing liquid dosed in each increment is known, and the concentration of API in the API-containing liquid is known, the amount of API incrementally driven out of the dosing head in the API-containing liquid is known. Among the API driven out of the dosing head, a majority can be delivered to the substrate, for instance as individual successive droplets or as a stream. A minority can remain adhered to the dosing head as a residual API. A wash fluid can be applied to the dosing head to remove the residual API and deliver the residual API to the substrate.

30 Claims, 12 Drawing Sheets

Related U.S. Application Data

(60) Provisional application No. 63/702,759, filed on Oct. 3, 2024.

(51) Int. Cl.

| | |
|---|---|
| ***A23G 3/20*** | (2006.01) |
| ***A23G 3/34*** | (2006.01) |
| ***A23G 3/36*** | (2006.01) |
| ***A23G 3/54*** | (2006.01) |
| ***A23L 19/00*** | (2016.01) |
| ***A23L 25/00*** | (2016.01) |
| ***A23P 20/18*** | (2016.01) |
| ***A23P 20/20*** | (2016.01) |
| ***A61J 3/06*** | (2006.01) |
| ***A61K 31/00*** | (2006.01) |
| ***A61K 31/4045*** | (2006.01) |
| ***A61K 36/185*** | (2006.01) |
| ***B08B 9/023*** | (2006.01) |
| ***F04B 13/00*** | (2006.01) |
| ***G01L 19/00*** | (2006.01) |
| ***G01N 30/74*** | (2006.01) |
| *A23P 10/30* | (2016.01) |
| *A61J 3/00* | (2006.01) |
| *G01N 30/02* | (2006.01) |

(52) U.S. Cl.

CPC ............... *A23G 3/368* (2013.01); *A23G 3/54* (2013.01); *A23L 19/05* (2016.08); *A23L 25/25* (2016.08); *A23P 20/18* (2016.08); *A23P 20/20* (2016.08); *A61J 3/06* (2013.01); *A61K 31/4045* (2013.01); *A61K 31/658* (2023.05); *A61K 36/3482* (2024.05); *B08B 9/023* (2013.01); *F04B 13/00* (2013.01); *G01L 19/0092* (2013.01); *G01N 30/74* (2013.01); *A23P 10/30* (2016.08); *A61J 3/00* (2013.01); *A61J 2200/70* (2013.01); *A61J 2200/72* (2013.01); *B08B 2209/02* (2013.01); *G01N 2030/027* (2013.01)

(58) Field of Classification Search

CPC ........ A23G 3/0091; A23G 3/368; A23G 3/54; A23G 3/20; A23L 19/05; A23L 25/25; A23P 20/18; A23P 20/20; A23P 10/30; F04B 13/00; G01N 30/74; G01N 2030/027; A61J 3/06; A61J 2200/70; A61J 2200/72; A61J 3/00; B08B 9/023; B08B 2209/02; G01L 19/0092

See application file for complete search history.

(56) References Cited

U.S. PATENT DOCUMENTS

| | | | | |
|---|---|---|---|---|
| 2022/0088729 | A1* | 3/2022 | Dry | B25J 11/005 |
| 2022/0386670 | A1* | 12/2022 | Warren | A23G 3/364 |
| 2023/0077762 | A1 | 3/2023 | Warren et al. | |
| 2023/0118618 | A1* | 4/2023 | Warren | A24D 1/18 131/364 |
| 2023/0263726 | A1* | 8/2023 | Smith | A61K 9/0056 424/440 |
| 2024/0156145 | A1* | 5/2024 | Warren | A23P 20/25 |

OTHER PUBLICATIONS

Erland, Melatonin Natural Health Products and Supplements: Presence of Serotonin and Significant Variability of Melatonin Content, J. of Clinical Sleep Medicine, vol. 13, Feb. 2017, 275-281.

International Searching Authority, International Search Report and Written Opinion issued in Application No. PCT/US2025/049511, 16 pages, dated Jan. 23, 2026.

* cited by examiner

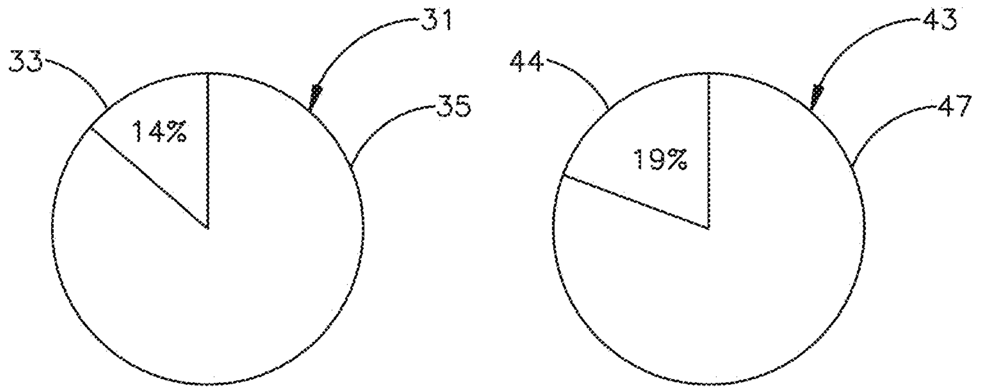
Fig.1A
Fig.1B
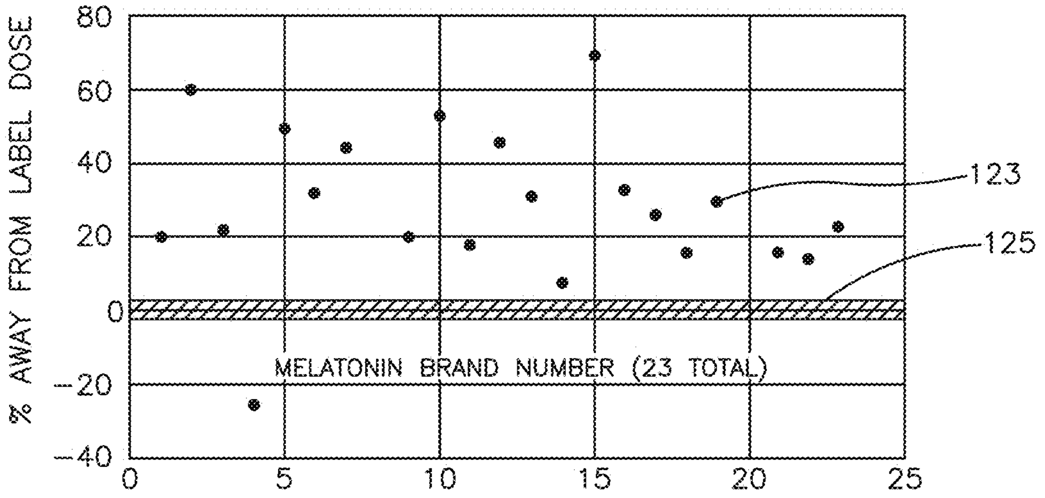
Fig.2

METHOD AND APPARATUS FOR DELIVERING AN API-CONTAINING LIQUID TO AN EDIBLE SUBSTRATE

CROSS-REFERENCE TO RELATED APPLICATIONS

This is a continuation of PCT Application Serial No. PCT/US 2025/049511 filed Oct. 3, 2025, which claims priority to U.S. patent application Ser. No. 63/702,759 filed Oct. 3, 2024, the disclosure of which is hereby incorporated by reference as if set forth in its entirety herein.

BACKGROUND

Field of the Art

The disclosure relates to the field of edible products containing active pharmaceutical ingredients, and methods and systems for manufacturing the same.

Discussion of the State of the Art

Referring to FIG. 1A, gummy vitamins are rapidly reshaping the dietary-supplement category. The gummy vitamin market 33 has captured about 14% of the overall supplement market 31, and is growing at a 13.4% compound annual growth rate. The conventional market of pills and capsules 35 occupies the remaining 86% of the overall supplement market 31. For many consumers, especially pediatric and geriatric populations, swallowing pills and capsules containing an active pharmaceutical ingredient (API) is difficult, and adherence often suffers. Gummies and other edible formats help by being easier to use, more palatable, and portable. Yet dietary supplements face limited requirements for dose accuracy and repeatability using conventional dosing methods.

By contrast, referring to FIG. 1B, the oral pharmaceuticals market 43 includes the over-the-counter (OTC) pharmaceuticals market 44 which account for approximately 19% of the approximately $850 billion dollar pharmaceuticals market 43, and the prescription pharmaceuticals market 47 which account for approximately 81% of the pharmaceutical market. In both the OTC and prescription pharmaceutical markets, far stricter dosing standards apply compared to dietary supplements. In particular, the US Food and Drug Administration requires the API dosage to be no more than a small deviation (for instance 5%, and in some cases as low as 2%) of the predetermined and labeled dosage. The inability to accurately, precisely, and repeatably dose edible alternatives, such as gummies and other food products, with a desired dosage using conventional dosing methods constrains the availability of edible alternatives to pills and capsules. Accordingly, gummies and other edible food products have yet to enter the pharmaceutical space.

Conventional methods exist for dosing an edible substrate, such as a food product, with at least one API include injection, spraying, and delivery of individual successive droplets. In one such method, droplets are dispensed from a dosing head and travel through free space under gravitational forces to the edible substrate. A widespread consumer complaint for years has been the occasional strong dose variation experienced from one edible to the next, even within the same bag of product. In one example, consumers of CBD gummies desire a reliable calming effect at the end of a trying day, only to sometimes find an unexpectedly higher, or lower, effect than the previous day.

Recently, referring now to FIG. 2, a similar shortcoming has been reported and studied in melatonin gummy products sold OTC for sleep assistance for adults and children. The recent work of Dr. Pieter A Cohen et al. published in the Journal of American Medical Association (JAMA) (Vol. 329, page 1402, April 2023) on melatonin gummy products revealed by high-performance liquid chromatography (HPLC) that twenty-two of the twenty-three products or brands contained an actual melatonin API amount that deviated from the label claim more than 10%. FIG. 2 includes a plot 123 showing the percent departure from the label claim on the vertical "y" axis, and each of the twenty-three brands on the horizontal "x" axis. Three brands were found to be underdosed (one, by 26%) and twenty brands were found to be overdosed, by an average of +26%, reaching as high as +70%. Also, an earlier and more extensive HPLC study in Canada (Erland and Saxena, J. of Clinical Sleep Medicine, Vol. 13, 2017) on non-gummy formats concluded with similar results: widely varying melatonin doses between 17% under and 478% over the label claim. These data sets make it clear that conventional dosing methods fall short of the dose accuracy and repeatability needed for the adult and child consumer.

What is therefore needed is an improved method and apparatus for reliably dosing a predetermined desired quantity of API to an underlying substrate.

SUMMARY

In contrast to the errors found when dosing edible food products with conventional methods, the present invention produces a system for dosing food products with unprecedented API dosage accuracy and manufacturing repeatability. The API dosage accuracy and repeatability can be within 5%, such as within 2%, for instance within 1%, of the predetermined and labeled API dosage in high volume manufacturing conditions, thereby overcoming consumer complaints of debilitating variation in piece-to-piece aftereffects.

In contrast to the plot 123 of FIG. 2, the present system can achieve a separate band 125 of data from a run of 1000 dosings of an API (Melatonin as depicted in FIG. 2) dosed at a predetermined target dosage of 5 mg each. By analyzing the API using precision gravimetrics to determine the dosage accuracy of every tenth substrate of the 1000 dosed substrates, the results established a dosing accuracy band of better (i.e., smaller) than +/−2% of the predetermined target dosage. It is recognized, however, that the system can be capable of achieving a dosing accuracy of less than +/−1%. The system can thus also be capable of achieving a dosing accuracy of less than +/−5%.

While the predetermined target dosage was 5 mg in one example, the dosage can be in any suitable range as desired depending on the API. For instance, the predetermined target dosage can be in a range from 0.05 milligrams (mg) to 100 mg or more. In some examples, the predetermined target dosage can be in a range from 1 mg to 100 mg or more. For instance, the predetermined target dosage can be in a range from 5 mg to 100 mg or more. The dosage of API can be delivered in a carrier liquid to define an API-containing liquid that is delivered in incremental volumes that are substantially equal to each other. In one example, the incremental volumes can be approximately 10 microliters (ul) or less. In other examples, each the incremental volumes can be in a range from approximately 50 nanoliters to approximately 5 microliters, such as from approximately 100 nanoliters to approximately 1 microliter, such as from approximately 500 nanoliters to approximately 1 microliter. Thus, the present system can deliver a predetermined dosage within a high level of accuracy at a high dosage resolution. Further, the dosing operation can deliver at the dosage to the thousand substrates within 3 hours, such as within 2 hours, such as within 90 minutes, such as within 80 minutes, such as within 60 minutes, such as within 50 minutes, such as within 40 minutes, such as within 30 minutes, such as within 20 minutes.

In one example, a method is provided for delivering an active pharmaceutical ingredient (API) to a substrate. The method can include the step of bringing the substrate into alignment with a dosing station having a conduit that terminates at a dosing head, and a positive displacement motor in fluid communication with the conduit. The method can further include the step of identifying a predetermined volume of API-containing liquid out of the dosing head, wherein the API-containing liquid contains the API and a liquid carrier. The method can further include the step of causing the motor to deliver the API-containing liquid out of the dosing head to the gummy. The method can further include the step of detecting a concentration change of the API-containing liquid in the conduit. After the detecting step, the causing step can be continued until a predetermined dosage of the API to the aligned gummy.

In another example, a method of delivering an active pharmaceutical ingredient (API) to a substrate can include the step of bringing the substrate into alignment with a dosing station that includes a dosing head. The method can further include the step of delivering an API-containing liquid out of a dosing head outlet of the dosing head, wherein the API-containing liquid contains the API disposed in a liquid carrier, and the delivering step causes a first portion of the delivered API to delivered to the substrate as delivered API, and a second portion to remain adhered to the dosing head as a residual API. The method can further include the step of causing a wash fluid to flow along the dosing head, which causes the residual API to dislodge from the dosing head and travel to the substrate.

In still another example, a method of dosing a substrate with an active pharmaceutical ingredient (API) is disclosed. The method can include the step of determining a planned total API dosage of the API to be delivered to the substrate as a number of increments of the API-containing liquid to be driven out of a dosing head outlet, wherein the API-containing liquid includes a known concentration of API. The method can further include the step of advancing the number of increments of the API-containing liquid successively out of the dosing head outlet. The advancing step can cause a quantity of the advanced API-containing liquid to define delivered API that travels to the substrate, and a residual API to remain adhered to the dosing head after the advancing step. The method can further include the step of causing the residual API to be delivered from the dosing head to the substrate. A total delivered API dosage of API in the API-containing liquid that is delivered to the substrate can be defined by a sum of the delivered API and the residual API.

In yet another example, a dosing station is configured to deliver an active pharmaceutical ingredient (API) to a substrate. The dosing station can include a reservoir containing an API-containing liquid that includes the API in a liquid carrier. The dosing station can further include a dosing head in fluid communication with the reservoir, the dosing head defining a dosing head outlet. The dosing station can further include a pump configured to drive the API-containing liquid out of the dosing head outlet so as to define a first portion of the driven API-containing liquid is delivered to the substrate, and a second portion of the driven API-containing liquid that defines a residual API that is adhered to at least one of an external surface of the dosing head and a tip of the dosing head that defines the outlet. The dosing station can further include a wash conduit configured to deliver a wash fluid to an external surface of the dosing head so as to remove the residual API and deliver the residual API to the substrate.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings:

FIG. 1A is a graphic depicting the gummy vitamin market in the overall supplement market;

FIG. 1B is a graphic depicting the OTC pharmaceuticals market and prescription pharmaceuticals market as respective percentages of the overall pharmaceuticals market;

FIG. 2 is a chart comparing dosage inaccuracies produced using conventional dosing methods to dosing accuracies in accordance with one embodiment of the present disclosure;

DETAILED DESCRIPTION

Figure 3A:
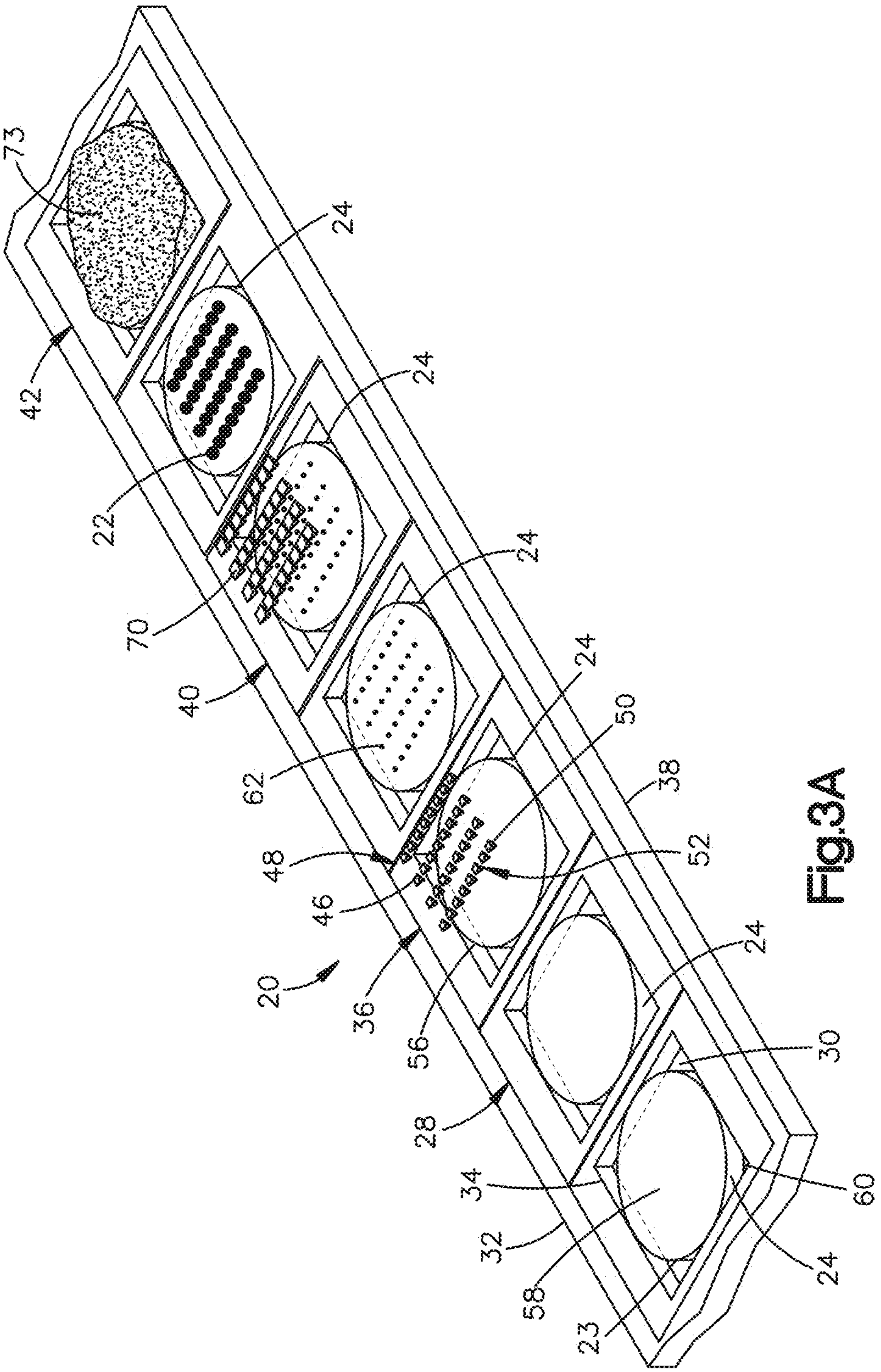
FIG. 3A is a schematic perspective view of a dosing system for delivering an active pharmaceutical ingredient to an edible product.

Disclosed are methods and apparatus for manufacturing edibles, and resulting edible products, having a predetermined dosage of API. It has been discovered that conventional droplet-based API-delivery systems limit incremental quantities of API delivered to the substrate to the quantity of API in each of the droplets. The present system relies on a volume displacement of the pump that produces a corresponding volume output of API-containing liquid to the substrate, irrespective of whether the volume output of API-containing liquid is in the form of droplets, a continuous stream, or an intermittent stream.

It has been further discovered by the present inventors that delivery of the API-containing liquid from a dosing head to a substrate can leave a residue of API adhered to the dosing head, referred to herein as residual API. Disclosed herein are methods and apparatus that are configured to both remove the residual API and deliver the residual API to the substrate. Therefore, all or substantially all (i.e., within 10%, such as within 5%, such as within 4%, such as within 3%, such as within 2%, such as within 1%, such as within 0.1%) API that is predetermined or planned to be delivered to the substrate is, in fact, delivered to the substrate.

It has further been discovered by the present inventors that the concentration of API in the API-containing liquid can change both in the reservoir and in the output line as it travels from the pump to the dosing head. Changes in the concentration can cause the dosage of API that is delivered to the substrate to change when a predetermined volume of API-containing liquid is delivered to the substrate. Therefore, the system 20 can be configured to detect in real-time a change of concentration of the API-containing liquid traveling in the output line. In one example, the real-time change of concentration can be detected at a location proximate to the dosing head. In response to the detected change in concentration, the system can correspondingly adjust an initial predetermined volume of the API-containing liquid to define an adjusted predetermined volume of API-containing liquid to be delivered to the substrate 23. Thus, a difference between the initial predetermined volume of API-containing liquid and the adjusted predetermined volume of API-containing liquid is based on the detected changes of the concentration of API in the API-containing liquid. The adjusted predetermined volume of API-containing liquid contains the predetermined dosage of API, and is delivered to the substrate when the adjusted predetermined volume of API is delivered to the substrate 23. Reference herein to "predetermined volume of API-containing liquid" can include either or both of the initial predetermined volume of API-containing liquid and the adjusted predetermined volume of API-containing liquid unless otherwise indicated.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Devices that are in communication with each other need not be in continuous communication with each other, unless expressly specified otherwise. In addition, devices that are in communication with each other may communicate directly or indirectly through one or more communication means or intermediaries, logical or physical.

Description herein of an apparatus or method steps in the singular further applies to at least one or a plurality of the apparatus or method steps. Similarly, description herein of an apparatus or method steps in the plural further includes a singular one of the apparatus or method steps. Thus, the singular terms "a" and "the" as used herein apply with equal force and effect to the "at least one" and "a plurality" unless otherwise indicated. Similarly, the terms "at least one" and "a plurality" as used herein apply with equal force and effect to the singular terms "a" and "the" unless otherwise indicated.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Figure 3B:
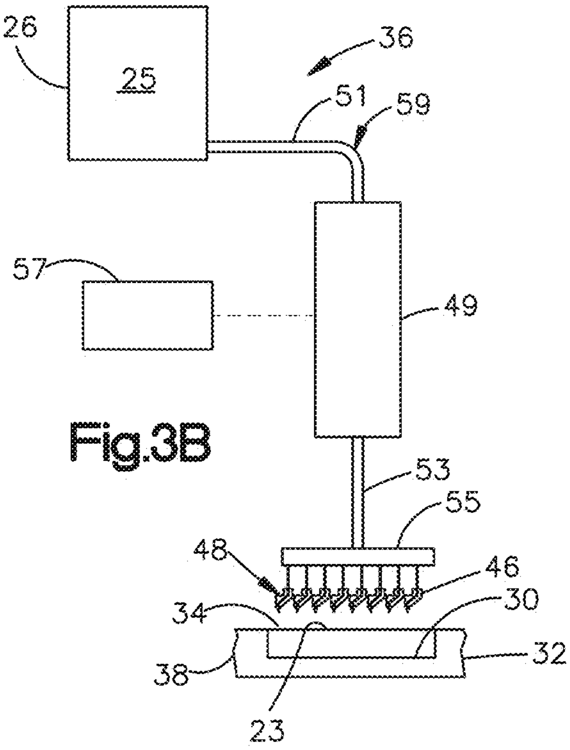
FIG. 3B is a schematic view of a dosing zone of the system illustrated in FIG. 3A.

Referring now to FIGS. 3A-3B, methods and apparatus for transforming an edible products or other substrates into an active pharmaceutical ingredient (API) containing products are disclosed. For instance, a dosing system 20 can be configured to deliver an API to a substrate 23, which can be an edible product or non-edible product. The delivering step can be performed with any suitable one or more applicators that deliver a predetermined dose of the API. In one example, the API can include one or more over-the-counter (OTC) or prescription drugs including those that provide one or both of a health benefit or recreational drug experience, or otherwise controlled ingestible materials, and herbal medicines including herbal Chinese medicines, supplements, and the like.

In other examples, the API can include a cannabinoid, which as used herein refers to any extract from a marijuana plant or hemp plant, such as CBD, THC, or any alternative cannabinoid, alone or in combination with any one or more of a flavonoid or terpene. The extract can be in its pure form or processed as desired. The terpenes and/or flavonoids could be extracted from cannabis or hemp, or can be provided as pure substances acquired or synthesized commercially from other sources.

While the dosing system can provide for the addition of at least one API in the form of a cannabinoid to a substrate, and thus cannabinoids are contemplated as a market for the final product, applications of the systems and methods disclosed herein are possible and envisioned beyond cannabis, including (but not limited to) other active pharmaceutical ingredients (API). The API can therefore include cannabis including acidic, neutral, and/or emulsified forms of cannabis, or other non-cannabis substances, to substrate. The cannabis extract can thus be in its pure form or processed as desired, including as example, emulsified forms of cannabis fluids.

Thus, reference herein to an active pharmaceutical ingredient can include any one or more of the following: one or more over-the-counter drugs, one or more prescription drugs, cannabis and cannabis plant-derived compounds, including one or more cannabinoids in either natural oily forms or emulsified forms, one or more flavonoids, one or more terpenes, and one or more herbal medicines or supplements. Reference herein to an API can further include any one or more active ingredients having a medicinal benefit, including prescription medications and over-the-counter medications, and further including vitamins, nutritional and longevity supplements, and nootropics or so-called "smart drugs" as desired. In one example, the API can include melatonin. Reference herein to an active pharmaceutical ingredient can alternatively or additionally include one or more up to all of the following: psychedelic or hallucinogenic ingredients such as psilocybin and psilocyn, and synthetic opioids including synthetic opioid pain reducers. While accurately dosed synthetic opioids can replace the more potent ingredients such as fentanyl, it should be appreciated that the API can alternatively or additionally include potent ingredients, recognizing the accurate dosage of the type described herein can be of importance when administering an API that can have undesirable consequences when inaccurate dosages are administered. Similarly, reference to one or more of the active pharmaceutical ingredients identified above can apply equally to any other of the active pharmaceutical ingredients identified above. According to an aspect of the present disclosure, a method and apparatus for delivering a cannabinoid or conventional drug may also be used to deliver homeopathic remedies, herbal supplements with flavors or odors, and so forth to an edible product. The resulting edible product can be referred to as a "nutraceutical," as its definition is "a food containing health-giving additives or having medicinal benefit."

The active pharmaceutical ingredient can be added to the substrate 23 to produce an active-containing or dosed substrate. Referring to FIGS. 6A-6D generally, the substrate 23 can be configured as an edible product 24 such as a food product. Prepared edible products 24 such as prepared food products can include, by way of example and not limitation, any one or more up to all of savories such as edible nuts 37 (FIG. 6A), fruits such as dried fruits 39 (FIG. 6B), baked goods such as brownies 41, and soft candies such as gummy candies 45. Gummy candies 45 can be certified as chewable gels by US Pharmacopeia having a principal place of business in Rockville, MD. It is recognized, of course, that the edible product 24 can also include a food product that has not been fully prepared. For instance, the active pharmaceutical ingredient can be added to a food product during production of the food product.

It is appreciated that the API is not visible in FIGS. 6A-6D due to the nature of the figures. The active pharmaceutical ingredient can be applied to the nuts and fruits in any suitable manner as disclosed herein. In some examples, the nuts have been cooked, such as roasted. In other examples, the nuts can be raw. In some instances, the nuts or fruit can be prepared with salt, sugar, honey, or any suitable alternative ingredient. Thus, the nuts can be candied. In some examples, the fruit can be a raw fruit. In other examples, the fruit can be dried. In still other examples, the fruit can be candied. It is understood that fruits and nuts can have relatively low surface areas and volumes. Thus, variations in the dosage of active pharmaceutical ingredient applied to fruits and nuts can have a greater impact on the ratio of active pharmaceutical ingredient per volume of edible product when compared to edible products having larger surface areas and volumes.

Therefore, it can be particularly advantageous to precisely control the dosage of active pharmaceutical ingredient added to fruits and nuts. The active pharmaceutical ingredients can be applied to the fruits and nuts as microquantities in the manner described above, which allows for the precise control of the dosage of active pharmaceutical ingredients applied to the fruits and nuts. Thus, each fruit or nut can include a quantity or dosage of API in the range from approximately 0.5 micrograms to approximately 250 milligrams, such as to approximately 25 milligrams, and anywhere in between. It is recognized, of course, that the dosage of API per dried fruit or nut can vary as desired. For instance, other dosages of API can be delivered to fruits and nuts, for instance depending on the size of the fruit and nut, the volume of the API-containing liquid that is delivered to the dried fruit or nut, and the concentration of API in the API-containing liquid. The API-containing liquid can be delivered in increments that allow the dosage of API delivered to a substrate to be precisely controlled as described above. Further, the dosage of API per dried fruit or nut can be precisely controlled, as can a plurality of dried fruits and/or nuts that amount to a serving. For larger edible products, such as baked goods 41 (see FIG. 6C), the API-containing liquid can be applied in a range from approximately 5 nanoliters to approximately 1000 microliters over an entire surface and greatly increase the total API delivered to the substrate to 100 milligrams or more.

It is recognized that the edible product 24 can include any suitable prepared food product such as hard candy, chocolates brownies, cookies, soft candies such as gummy candy, savories such as trail mix bars or dried meat pieces, and the like. Thus, in some examples, the prepared edible products can be cooked food product. In some specific examples, the prepared edible products can be baked food product. The prepared edible product can be bite sized, such as M&M candy, gummy candies, chocolate kisses, or the like, or can be designed to require more than one bite for full consumption, such as a cookie. Thus, it should be appreciated that the prepared edible product can be a cooked food product. For instance, the prepared edible product can be a baked food product. Thus, in some examples, the prepared edible product can include a plurality of mixed ingredients. In some examples, the prepared edible products can be a dehydrated food product, such as dried fruit or jerky. In other examples, the prepared edible product can be freeze dried. In still other examples, the prepared edible product can be a raw food product, such as nuts or fruit. It will thus be appreciated that the application of the active pharmaceutical ingredient to the previously prepared food product can allow for a broader range of food product to be made with active pharmaceutical ingredients. It will be appreciated that because the active pharmaceutical ingredients are applied to previously prepared food product, active pharmaceutical ingredients having short shelf lives can be applied to the substrate and ingested in a shorter period of time with respect to active pharmaceutical ingredients that are combined with the raw ingredients that are then processed to prepare the food product.

In one aspect, a plurality of active-containing substrates can be provided as a set, wherein each of the substrate is dosed with substantially the same dosage of API. In other examples, some of the substrates can have different dosages of the API and are designed to be ingested at different times among a period of time, such as different days of the week. Thus, a desired dosage profile can be delivered to the patient throughout the period of time. Alternatively or additionally, one of the active-containing substrates can contain a different API or combination of APIs. Thus, the set of active-containing substrates can be designed to be sequentially ingested (that is, ingested one after the other) over the period of time, thereby delivering a desired predetermined sequence of active pharmaceutical ingredients to the patient.

The active pharmaceutical ingredient can be delivered to the substrate in liquid form as an API-containing liquid. The API-containing liquid can be in the form of a pure API, or can be in the form of a concentration of API in a liquid carrier. In some examples, the API-containing liquid can be in the form of a solution, such that the liquid carrier defines a solvent. In other examples, the API-containing liquid can define a suspension, mixture, emulsion, or an encapsulation of the API. In order to assist in achieving predictable doses of the API, the API can be substantially homogeneously disposed within the API-containing liquid. Thus, the API-containing liquid can consist of or consist essentially of the API, either purified, partially purified, or unpurified, in liquid form having a desired viscosity that allows for the API to be reliably dispensed. In some examples, the API-containing liquid can be heated to achieve a desired viscosity. In some examples, the API-containing liquid can have an oily or hydrophilic nature. For instance, the API-containing liquid may be multilayered, with a protein or other protective coating surrounding a precise dosage of an oil-based or water-based formulation. Because the concentration of the API in the API-containing liquid is known, a volume of liquid can be predetermined and delivered to the substrate to achieve a desired predetermined approximate dose of the API to the substrate.

In some examples, an applicator such as a dosing head can deliver one or more microquantities or any suitable dosage of the API to the substrate. For instance, the API-containing liquid can be delivered to the substrate 23 from the applicator in the form of individualized successive droplets, a continuous stream, an intermittent stream, or combination thereof, of the API-containing liquid. In still other examples, the API-containing liquid can be delivered to the substrate 23 in the form of a spray. In one example, the API can have a concentration in the API-containing liquid in a range from approximately 50 micrograms per microliter of solution to approximately 1 milligram per microliter of solution. In other examples, the API-containing liquid can be a pure resin of the API.

As will be described in more detail below, dosing heads can be provided that are configured to deliver any suitable volume of API-containing liquid to the substrate 23. The API-containing liquid can contain high concentrations of API in the liquid carrier of the API-containing liquid. Thus, a desired dose of API can be delivered to substrates both large and small in size, while keeping the volume of liquid carrier delivered to the substrate manageable so as to avoid flooding out the substrate with API-containing liquid. In some examples, the volume of API-containing liquid, that is delivered to the substrate 23 so as to deliver the predetermined dosage of API, can be delivered as an intermittent stream. Thus, the liquid carrier of a previous intermittent stream segment of the intermittent stream can evaporate from the substrate 23 before a new intermittent stream segment of the intermittent stream is delivered. The intermittent stream segments can be delivered until the predetermined dosage of API has been delivered to the substrate 23.

It is envisioned in one example that dosage heads delivering like dosages of API to like substrates can deliver approximately the same predetermined volume of API-containing liquid. As will be appreciated from the description below, the volume delivered by one or more up to all of the dosing heads can be adjusted based on a detected change of concentration of API in the API-containing liquid during the dosing operation. Thus, for instance when delivering the API to dried fruits and/or nuts designed to have the same dosage of API, the dosing heads can deliver the approximately same dosage of API to each dried fruit and/or nut, or to a group, such as a serving, of dried fruits and/or nuts.

The dosage of API delivered to the substrate 23 can be precisely controlled by managing the volume of API-containing liquid that travels out of the dosing head. As will be appreciated from the description below, the system can include a pump having a positive displacement motor that performs incremental displacements that, in turn, delivers the API-containing liquid in known incremental volumes. In one example, the incremental displacements can be performed as successive steps of a stepper motor. A predetermined number of incremental displacements of the motor delivers a known predetermined volume of API-containing liquid out of the dosing head, irrespective of whether the API-containing liquid delivered to the substrate 23 includes droplets, an intermittent stream, or a continuous stream. The delivery of the API-containing liquid to the substrate can be discontinued when it is determined that the total API in the volume of API-containing liquid that has been delivered by the pump substantially equals the predetermined dosage of API. The phrase "substantially equals" and derivatives thereof in this context can mean within 10% of the predetermined dosage, such as within 5% of the predetermined dosage, such as within 3% of the predetermined dosage, such as within 2% of the predetermined dosage, such as within 1% of the predetermined dosage, such as within 0.1% of the predetermined dosage, such as being equal to the predetermined dosage.

As will be appreciated below, the predetermined dosage of API can be delivered in a predetermined volume of API. The predetermined volume of API can be delivered by performing a predetermined number of successive incremental displacements of the motor. However, as will be appreciated from the description below, the system 20 is configured to determine whether the concentration of API in the API-containing liquid changes as it travels through the second conduit. If so, the system 20 is configured to determine an adjusted volume of API-containing liquid, and thus an adjusted number of motor displacements to be performed, to emit the total predetermined dosage of API out of the dosing head, and to the substrate 23 either in the initial volume of API or in a residual volume of API.

As described above, the API-containing liquid can be delivered in the form of droplets, a continuous stream, and/or an intermittent stream. In this regard, as described in more detail below, a pump delivers API-containing liquid in repeatable identical incremental volumes of the API-containing liquid. As a result, the number of increments performed by the pump multiplied by volume of API-containing liquid delivered to the substrate 23 in each increment multiplied by the concentration of API in the API-containing liquid equals the dosage of API delivered to the substrate, irrespective of whether the API-containing liquid is delivered as drops of the same or different volumes, a continuous stream, or an intermittent stream. The precise repeatable known quantities of the volume of the liquid 25 can be delivered to the substrate 23. As a result, the edible products 24 can receive a predictable dosage of the active pharmaceutical ingredient within federal regulations. Further, the total dose of API delivered to the substrate 23 can be known without the use of elaborate and expensive imaging systems that image and analyze droplets as they travel from the dosing head to the substrate. Of course, such an imaging system can be employed if desired. In one example, the dosage of API to be delivered to the substrate can be in a range from approximately 0.5 micrograms to approximately 250 milligrams, such as approximately 25 milligrams.

In one example, when the API-containing liquid is delivered as individual successive droplets, the droplets can be configured as microdroplets each having a volume in a range from approximately 2 nanoliters to approximately 20 nanoliters, such as from approximately 2 nanoliters to approximately 10 nanoliters, such as from approximately 5 nanoliters to approximately 10 nanoliters. In another example, the microdroplets each can have a volume in a range from approximately 5 nanoliters to approximately 20 nanoliters. In one specific example, the microdroplets can each have a volume in a range from approximately 25 nanoliters to approximately 2 microliters. In still other examples, the microdroplets can each have a volume that is in a range from approximately 25 nanoliters to approximately 1 microliter. In other examples, the volume can be in a range from approximately 50 nanoliters to approximately 1 microliter. Each microdroplet can contain a microquantity of API in a range from approximately 0.5 micrograms to approximately 1 milligram. At least some of the microdroplets 62 up to all of the microdroplets can be substantially spherical shaped. Alternatively or additionally, at least some of the microdroplets up to all of the microdroplets can be elongated along the direction of travel, for instance substantially teardrop shaped or alternatively shaped as desired.

The API-containing liquid can define a maximum cross-sectional dimension along a select direction as it travels from the dosing head 46 to the substrate 23. The maximum cross-sectional direction can be in a range from approximately 5 millionths of an inch, for instance when printed, up to approximately 100 thousandths of an inch. For instance, the range can be from approximately 5 thousandths of an inch to approximately 50 thousandths of an inch. In one example, the maximum cross-sectional dimension along the select direction can be in a range from approximately 20 thousandths of an inch to approximately 40 thousandths of an inch. The dosing heads 46 are spaced from the edible products 24 along a direction of travel of the active pharmaceutical ingredient from the dosing heads 46 to the edible products 24. Thus, the active pharmaceutical ingredient is delivered to the substrate along the direction of travel. The select direction can be substantially perpendicular to the direction of travel. In one example, the dosing heads 46 are spaced above the edible products 24 along a vertical direction. Thus, the select direction can be a substantially horizontal direction. For instance, the dosing heads 46 can be spaced from the edible products 24 any suitable distance when delivering the active pharmaceutical ingredient to the edible products 24, such as from approximately 2 mm to approximately 25 mm. In other examples, the droplets can be configured as nanodroplets having volumes and/or concentrations less than those described above with respect to the microdroplets. In still other examples, the droplets can be configured as macrodroplets having volumes and/or concentrations greater than those described above with respect to the microdroplets.

The at least one API-containing liquid to be delivered to the substrate 23 can include a single desired API and no other APIs. Thus, the single API can be delivered to the substrate. In some examples, the API-containing liquid can be a pure extract of the API. Alternatively, a plurality of different liquids can be delivered to the substrate, each containing their own different one or more APIs. Accordingly, by delivering multiple different liquids, a plurality of desired APIs can be delivered to the substrate. The liquids can be delivered in the same quantity or in different quantities. Accordingly, the ratio of one or more APIs relative to one or more other APIs can be controlled. In other examples, the liquid to be delivered to the substrate can include a plurality of APIs, either in equal proportions or in desired ratios. Thus, a single liquid can be delivered to the substrate to deliver either a single API or a plurality of APIs. The plurality of APIs delivered to the food product with one or more liquids can include greater than one API. Alternatively still, a single liquid containing multiple APIs can be delivered to the substrate. It can be said that at least one API-containing liquid containing a predetermined concentration of at least one API that can be delivered to the substrate.

The API-containing liquid can have a concentration of API as desired. For instance, the concentration of API in the API-containing liquid can be in a range from approximately 50 micrograms of API per microliter of API-containing liquid to approximately 1 milligram per microliter of API-containing liquid.

When the API is added to the edible product after the edible product has been prepared, the API is not subjected to the food preparation process in some examples. Thus, the API is not subjected to the mixing of ingredients of the food product, the cooking of the food product, the freeze drying of the food product, the dehydration of the food product, or the like. As a result, the active pharmaceutical ingredient is not subject to processes that might otherwise degrade the efficacy of the active pharmaceutical ingredient. The present disclosure recognizes, however, that the methods of delivering the API to food product can further be applied to raw food product, such as raw fruit and nuts, and other edible substrates, and can also be applied to food product in production.

According to another aspect, the API can be applied to the substrate via any suitable printing process, including 3D, inkjet printing, or any suitable alternative printing process. In some cases, such printing can be used to apply, for example, any suitable label such as a warning symbol or warning, and the ink dots used in the printing could be composed largely of a targeted formulation derived from the API. In some aspects, formulations used for precise addition to edible products may comprise a substantial fraction of a plurality of any suitable APIs. In some examples, the at least one API can be deposited on a location of a product that is not designed to be brought into direct initial contact with the tongue during ingestion, thereby further masking the taste of the at least one API. For instance, the at least one API can be applied to the top rounded surface of a cookie, it being recognized that cookies are designed to be placed into the mouth with the bottom flat surface against the tongue. Alternatively or additionally, the API can be coated with a sugar or other suitable taste-masking agent as desired.

In some aspects, soft edible products such as chocolate, gummies, licorice, and the like can be used as a “carrier” or “host” for a quantity of API that can be injected into the soft edible product (by air gun, or by needle, or by other suitable methods known in the art), to push the added material into the bulk of the soft edible product. In some aspects, energy such as infrared light, forced air, or microwaves may be applied to a surface of an edible product to soften (or further soften) the material in a small area, and the API may be injected into the area pre-treated with infrared more easily (or to a great depth in the host edible product). The energy can be applied before injection, after injection, or both before and after injection. In other examples, the at least one API can be applied to multiple surfaces of the edible product up to all surfaces of the edible product.

For edible products, for instance candies, hard or soft, or any other suitable edible substrate, a visible designs the API acting as the ink can be printed on the item. One may print the API having an indication of the dosage of the API formulation as desired. Doses may also be sprayed on, or added as an additional layer, such as a candy or chocolate layer. In some aspects, the at least one API can be mixed in with food ingredients, particularly when such ingredients are suitable for addition, shortly prior to packaging or delivering a prepared edible product (for example, as an ingredient in an icing or other coating, or as part of the sugar coating applied to gummy candies.

In some aspects, an edible product can be coated with small oil spheres or a coating of solid powder, each containing the at least one API, to block taste or hide the flavor of the API. In some aspects, colorant may be added to the at least one API prior to delivering the at least one API to the edible product, in order to blend the formulation blend with the coloring of the edible product.

According to an aspect, the applicator of the dosing system 20 can encapsulate or mix the API-containing material with one or more modifiers that are configured to modify at least one or more of flavor, mechanical properties, or aesthetics of the API before adding the API to the edible product. According to an aspect, the applicator can adjust size, location, or distribution of the API-containing material on the edible product to modify flavor or aesthetics. According to one example, energy can be added to a surface of the edible product to increase adhesion of the API-containing material to the edible product. For instance, energy can be added to increase a temperature at the surface. In one aspect, the temperature can be increased by directing at least one of forced air, microwaves, and light, such as infrared light, to the surface. The energy can be added prior to delivering the API-containing material to the edible product, after delivering the API-containing material to the edible product, or both before and after delivering the API-containing material to the edible product. No matter the methodology in which the API is delivered to the substrate 23, and as described in more detail below, the system 20 can include a wash station that delivers to the substrate residual API that may be adhered to the dosing head.

Referring now to FIGS. 3A-3B, all of the above method steps and apparatus described herein, including an active-containing substrate, can be incorporated into or provided by any suitable system. While one such dosing system 20 is illustrated and described herein, it is recognized that numerous alternatives are available for dispensing an approximate dose of the active pharmaceutical ingredient onto or into a desired substrate as described above. In one example, the dosing system 20 is configured to deliver an active pharmaceutical ingredient 22 to a substrate 23, which can be configured as an edible product 24, thereby producing an active-containing substrate. When the substrate is an edible product, the active-containing substrate can be referred to as an active-containing edible product. As described above, the edible product 24 can be any suitable fully prepared food product.

In some instances, it may be desirable to add one or more auxiliary edible products to the prepared edible product 24, either before or after delivering the active pharmaceutical ingredient 22 to the edible product 24. Examples include adding icing to a cookie, or frosting to a brownie or cake. However, in these examples, the cookie and brownie can have been fully cooked or otherwise prepared prior to adding the pharmaceutical ingredient. The system 20 can include one or more up to all of a delivery station 28 that is configured to receive one or more edible products, a dosing station 36 configured to deliver an approximate dose of the active pharmaceutical ingredient (API) 22 to the one or more edible products, a post-processing station 40, and a packaging station 42 that can be configured to package the edible product 24 that carries the approximate dose of the active pharmaceutical ingredient 22. In some examples the approximate dose can be a precise dose as described herein. The post-processing station 40 can be configured to at least one of 1) dries a solvent, for instance, when the API is delivered as a solution, 2) increases a viscosity of the API, 3) further adheres the API to the substrate, 4) disperses the API along the substrate, and 5) increases absorption or diffusion of the API into the substrate.

The terms "substantial," "approximate, "about," and words of similar import when used with respect to a quantity, volume, mass, weight, dosage, size, shape, direction, or other parameter, include the stated parameter specifically along with ranges within plus and minus 20% of the stated parameter, for instance plus and minus 10% of the stated parameter, including within plus and minus 5% of the stated parameter, such as within plus and minus 2% of the stated parameter, including plus and minus 1% of the stated parameter, including plus and minus 0.1% of the stated parameter unless otherwise indicated.

The API-containing liquid 25, can be a solution of the type described above, a pure API for instance as an oil, a suspension, an emulsion containing API, an encapsulation of the API, or any suitable API mixture. The system 20 can include a reservoir 26 that is configured to retain the API-containing liquid 25. Thus, while the liquid 25 can be a pure API, in other examples the API can be mixed or otherwise combined with one or more other materials as desired, such as a solvent so as to define a solution. In one example, the liquid is a solution having an approximate concentration of the API described above. The approximate concentration of the API in the API containing liquid 25 can be a known concentration described above. Thus, the active pharmaceutical ingredient 22 can define the solute of the solution, and the solution can define any suitable solvent. In one example, the solvent can be an alcohol, such as ethanol or any alternative alcohol as desired, or any other viscosity reducing agent as desired. Thus, the solvent can comprise, consist of, or consist essentially of, ethanol. However, it should be appreciated that the solvent can be an alcohol such as, ethyl acetate, water, or an organic fluid. In one example, the organic fluid can be defined by a medium-chain triglyceride (MCT) oil. In other examples, when the API-containing liquid is a suspension, the liquid carrier of the suspension can be an organic fluid, such as MCT oil.

In one example, the API-containing liquid 25 can contain a concentration of the API that is in a range from approximately 10% to approximately 70%, such as from approximately 30% to approximately 70% by volume with the solvent. For instance, the API-containing liquid 25 can contain a concentration of the API that is in a range from approximately 10% to approximately 90%, including any one of approximately 20%, approximately 30%, approximately 40%, approximately 50%, approximately 60%, approximately 70%, approximately 80%, and approximately 90%. It is appreciated that the concentration of API depends at least partially on the API and the liquid carrier in the API-containing liquid. It is recognized that some liquid carriers, such as alcohol solvents, will be removed substantially in its entirety during a subsequent drying step after being delivered to the substrate. For instance, the solvent can easily evaporate after being applied to the edible product 24, leaving the API adhered to the edible product 24. Nevertheless, it may be desired for the solvent to be safe for consumption in trace amounts. It is recognized that other liquid carriers, such as oils, will remain on the substrate and will not dry.

Alternatively, the API-containing liquid 25 can be a pure API, which can include a synthesized API or an extracted API, meaning that it is not mixed with a carrier that is designed to be burned or otherwise evaporated off. The API can be purified, partially purified, or unpurified as desired. It is recognized that such stand-alone APIs can have a relatively high viscosity that can prevent the API from being suitably free flowing for easy delivery to the substrate 23. Therefore, as described in more detail below, the system 20 can include one or more heaters that are configured to raise the temperature of the API, thereby lowering the viscosity of the API-containing liquid. Alternatively or additionally, an additive such as alcohol can be added to the liquid 25 that lowers the viscosity of the liquid. The alcohol readily evaporates after the liquid 25 has been applied to the substrate 23, leaving the API adhered to the substrate 23. In one example, the API-containing liquid can penetrate into the substrate 23 prior to evaporation of the liquid carrier. Thus, the API can remain beneath the surface that faces the dosing head 46 in some examples. It is recognized that the API having a suitably low viscosity can be readily delivered to the substrate in any manner described herein. For instance, it can be desirable to maintain the API at a heated temperature during application of the API to the substrate 23. The heated temperature can range from about 100 degrees F. to about 200 degrees F., such as about 150 degrees F. to approximately 180 degrees F. Although it is envisioned that the API has a sufficiently low viscosity at room temperature, it may nevertheless be desirable in some instances to maintain the solution at the heated temperature. Because the approximate dose of the API in the liquid 25 is known, a predetermined approximate volume of the liquid 25 delivered from the reservoir 26 to the dosing station 36, and thus to the substrate 23, can contain approximately a predetermined approximate desired dose of the pharmaceutical ingredient 22.

The delivery station 28 can be configured to receive a plurality of substrates 23 such as a plurality of edible products 24 that can be sequentially aligned with a respective at least one dosing head 46 that delivers the API-containing liquid 25 to the aligned substrate. This, while the substrates 23 are illustrated as edible products 24, it is recognized that the substrates can be configured as any suitable alternative substrate as described above. In one example, the system 20 includes one or more support surfaces 30 of at least one support member 32 or stages that are configured to receive and support a respective one or more substrates 23. The support surfaces 30 can be defined by respective predetermined locations of the support member 32. The predetermined locations can be defined by geometric markings. Alternatively or additionally, the predetermined locations can be defined by pockets 34 that are defined by the support member 32. At least one or both of the support member 32 and the dosing station 36 can be movable so as to bring the dosing station 36 into alignment with the edible product 24. The dosing station 36 can be configured to deliver the approximate volume of the liquid 25 to one edible food product at a time, or can be configured to deliver a plurality of approximate volumes of the liquid 25 to a respective plurality of edible food products simultaneously. In this regard, descriptions herein of singular elements apply with equal force and effect to a plurality of the singular element and at least one of the singular element. Thus, the term "a," "an," "the" as used herein in connection with a singular apparatus or method step includes a plurality of the apparatus or method steps and at least one of the apparatus or method steps. Conversely, descriptions herein of plural elements apply with equal force to the singular element, or at least one of the singular element. Thus, a plural apparatus or method steps described herein includes the singular "a," "an," and "the," as well as "at least one."

In one example, the support member 32 can be configured as any suitable delivery member such as a conveyor 38 or other suitable support member that is designed to support and transport the edible products to be brought into operative alignment with the dosing station 36. The conveyor 38 can be movable so as to correspondingly transport the edible product 24 from the delivery station 28 to the dosing station 36. Alternatively, the support surface 30 can be stationary, and the dosing station 36, including the applicator which can be configured as one or more dosing heads as described below, can be movable to be brought into alignment with the substrate 23. Alternatively still, both the support surface 30 and the dosing station can be movable so as to bring the dosing heads into alignment with the substrate 23. Thus, it can be said that at least one of the support surface 30 and the dosing station 36 can be movable with respect to the other of the support surface 30 and the dosing station 36 so as to bring the substrate 23 into alignment with the dosing heads of the dosing station 36.

After the API has been delivered from the dosing station 36 to the substrate 23, the active-containing substrate 23 can be moved from the dosing station 36 to the post-processing station 40. The active-containing substrate 23 can be moved from the dosing station 36 to the post-processing station 40 using the support surface 30 or any suitable alternative apparatus. In this regard, the post-processing station 40 can be positioned inline with the dosing station 36 along the support surface 30 in some examples. Alternatively, the post-processing station 40 can be offline with respect to the support surface 30. Thus, the active-containing substrate can remain at the post-processing station 40 for as much time as desired until the active-containing substrate is suitable to be packaged. At that point, the active-containing substrate can be moved from the post-processing station 40 to the packaging station 42. The support surface 30 or any suitable alternative apparatus can move the active-containing substrate from the post-processing station to the packaging station 42. In this regard, the post-processing station 40 can be positioned inline with the dosing station 36 along the support surface 30, or can be offline with respect to the support surface 30.

Once the edible product 24 is aligned with the dosing station 36, the dosing station 36 is configured to deliver a predetermined approximate volume of the API to the edible product. In some examples, the active pharmaceutical ingredient can be presented as the liquid 25. Because the concentration of the active pharmaceutical ingredient in the liquid 25 is known, and the desired dose of the active pharmaceutical ingredient to be delivered to the substrate 23 is known, the approximate volume of the liquid 25 to be delivered to the substrate 23 can be determined. In some examples, electrostatic forces can be created that drive the active pharmaceutical ingredient to the substrate 23, whereby the active pharmaceutical ingredient and the substrate are oppositely charged. For instance, the substrate 23 can be provided with a negative electrical charge, and a positive charge can be applied to the liquid to be delivered, thereby creating the electrostatic charge.

Figure 4:
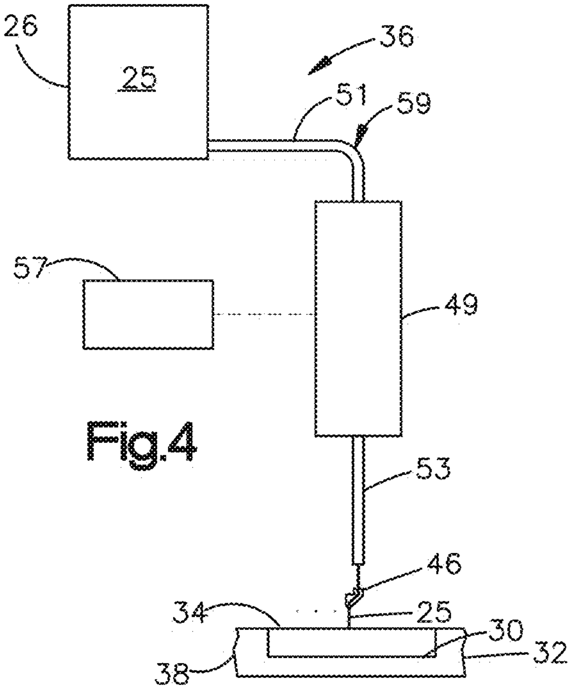
FIG. 4 is a schematic view similar to FIG. 3B, but showing a dosing zone in another example.

The dosing station 36 can include at least one applicator of the type described above, such as a plurality of applicators. Each applicator can define at least one dosing head 46 that is configured to dispense a respective approximate quantity of the approximate volume of the liquid 25 that is delivered from the reservoir 26. Thus, the dosing station 36 can include at least one dosing head 46 such as a plurality of dosing heads 46. As shown at FIG. 3B, the dosing station 36 can include a plurality of dosing heads 46 that are in fluid communication with a pump 49 and is configured to deliver a volume of API-containing liquid that is driven by the pump 49. The pump can be configured as desired, and in one example is commercially available from TriContinent having a principal place of business in Auburn, CA. Alternatively, as shown at FIG. 4, the dosing station 36 can include a single dosing head 46 that is in fluid communication with pump 49 and is configured to deliver a volume of the API-containing liquid 25 that is driven by the pump 49. The dosing station 36, and in particular the at least one dosing head 46, is in fluid communication with the reservoir 26. Thus, the dosing heads 46 are configured to receive respective a volume of the liquid 25 delivered from the reservoir 26 by the pump 49, and dispense the volume of the liquid 25 to the edible product 24.

Figure 5:
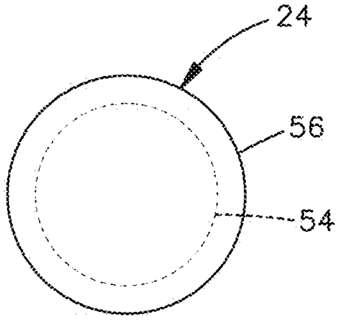
FIG. 5 is a plan view of the edible product illustrated in FIG. 3A, showing a delivery zone.
Figure 6A:
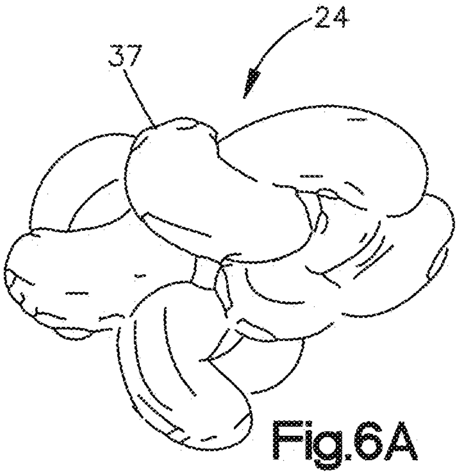
FIG. 6A is a perspective view of mixed nuts dosed with an active pharmaceutical ingredient in accordance with aspects of the present disclosure.
Figure 6B:
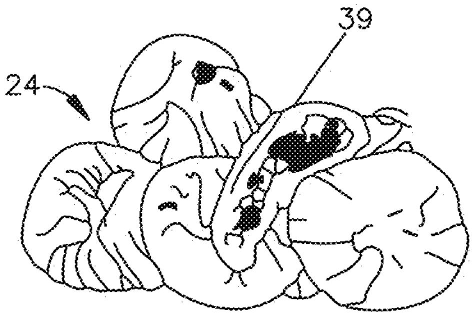
FIG. 6B is a perspective view of dried fruit dosed with an active pharmaceutical ingredient in accordance with aspects of the present disclosure.
Figure 6C:
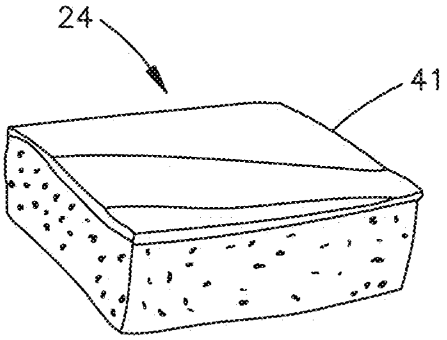
FIG. 6C is a perspective view of a baked good dosed with an active pharmaceutical ingredient in accordance with aspects of the present disclosure.
Figure 6D:
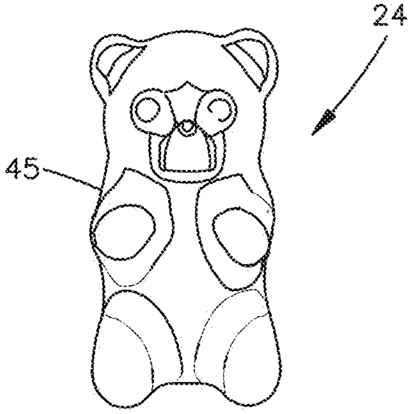
FIG. 6D is a side elevation view of a gummy candy dosed with an active pharmaceutical ingredient in accordance with aspects of the present disclosure.

Further, referring to FIG. 5, the dosage of the API can be applied at specific locations of the edible product as desired. For instance, in certain examples, it may be desirable to deliver the API such that it is substantially evenly distributed on or in the edible product 24. As a result, consumption of different regions of the edible product in equal volumes will cause ingestion of substantially identical quantities of the active pharmaceutical ingredient. When the edible product is a small or bite-size food product such as a dried fruit or nut, the concentration of API in the liquid 25 can be sufficiently high such that the API-containing liquid can be delivered to the food product in sufficient quantity so that the planned or predetermined dosage of API is delivered to the food product, but not in so much quantity that the API-containing liquid will flood the food product.

Referring to FIGS. 3A-3B and 5, the dosing head 46 can be aligned with different respective locations of a dosing zone 54 the edible product 24. Accordingly, the dosing heads 46 can be positioned to deliver their respective quantities of the volume of liquid 25 to the different respective locations of the dosing zone 54. Further, the system 20 can be configured to deactivate select dosing heads 46 that are out of alignment with the dosing zone 54 and thus do not receive respective portions of the volume of liquid 25, and activate select dosing heads 46 that are aligned with the dosing zone 54 and thus receive respective portions of the volume of liquid 25. In some examples, the system 20 can include a sensor that identifies the dosing zone 54 of the edible product 24. The sensor can be a camera, a weight sensor that measures the weight of the substrate 23 on the support surface and determines the dosing zone based on the weight and/or size, or any suitable alternative sensor. The dosing zone 54 can be at least partially defined by an outer perimeter 56 of the edible product 24. For instance, the dosing zone 54 can be defined in its entirety by the outer perimeter 56 of the edible product 24. Thus, an entire outer surface of the edible product 24 can define the dosing zone 54. In some examples, the dosing zone 54 can be disposed inside the outer perimeter 56 in its entirety. For instance, the dosing zone 54 can be greater than half, for instance greater than 75%, of a footprint defined by the outer perimeter. Either way, it can be said that the dosing zone 54 can be a substantially predetermined location with respect to the outer perimeter 56 of the edible product 24. Thus, the dosing zone 54 can be consistent among a plurality of differently sized edible products 24, such as cookies or brownies that can have similar but non-identical sizes and shapes.

Alternatively, referring to FIGS. 4-5, the dosing head 46 can be aligned with a target location in a desired dosing zone 54 the edible product 24. Accordingly, the dosing heads 46 can be positioned to deliver their respective quantities of the volume of liquid 25 to the target location of the dosing zone 54. The dosing zone 54 can be at least partially defined by an outer perimeter 56 of the edible product 24. For instance, the dosing zone 54 can be defined in its entirety by the outer perimeter 56 of the edible product 24. Thus, an entire outer surface of the edible product 24 can define the dosing zone 54. In some examples, the dosing zone 54 can be disposed inside the outer perimeter 56 in its entirety. Thus, the dosing zone 54 can be defined by a region of the substrate 23 that is circumscribed by the outer perimeter 56. For instance, the dosing zone 54 can be greater than half, for instance greater than 75%, of a footprint defined by the outer perimeter. The API-containing liquid 25 can be delivered to the target location, such that the API-containing liquid 25 flows along the surface of the substrate 23 that faces the dosing head 46, such that the API-containing liquid 25 is substantially homogenous across a substantial entirety of the dosing zone 54. Therefore, when the API-containing liquid evaporates, the remaining API is substantially uniformly adhered to the substrate 23 across a substantial entirety of the dosing zone 54. The dosing zone 54 can be consistent among a plurality of differently sized edible products 24.

The dosing station 36 can include a pump motor 49 disposed between the reservoir 26 and the dosing heads 46. The dosing station 36 can include a single dosing head 46 or a plurality of dosing heads 46 as desired. The dosing station 36 can include a first conduit 51 that extends from the reservoir 26 to the pump 49, and a second conduit 53 that extends from the pump 49 toward the dosing heads 46. The combination of the first conduit 51, the pump 49, and the second conduit 53 can be referred to as a fluid delivery line 59 that places the reservoir 26 in fluid communication with the dosing head or dosing heads 46. Thus, reference to either of both of the pump 49, the first conduit 51, and the second conduit 53 can apply with equal force and effect to the fluid delivery line 59. Further, unless indicated otherwise, reference to the fluid delivery line 59 can apply to any one or more up to the first conduit 51, the pump 49, and the second conduit 53. The second conduit 53 and the at least one dosing head 46 can combine to collectively define an output line 89 that can receive the API-containing liquid from the pump 49 and deliver the volume of API-containing liquid to the substrate 23. Thus, reference herein to the output line 89 can apply with equal force and effect to either or both of the second conduit 53 and the dosing head 46. It should be appreciated that the diagram shown in FIG. 3B is schematic, and additional or fewer conduits can be included that place the reservoir 26 in fluid communication with each dosing head 46. Further, the dosing head 46 configuration can be modified as desired. For instance, as shown in FIGS. 3B-4, the system 20 can include a single dosing head 46 or a plurality of dosing heads 46 that is in fluid communication with the pump 49 and delivers the API-containing liquid to the underlying substrate 23.

In some examples, either or both of the conduits 51 and 53 can be nonporous and inelastic. In some examples, either or both of the first and second conduits 51 and 53 can be made from poly-ether-ether-ketone (PEEK) tubing. Further, either or both of the first and second conduits 51 and 53 can have any suitable inner diameter as desired. In one example, the inner diameter can be in a range from approximately 10 mils to approximately 30 mils, such as from approximately 10 mils to approximately 20 mils. In some examples, a thermal insulation layer can surround either or both of the conduits 51 and 53. The thermal insulation layer can have an R-value in a range from R3 to R10, or any suitable R-value as desired. In other examples, either or both of the first and second conduits 51 and 53 can have an insulative R-value that is in the range from R3 to R10, or any suitable R-value as desired.

Thus, the pump 49 can direct volumes of the liquid 25 from the reservoir 26 to the dosing heads 46, and out the dosing heads to the substrate 23. When the dosing station 36 includes a plurality of dosing heads 46, the second conduit 53 can extend to a manifold 55. The pump 49 can thus deliver the volume of the liquid 25 to the manifold 55 under a pressure differential, and the manifold 55 can distribute the volume of liquid 25 to the dosing heads 46. In this regard, it should be appreciated that the second conduit 53 is in fluid communication with the dosing heads 46.

The pump 49 can be a pressure pump having a motor that creates a pressure differential in the fluid delivery line 59. In one example, the pump 49 can include a positive displacement motor as described above, also referred to as a positive pressure pump, that creates a positive pressure differential in the fluid delivery line 59. The positive displacement motor can be configured as a stepper motor. The pump 49 can be thus configured as a syringe pump having a stepper motor so as to define a stepper motor-driven syringe pump (SMSP) or any suitable alternative pump as desired. For instance, in other examples, the pump 49 can be configured as a peristaltic pump. As will be described in more detail below, the pressure in the fluid delivery line 59 created by the pump 49 urges successive increments, or incremental quantities, of the API-containing liquid 25 to flow in a direction from the reservoir 26 to an outlet of the dosing head 46, thereby causing the successive increments of the API-containing liquid 25 in the fluid delivery line 59 to flow out of the outlet of the dosing head 46. Once a sufficient quantity of the API-containing liquid 25 has amassed at the tip of the dosing head 46, the API-containing liquid 25 can be expelled from the dosing head 46 that travels from the dosing head 46 to the underlying substrate 23 that is aligned with the dosing head 46.

The present inventors have recognized that the API-containing liquid can be incompressible in both conduits 51 and 53. Therefore, when the second conduit 53 is filled with API-containing liquid, each positive displacement or step of the pump 49 that drives a respective volume of the API-containing liquid 25 into the second conduit also drives the same volume of API-containing liquid to flow out of the dosing head 46, and thus be emitted from the dosing head 46. Surface tension between the API-containing liquid and the dosing head 46 may prevent the API-containing liquid that is emitted out of the dosing head 46 to be delivered to the substrate 23 until a critical mass of API-containing liquid has been driven out the dosing head 46 that overcomes the surface tension. Once the critical mass of API-containing liquid has been driven out the dosing head 46, continuous steps of the motor deliver respective volumes of the API-containing liquid 53 into the second conduit, which in turn drives the respective volumes of \the API-containing liquid to be emitted out of the dosing head 46 and delivered to the substrate 23. The API-containing liquid can be delivered to the substrate 23 in the form of a continuous stream, an intermittent stream, or individualized successive droplets. The motor can perform a number of steps that drives a total volume of API-containing liquid that contains the substantially predetermined dosage of API into the second conduit 53. As will be described in more detail below, a total initial volume of the total volume of the API-containing liquid, which contains a primary dosage of API, travels from the dosing head 46 to the substrate 23. When the API-containing liquid is delivered to the substrate 23 as a continuous stream, the continuous stream can deliver substantially the primary dosage of API. When a residual volume of API-containing liquid remains adhered to the dosing head 46, a wash station can deliver a wash that causes substantially all the residual API-containing liquid that has been emitted out of the dosing head 46 but not yet delivered to the substrate 23 to be delivered to the substrate 23. Accordingly, a total displacement of the pump 49 defined by a sum of the displacement of each of the performed steps of the motor can define the volume of API-containing liquid that is delivered to the substrate 23. The pump 49 thus can perform a predetermined total displacement of API-containing liquid to deliver a predetermined dosage of the API to the underlying substrate.

Thus, the present inventors have recognized that a predetermined volume of API-containing liquid can be delivered to the underlying substrate that is not dependent on the volume of drops delivered to the substrate, as in conventional systems. Conventional systems that rely on a predetermined number of drops to deliver a desired volume of API, on the other hand, deliver a total volume of API-containing liquid having a delivery resolution that is limited by the volume of API-containing liquid in each drop. That is, volume increments of API-containing liquid that is delivered to the substrate by conventional systems are limited to the volume of API-containing liquid in each of the whole drops. While drop-based systems are suitable for some applications, the present system 20 relies on the total volume displacement of the pump 49 as opposed to a quantity of drops to determine the total volume of API-containing liquid that is driven to the substrate. Thus, the dosage accuracy of API delivered to the substrate 23 of the present system 20 can be independent of drop formation. The present system 20 is configured to deliver a total volume of API-containing liquid to the substrate 23 having a higher dosing resolution than conventional drop-based systems. In particular, the volume of API-containing liquid can be delivered to the substrate in incremental volumes that each are defined by respective individual displacements, such as steps, that are performed by the motor. The respective volume of API-containing liquid that is driven by each individual displacement is less than the volume of a given drop in conventional commercial systems. In some examples, the present system 20 is configured to emit a volume of API-containing liquid that travels to the substrate 23 that contains the substantially predetermined dosage of API As will be appreciated from the description below, when the pump 49 performs a number of displacements that equates to a volume of API-containing liquid, a first portion of the volume will be delivered to the substrate 23 from the dosing head. The first portion of the volume can be referred to as total initial volume of the API-containing liquid. A second portion of the volume, also referred to as a residual volume, can remain adhered to the dosing head. As will be described in more detail below, a wash can be delivered to the dosing head that causes the residual volume to be delivered to the underlying substrate. Therefore, because the API-containing liquid is incompressible, the total volume of API-containing liquid is equal to the volume of API that is advanced by the pump 49.

In some examples, referring now to FIG. 3A-3B, when the system 20 includes a plurality of dosing heads 46 in communication with the pump 49, the dosing heads can deliver to the substrate 23 respective portions of the volume of API-containing liquid that is driven into the second conduit 53 by the pump 49. The respective portions can be substantially equal to each other in some examples. Alternatively, the different dosing heads 46 can be configured to deliver different quantities of the respective volume of liquid 25 to the edible product 24. Further, some of the dosing heads 46 can be in communication with different pumps 49 that deliver different API-containing liquids 25. Therefore, the API-containing liquid 25 delivered by a first at least one dosing head 46 can include a different active pharmaceutical agent than the liquid 25 delivered by a second at least one dosing head 46. Further still, the system 20 can be configured to deliver any number of API-containing liquids 25 each containing a different pharmaceutical agent to a respective at least one dosing head 46. Accordingly, the dosing heads 46 can combine to deliver active different pharmaceutical agents in different quantities onto a common substrate 23. Alternatively or additionally, the different liquids can have different concentrations of their respective active pharmaceutical agent. The system 20 can therefore include any number of reservoirs 26 as desired, each reservoir containing a different liquids that contains a different at least one active pharmaceutical ingredient. The different liquids can be delivered to different respective ones of the dosing heads 46. Thus, different dosing heads can be configured to deliver different APIs to the substrate.

As one example, a first group of dosing heads 46 can be configured to deliver a dose of a first active pharmaceutical agent, and a second group of dosing heads 46 can be configured to deliver a dose of a second active pharmaceutical agent, wherein the second active pharmaceutical agent is different than the first active pharmaceutical agent. Further, the first active pharmaceutical agent can be delivered in a different predetermined approximate dose than the second active pharmaceutical agent. Further still, the reservoir containing the first API-containing liquid can be maintained at a different temperature than a second reservoir that contains the second API-containing liquid. Thus, the viscosity of each of the respective API-containing liquids 25 can be individually controlled. Additionally, the temperature of one or more up to all of the respective conduits 51 and 53 and at the respective dosing heads 46 can be different so as to individually control the viscosity of each liquid as it travels from the respective reservoir to the respective one or more dosing heads 46.

The system 20 can include a controller 57 (see also FIG. 9) that operates a stored program to control the pump 49. The controller can include a processor that operates the stored program, and any suitable human-machine interface (HMI) having a data input device such as a keyboard, and a data display device, such as a monitor. In some example, all steps performed by the controller 57 described herein can be according to the stored program and/or can be performed according to user input data. If desired, the controller 57 can also verify that the predetermined volume of API-containing liquid has been delivered to the underlying substrate 23.

Referring to FIGS. 3A-4, the system 20 can be configured to deliver heat to the liquid 25 either in one or more of the conduits and/or in the dosing head 46 and prior to or during dispensing of the API containing liquid to the substrate 23. The heat can be sufficient to decrease the viscosity of the API-containing liquid 25. In some examples, for instance when the API-containing liquid 25 includes a solvent, the step of delivering heat to the liquid 25 can cause the solvent to evaporate, such that pure API having a sufficiently low viscosity is dispensed from the dosing heads 46. Thus, in one example, the API-containing liquid 25 can include the API and solvent, and can travel from the reservoir 26 to the dosing head 46. The API-containing liquid 25 can be heated between the reservoir 26 and the dosing head 46 to decrease the viscosity of the liquid 25 and, in some instances, evaporate some or all of the solvent. Alternatively or additionally, the API-containing liquid 25 can be heated at the dosing head 46 so as to decrease the viscosity of the liquid 25 and, in some instances, evaporate some or all of the solvent. In one example, the system 20 can include at least one heater that delivers heat to one or more up to all of the first conduit 51, the second conduit 53, the pump 49, the manifold 55 if present, and the at least one dosing head 46, so as to decrease the viscosity of the API-containing liquid and, in some instances, evaporate the solvent. In one example, the liquid 25 can be maintained at a temperature in a range from approximately 100 degrees F. to approximately 200 degrees F., such as from approximately 140 degrees F. to approximately 200 degrees F., and in one example from approximately 150 degrees F. to approximately 180 degrees F. Alternatively, in some examples such as when the liquid 25 is a solution, the liquid 25 can be maintained at room temperature.

Further still, while each of the dosing head 46 can be configured to dispense the API-containing liquid 25 that has been received from the reservoir 26, it is recognized that the API-containing liquid 25 can be delivered using other methods. For instance, the system 20 can include a first reservoir that contains the API in liquid or solid form, and a second reservoir that contains a solvent. The API and solvent can mix at the dosing station 36. For instance, the API and solvent can mix at the dosing head 46. In one example, the dosing head can include a first chamber that receives the API, and a second chamber that receives the solvent. The API and solvent can mix in the dosing head 46 to produce a solution having the predetermined concentration of API. The solution produced in the dosing head 46 can then be delivered to the substrate 23 in the manner described herein. In some examples, the concentration can be varied inside the dosing head 46. That is, the respective proportions of API and solvent that are mixed in the dosing head 46 can be varied. Further, the API or the solution can be mixed with at least one other ingestible modifier that is configured to modify at least one of flavor, one or more mechanical properties, or one or more aesthetics of the API. The mixing can occur in the dosing head 46 or at any other location as desired. For instance, the at least one other edible product can be mixed in the liquid 25 in the reservoir 26 in some examples.

Referring again to FIGS. 3A-3B, in one example, the dosing heads 46 can be arranged in an array 48 that includes at least one row 50 of dosing heads 46. The dosing heads 46 of each row 50 can be substantially equidistantly spaced along the respective row 50. Alternatively, the dosing heads 46 can be variably spaced along the respective row 50. The array 48 can further include a plurality of columns 52 that spaces the rows 50 from each other. The dosing heads 46 can be equidistantly spaced along the respective columns 52. Alternatively, the dosing heads 46 can be variably spaced along the respective columns 52. In one example, all of the dosing heads 46 can be configured to deliver the same at least one active pharmaceutical ingredient. Alternatively, as described above, different groups of the dosing heads 46 can be configured to deliver a respective different active pharmaceutical ingredients. Each group can include at least one dosing head 46 up to a plurality of the dosing heads 46. Each group can be defined by a respective one or more of the rows 50. Alternatively, each group can be defined by a respective one of the columns.

The dosing heads 46 can be spaced from each other as desired so as to deliver a desired distribution of the active pharmaceutical ingredient to the edible product 24 in the dosing zone 54. Alternatively, one or more dosing heads 46 can be movable so as to deliver the active pharmaceutical ingredient to multiple locations of the edible product 24. In one example, the dosing heads 46 are configured to deliver a substantially even distribution of the volume of liquid 25 to the edible product 24 in the dosing zone 54. For instance, the respective quantity of the volume of solution dispensed by each of the dosing heads 46 or each plurality of dosing heads can be substantially equal to the respective quantity of solution dispensed by the other dosing heads 46 or other pluralities of dosing heads 46.

In another example, the system 20 can divide the dosing zone 54 into a plurality of subzones. Each subzone can be configured to receive a different at least one active pharmaceutical ingredient. Thus, a first group of at least one dosing head 46 can deliver a first at least one active pharmaceutical ingredient to a first one of the subzones, and a second group of at least one dosing head 46 can deliver a second at least one active pharmaceutical ingredient that is different than the first at least one active pharmaceutical ingredient to a second one of the subzones. Alternatively or additionally, the first group of at least one dosing head 46 can be configured to deliver a first dose of the first at least one active pharmaceutical ingredient, and the second group of at least one dosing head 46 can be configured to deliver a second dose of the second at least one active pharmaceutical ingredient that is different than the first dose. In still another example, the first and second groups of at least one dosing head 46 can be configured to deliver the same at least one active pharmaceutical ingredient, but in different doses. The active pharmaceutical ingredient can be substantially evenly distributed in each of the subzones.

In some examples, at least one dosing head 46 such as a plurality of dosing heads 46 can be movable along the substrate 23 so as to deliver the respective at least one active pharmaceutical ingredient at different locations of the edible product 24. Further, the dosing heads 46 can be configured to deliver different active pharmaceutical ingredients to the substrate 23. For instance, the dosing heads 46 can be configured to deliver different combinations of liquids. In one example, the dosing heads 46 can deliver to the substrate 23 a first liquid that contains a first active pharmaceutical ingredient. Next, the dosing heads 46 can deliver to the substrate 23 a second active pharmaceutical ingredient that is different than the first active pharmaceutical ingredient. Next, the dosing heads 46 can deliver to the substrate 23 a third active pharmaceutical ingredient that is different from each of the first and second active pharmaceutical ingredients, and so forth until all desired active pharmaceutical ingredients have been delivered to the substrate 23.

When the dosing heads 46 are arranged in groups of dosing heads 46 that each deliver a respective different at least one active pharmaceutical ingredient, the different active pharmaceutical ingredients can be delivered to respective different locations of the substrate 20. For instance, the dosing heads 46 can remain stationary with respect to the substrate 23 as the active pharmaceutical ingredient is delivered to the substrate 23. Alternatively, the dosing heads 46 can be movable along the substrate 23, such that the combination of active pharmaceutical ingredients as delivered by different groups of at least one dosing head 46 can be delivered to the same respective location of the substrate 20. The heads 46 can be movable such that the dosing heads 46 can deliver the respective active pharmaceutical ingredient to different respective locations of the substrate 23 than the other dosing heads. The active pharmaceutical ingredients in the different respective locations can be substantially evenly distributed in at least one direction along to the substrate 23. For instance, the active pharmaceutical ingredient in the different locations can be substantially evenly distributed in two perpendicular directions along the substrate 23.

The substrate 23 includes an external surface that defines an inner surface 60 that faces the support surface 30, and an outer surface 58 that is opposite the inner surface 60 and faces the at least one dosing head 46. The dosing heads can deliver the active pharmaceutical ingredient to the outer surface 58 of the substrate 23. The edible product 24 defines a thickness that extends from the inner surface 60 to the outer surface 58. The delivered volume of active pharmaceutical ingredient can substantially remain on the outer surface 58. Delivering the volume of liquid to the outer surface 58 can expose the liquid to oral receptors, thereby increasing speed of ingestion of the active pharmaceutical ingredient. Alternatively or additionally, the delivered volume of liquid 25 can permeate through the outer surface 58 so as to impregnate at least a volume of a thickness of the edible product that extends from the outer surface 58 to the opposed inner surface 60. Alternatively still, the active pharmaceutical ingredient can be injected into the substrate 23 between the inner surface 60 and the outer surface 58. For example, at least 20% of the active pharmaceutical ingredient can be disposed in a middle 75% of the thickness. The middle 75% of the thickness can be equidistantly spaced from each of the inner surface 60 and the outer surface 58. For instance, at least 20% of the active pharmaceutical ingredient can be disposed in a middle 50% of the thickness. The middle 50% of the thickness can be equidistantly spaced from each of the inner surface 60 and the outer surface 58. In some examples, the distribution along the outer surface of the substrate 23 can be different than the distribution along the thickness of the substrate 23 from the outer surface to the inner surface.

In one example, the API-containing liquid is delivered from the dosing heads 46 to the respective at least one target location of the edible product 24 under any suitable force, such as gravitational forces, electrostatic forces, forces applied by the delivery of API-containing liquid from the pump 49 to the second conduit 53, or the like. In another example, the API-containing liquid are delivered from the dosing heads 46 to the respective locations of the edible product under positive pressure. In this regard, the dosing station 36 can control whether the API-containing liquid remains on the outer surface 58 of the edible product 24, and whether the API-containing liquid permeates through the outer surface 58 into the thickness of the edible product 24 in the manner described above. In still other examples, one or more of the dosing heads 46 can be coupled to a respective needle that can be driven into the edible product 24 so as to deliver the respective quantity of the volume of liquid 25 into the edible product 24 at a location between the outer surface 58 and the inner surface 60. In some instances, the needle can be heated at a temperature suitable to soften or melt locations of the substrate contacted by the needle, in order to assist in the injection of the needle into the substrate. The heated needle can also maintain a desired viscosity of the at least one active pharmaceutical ingredient as the active pharmaceutical ingredient is being delivered through the needle and into the substrate. Whether the active pharmaceutical ingredient is delivered to the outer surface of the edible product 24 or as an injection, the active pharmaceutical ingredient can be delivered to the edible product in microquantities if desired.

As described above, the system 20 can include the post-processing station 40 that is configured to process the edible product 24 after the liquid 25 has been delivered to the edible product 24. The post-processing station 40 can be configured to dry the solvent, for instance, when the API is delivered as a solution. In this regard, the post-processing station 40 can include any suitable drying member, such as at least one drying head 70 or a plurality of drying heads 70 that are configured to deliver a drying agent to the respective locations of the edible product 24 so as to dry the liquid 25. It is appreciated that when the liquid 25 dries, the solvent of the delivered volume of liquid 25 that carries the active pharmaceutical ingredient also dries and can evaporate, leaving the active pharmaceutical ingredient on the substrate 23. In this regard, the drying heads 70 can be arranged in an array that has an equal number of rows and columns as the array of dosing heads 46. Further, the relative position of the drying heads 70 with respect to the other drying heads 70 can be the same as the relative position of the dosing heads 46 with respect to the other dosing heads 46. Thus, the drying heads 70 can be aligned with the active pharmaceutical ingredients that were delivered to the edible product 24 by the dosing heads 46.

The drying agent can be configured as any suitable light, including ultraviolet, laser, infrared, or the like. Alternatively, the drying agent can be a forced gas that is delivered to the outer surface of the edible product 24. The forced gas can be air, nitrogen, or any suitable alternative gas such as an inert gas. The forced gas can be heated, and can have a temperature that is in a range for instance from about 100 degrees F. to about 250 degrees F. Alternatively, the forced gas can be substantially unheated, and thus at ambient temperature. Alternatively still, the forced gas can be cooled, and thus at a temperature below ambient temperature. In this regard, the cooled forced gas can cause an API to freeze on the surface of the substrate, or to delay evaporation of the solvent so as to allow the API-containing liquid to further impregnate the thickness of the substrate 23. Alternatively, the post-processing station 40 can expose the dosed substrate to ambient air or a controlled environment so as to dry the volume of liquid 25. It is recognized that the drying agent applied to the API can increase the viscosity of the API. The post-processing station can further cause the API to further adhere to the substrate 23. For instance, increasing the viscosity can cause the API to further adhere to the substrate 23. Further, applying forced air to the substrate 23 can cause the API to disperse along the substrate as the API travels along the outer surface of the substrate 23, thereby facilitating absorption of the API into the substrate 23. For instance, it is recognized that the API can become saturated in the portion of the substrate 23 that underlies the delivered API-containing liquid. Causing the API to move along the outer surface of the substrate 23 then allows the API to absorb into the substrate 23 at locations of the substrate 23 that are not saturated with the API. The post-processing station 40 can further cause the API to solidify on or in the substrate 23. In some examples, the API can crystallize on or in the substrate 23. Alternatively, the API can remain as an oil on or in the substrate 23.

It is appreciated that energy can be applied to the substrate 23 to improve diffusion or absorption of the API into the substrate 23. For instance, when heat is applied to the surface of certain substrates 23, and in particular certain edible food products, such as chocolate, baked goods, gummy candy, lollipop, and the like, the temperature of the surface of the edible product be raised to a level whereby the edible product melts, sweats, or otherwise assumes a form that is configured to encapsulate the API. The temperature can be increased, for instance, by directing at least one of heated forced air and a light to the surface.

Once the substrate 23 has been post-processed, the active-containing edible product 24 can be transferred from the post-processing station 40 to the packing station 42. At the packaging station 42, the dried edible products 24 can be individually wrapped in any suitable package 73. Alternatively or additionally, a plurality of the active-containing edible products 24 can be wrapped in a common package. The active-containing edible product 24 can include a cooked edible product, and a dose of an active pharmaceutical ingredient carried by the cooked edible product in the dosing zone of the cooked edible product. The dose of the active pharmaceutical ingredient can be substantially evenly distributed in the dosing zone. Because the edible product was fully cooked prior to adding the active pharmaceutical ingredient, the active pharmaceutical ingredient need not be cooked after the active pharmaceutical ingredient was added.

The controller 57 can be in communication with any and all components of the system 20 over a data communication bus 115 (see FIG. 9) or over any suitable alternative data communication system. The system 20 can include a load cell that determines, by sensing weight, that the substrate 23 is in alignment with the dosing head 46. The load cell can further determine that the volume of API-containing liquid has been delivered to the substrate 23. Alternatively still, the system 20 can include a detector that outputs a signal, such as a voltage or an image, to verify that the substrate 23 is in alignment with the dosing head 46.

The controller 57, and thus the dosing system 20, can further ensure that the total API dosage delivered to the substrate 23 is substantially equal to a predetermined or planned API dosage that is to be delivered to the substrate 23. During operation, the pump 49 can be configured to incrementally deliver respective volumes of the API-containing liquid into the second conduit 53 in multiple sequential steps. The successive steps cause the API-containing liquid 25 to flow out of the outlet of the dosing head 46 in respective successive incremental volumes of API-containing liquid. As the increments of the API-containing liquid 25 flow out of the dosing head outlet, the increments of API-containing liquid 25 can amass amassed on the dosing head 46. Once a sufficient quantity or volume of the API-containing liquid has amassed to overcome the surface tension between the API-containing liquid and the dosing head 46, the API-containing liquid is delivered from the dosing head 46 to the substrate 23. Thus, the steps can cause the API-containing liquid 25 to be delivered from the dosing head 46 to the underlying aligned substrate 23.

Once a sufficient volume of the API-containing liquid has amassed, the volume of API-containing liquid introduced into the conduit as continued steps of the motor are performed can cause the API-containing liquid to be emitted from the dosing head 46 to the substrate 23, for instance as a stream. The stream can be a continuous stream or an intermittent stream as desired. For instance, a continuous stream can be emitted until the total initial volume of the API-containing liquid has been delivered to the substrate. Alternatively, a plurality of intermittent stream segments of the intermittent stream can be emitted until the total initial volume of the API-containing liquid has been delivered to the substrate. During the time duration between the delivery of successive intermittent stream segments, the liquid carrier of a previous intermittent stream segment can at least partially or substantially entirely evaporate prior to the delivery of a subsequent intermittent stream segment. The intermittent stream segments can be defined by pauses of the positive displacement of the motor during a dosing operation. Alternatively, the intermittent stream segments can be defined by surface tension between the dosing head 46 and the API-containing liquid during a dosing operation.

As will be described in more detail below, it is recognized that after the total initial volume of the API-containing liquid has been delivered to the substrate 23, a residual volume of the API-containing liquid, and thus a residual API, can remain adhered to the dosing head 46. The total initial volume of API-containing liquid plus the residual volume of the API-containing liquid substantially equals the total volume of API-containing liquid delivered from the pump 49 to the second conduit 53 when the second conduit 53 is substantially filled with API-containing liquid. Thus, a first or initial portion, quantity, or volume of API in the first or initial portion, quantity, or volume of the API-containing liquid that exits the outlet of the dosing head 46 can be delivered to the substrate 23 as delivered API.

A second or residual portion, quantity, or volume of the API that is disposed in a second or residual portion, quantity, or volume of the API-containing liquid exits the outlet of the dosing head 46 can remain adhered to the dosing head 46 as residual API. The residual API can be defined both by 1) adhered residual API that remains adhered to a surface of the dosing head 46 after the delivery of the total initial volume of API-containing liquid 23, and 2) a residual API in a remainder bolus of residual API-containing liquid that has is disposed at the dosing head 46, for instance, at the outlet or tip, that 1) was not delivered to the substrate with the initial volume of API-containing liquid, and 2) is insufficiently large to be delivered to the substrate 23, and that has not been delivered with the total initial volume of API-containing liquid. Thus, the remainder bolus can be referred to as an incomplete quantity or volume of API-containing liquid that is not sufficiently large to overcome surface tension with the dosing head 46 and travel to the substrate 23. The remainder bolus can thus separate from the initial volume as the initial volume travels to the substrate 23. The separation can occur, for instance, when the desired number of steps are performed by the motor, and the motor discontinues performing additional steps.

The dosing system 20 is configured to cause substantially all residual API to be delivered to the underlying substrate during an API dosing operation. Thus, the actual API dosage that is delivered to the substrate 23, which includes the total initial API in the total initial volume of API-containing liquid, and the residual API in the residual volume of API-containing liquid, is substantially equal to the predetermined or planned API dosage to be delivered to the substrate.

Figure 7C:
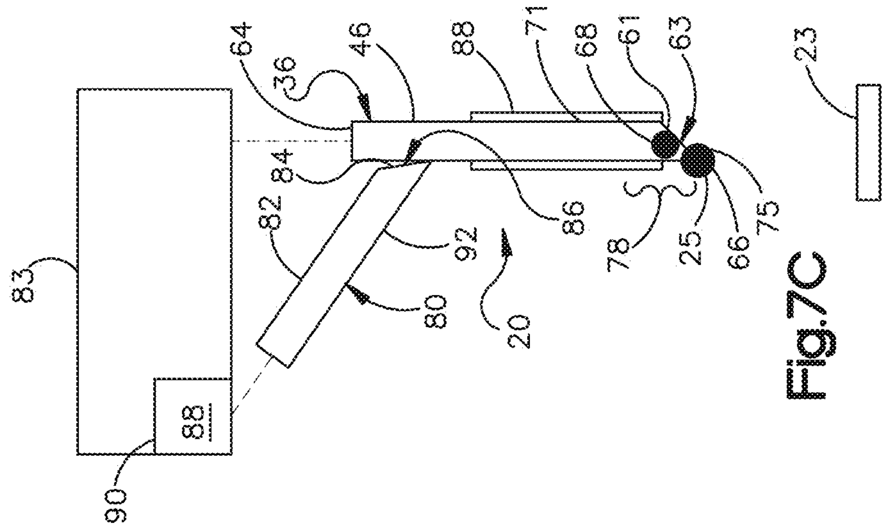
FIG. 7C shows the schematic side view of FIG. 7B, but showing residual API adhered to a dosing head, and a wash station that delivers a wash fluid to the dosing head.
Figure 7B:
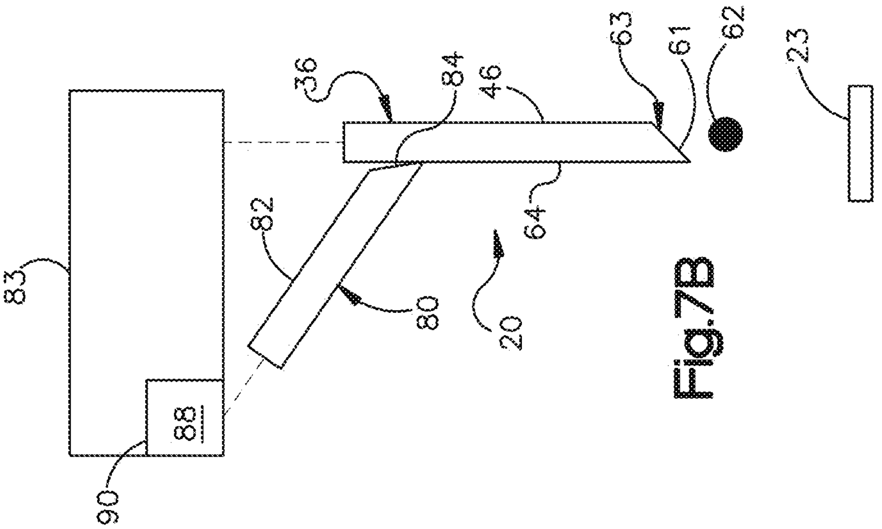
FIG. 7B shows the schematic side view of FIG. 7A, but showing the droplet being delivered to the substrate.
Figure 7A:
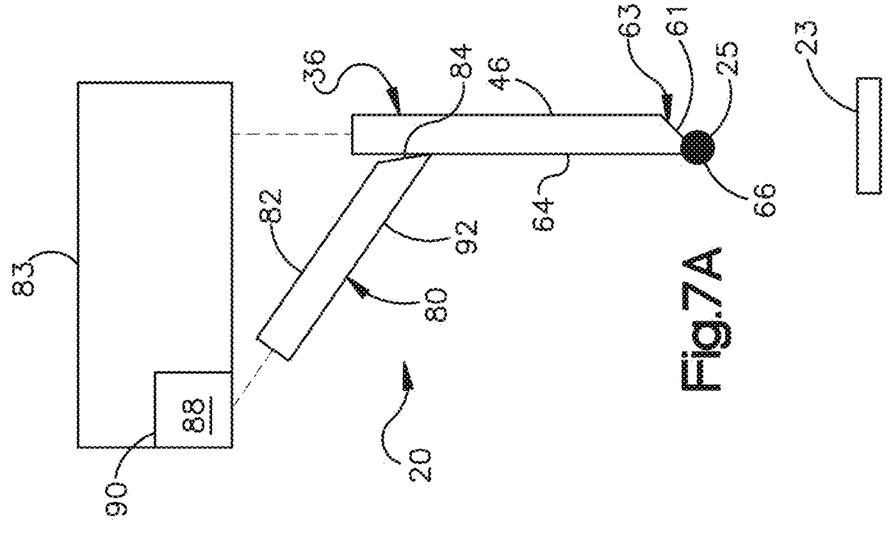
FIG. 7A is a schematic side view of a portion of a dosing system constructed in accordance with one example, showing the formation of a droplet to be dosed from a dosing head to a substrate.

Referring now to FIGS. 3B, 4, and 7A, the pump 49 is configured to perform successive incremental steps that correspondingly drives API-containing liquid into the second conduit in a forward direction toward the outlet of the dosing head 46. The dosing head 46 can be a separate structure of the second conduit 53, or can be defined by the conduit. In one example, the dosing head 46 can be defined by a nozzle or tip 61. The tip 61 has an internal surface that defines an outlet 63 through which the API-containing liquid 25 is configured to be expelled toward the underlying substrate 23, and an external surface opposite the internal surface. In one example, the dosing head 46 can be configured as a dosing needle 64. Thus, the tip 61 can define a dosing needle tip. However, the tip 61 can be defined by any suitable alternative delivery structure such as a nozzle and the like. Therefore, reference herein to the dosing head 46, needle 64, nozzle, or other like structure can refer with equal force and effect to all others of the dosing head 46, needle 64, nozzle and other like structure having an outlet 63 suitable to for the delivery of API-containing liquid, unless otherwise indicated. Thus, it should be appreciated that any suitable dosing head can be used. During operation, the API-containing liquid 25 can flow through the outlet 63 so as to be delivered to the underlying substrate 23. The dosing needle 64 can be a metal such as stainless steel, titanium, or any alloy thereof, or a polymer such as Teflon, poly-ether-ether-ketone (PEEK), perfluoroalkoxy (PFA), or any suitable alternative metal or plastic or alternative material. The tip 61 can be configured as a bevel tip as shown in FIGS. 7A-7D. Thus, the tip can extend in a direction that is oblique with respect to the direction of travel of the API-containing liquid from the dosing head 46 to the substrate 23. It should be appreciated, of course, that the tip 61 can have alternative shapes, such as a flat tip shown in FIG. 7E or any suitable alternative shape as desired. The flat tip, which can also be referred to as a blunt tip, can be oriented in a plane that is perpendicular to the direction of travel of the API-containing liquid form the dosing head 46 to the substrate 23. In one example, the flat tip can be oriented along a horizontal plane. The tip can define any suitable configuration as desired. For instance, in one example, the dosing head 46 can include one or more orifices that are configured to deliver the API-containing liquid in the form of a spray when the API-containing liquid travels through the dosing head 46. The one or more orifices can have a crimped shape or any suitable alternative shape that produces a spray. The spray can be configured so that a substantial entirety of the API-containing liquid that is emitted as a spray is delivered to the substrate.

The travel of the API-containing liquid 25 in the fluid delivery line 59 further causes the incremental quantities of API-containing liquid 25 to flow out of the outlet 63 of the dosing head 46 during operation of the pump 49. The volumes of the API-containing liquid that have been emitted out of the outlet of the dosing head 46 during operation of the pump 49 can form a bolus 66 of API-containing liquid 25 that amasses at the tip 61 of the dosing head 46. The bolus 66 adheres to the tip 61 under retention forces such as surface tension. The API-containing liquid 25 that is included in the bolus 66 can be said to be expelled from the outlet of the dosing head 46, but not yet in sufficiently large quantity to overcome the surface tension with the dosing head 46, for instance at the tip 61, to travel from the dosing head 46 to the substrate 23.

Thus, the bolus 66 remains adhered or suspended at the tip 61 of the dosing head 46 under forces such as surface tension. Subsequent steps of the motor cause respective incremental quantities of the API-containing liquid 25 to be added to the bolus 66. Thus, the quantity of API-containing liquid is incrementally added to the bolus as step are sequentially performed by the pump motor. As quantities of the API-containing liquid are incrementally added to the bolus, the bolus grows in size. Referring also to FIG. 7B, once the bolus 66 has grown to a size that is sufficiently large to overcome surface tension and other forces that cause the bolus to be suspended at the tip 61 of the dosing head 46, the bolus 66 exits the tip 61 of the dosing head 46 as an initial volume of API-containing liquid that travels to the substrate 23 in the manner described above.

When the initial volume is configured as a microdroplet 62, subsequent successive incremental advancements of the API-containing liquid 25 in out the outlet of the dosing head 46, thereby creating respective subsequent boluses 66 that grow to form respective subsequent droplets. In one example, gravitational forces can cause the droplets to be expelled from the tip of the dosing head 46. In other examples, external forces can be applied to the bolus that causes the bolus to be expelled from the tip of the dosing head 46 and delivered to the underlying substrate 23. In other examples, after an initial bolus 66 has been formed, continuous operation of the pump 49 can drive a continuous or intermittent stream of API-containing liquid to be emitted out of the dosing head 46, and in particular out of the outlet 63 after the initial bolus 66 has formed.

It should be appreciated that the dosing head 46 can be configured in any suitable alternative manner as desired. For instance, referring now to FIG. 7G, the dosing head 46 can define more than one dosing surface, such as a pair of dosing surfaces 67. While dosing surfaces 67 are shown as being defined by a respective pair of dosing nozzles, which can be defined by needles 61 in some examples, it should be appreciated that the dosing surfaces 67 can alternatively be defined by a single needle as desired. During operation of the pump 49, the API-containing liquid can travel through the outlets 63 of the needles 61 and onto the dosing surfaces 67.

The dosing surfaces 67 can be sloped and face away from each other. For instance, the dosing surfaces 67 can be sloped equal and opposite each other. The dosing surfaces 67 can be straight and linear. In one example, the dosing surfaces 67 can converge as they extend in the direction of travel of the API-containing liquid. The dosing surfaces 67 can further be disposed on opposite sides of a central axis 74. The central axis 74 can extend equidistantly from the dosing surfaces 67. Thus, the dosing surfaces 67 can be symmetrical with each other about the central axis 74. The central axis 74 can be straight and linear, and can be oriented parallel to gravitational forces.

During operation, the central axis 74 can be selectively aligned with one or more target dosing locations of the substrate 23. As the API-containing liquid travels along the dosing surfaces 67 they travel toward the central axis. The dosing surfaces 67 can be spaced from the substrate. For instance, the dosing surfaces 67 can be positioned above the substrate 23. It is envisioned that respective volumes the API-containing liquid traveling along the dosing surfaces 67 can merge and combine prior to traveling to the substrate 23. For instance, the respective volumes can flow along the dosing surfaces, and eventually off of the dosing surfaces into free space where they travel under gravitational forces to the substrate 32. The respective volumes can combine after they flow off the dosing surfaces 67 so as to define a combined volume 77 of API-containing liquid.

The combined volumes 77 can be formed, for instance, while the respective volumes are traveling in free space. In other examples, the dosing surfaces 67 can merge, such that the respective volumes combine to define the combined volume 77 before they flow off the dosing surfaces 67. The respective volumes can combine into the combined volume 77 substantially at the central axis, such that the combined volume 77 travels to the substrate 23 substantially along the central axis 74. Further, the respective volumes of API-containing liquid can be substantially equal to each other. The respective volumes can be delivered to the dosing surfaces 67 until the predetermined volume of API-containing liquid has been delivered to the dosing surfaces 67, and thus to the substrate 23. The predetermined volume can include respective first portions of API-containing liquid to travel along the dosing surfaces 67 and to the substrate 23, thereby delivering a first portion of the API to be delivered to the substrate. The predetermined volume can further include respective second residual portions of the API-containing liquid that remain adhered to the dosing head 46, including the dosing surfaces 67, which are delivered to the substrate during wash operation that delivers residual API to the substrate 23 as described in more detail below.

In one example, each of the steps of the pump motor can drive the same volume of API-containing liquid 25 incrementally into the conduit 53, and thus can drive the same volume toward and to the tip or outlet of the dosing head 46. Thus, a predetermined or planned total API dosage to be delivered to the substrate can be readily determined. In particular, the concentration (by weight and/or by volume) of API in the API-containing liquid 25 is known. Further, each incremental quantity of API-containing liquid 25 that is driven out of the outlet 63 by each successive step of the motor of the pump 49 is known. Therefore, the predetermined or planned total quantity (which can be a mass or a volume) of API that is to be driven out of the tip 61 is the product of the number of incremental advancements of the API-containing liquid 25, which can also be the number of steps performed by the pump motor, and the incremental quantity of API contained in each incremental quantity of API-containing liquid 25 that is driven out of the outlet 63. It is appreciated that the incremental quantity of API-containing liquid 25 of each increment can be substantially equal to each other. Accordingly, a planned total number of increments of the API-containing liquid can be selected to deliver a predetermined or planned total API dosage to the underlying substrate 23. The number of increments of the API-containing liquid 25 can be delivered by a corresponding number of steps performed by the stepped pump motor, or other alternative motor that can drive the API-containing fluid 25 incrementally in the manner described herein.

Each step of the pump 49 can cause an incremental advancement of any volume of API-containing liquid as desired. In one example, each step can cause an incremental advancement of a volume in a range from approximately 0.01 nanoliters to 100 approximately nanoliters, such as from approximately 0.1 nanoliters to approximately 50 nanoliters, such as from approximately 0.5 nanoliters to approximately 50 nanoliters, such as from approximately 1 nanoliter to approximately 10 nanoliters. In one specific example, each step of the pump 49 can cause an incremental advancement of 1.2 nanoliters of API-containing liquid. The performance of any number of steps of the pump 49 as desired can deliver a desired predetermined dose of API to the substrate, as described in more detail below.

In one example, the dosing system 20, and in particular the controller 57, can adjust the number of steps of the pump per dose depending on the temperature of the API-containing liquid. In particular, it is recognized that as the temperature of the API-containing liquid increases, the volume of the API-containing liquid expands. However, the API dosage per unit volume of API-containing liquid remains unchanged. Therefore, a reduced quantity of API in the API-containing liquid is incrementally advanced in the fluid delivery line 59 during the performance of each step of the pump 49 when the temperature of API-containing liquid increases. A correspondingly greater volume of API-containing liquid can therefore be delivered to the substrate to deliver the desired dosage of API to the substrate 23 to compensate for the increased temperature. Conversely, as the temperature of the API-containing liquid decreases, an increased quantity of API is incrementally advanced during the performance of each step of the pump 49. A correspondingly reduced volume of API-containing liquid can therefore be delivered to the substrate to deliver the desired dosage of API to the substrate 23 to compensate for the decreased temperature. Thus, based on the measured temperature of the API-containing liquid, the pump can be instructed to perform a greater number of steps during instances of increasing temperature, or a fewer number of steps during instances of decreasing temperature, to ensure that the desired quantity of API is incrementally advanced with the API-containing liquid.

As described above, the dosing system 20 can be configured to ensure that the planned or predetermined total API dosage is substantially equal to the total delivered API dosage that is actually delivered to the substrate 23. As will now be described, the total initial API dosage can be a sum of a total initial API dosage that is delivered to the substrate 23, and a total residual API dosage. When the API-containing liquid is delivered to the substrate 23 as droplets, such as microdroplets 62, the total initial API dosage can be referred to as a total droplet API dosage. However, the total initial API dosage also refers to API that was delivered in a continuous or intermittent stream, unless otherwise indicated.

Referring now to FIG. 7C, the total residual API dosage 78 can include two components of residual API, as will now be described. It should be appreciated that the residual API-containing liquid to be delivered to the underlying substrate 23 can be partially defined by a bolus 66 of the API-containing liquid 25 at the tip 61, in the manner described above. Some of the API-containing liquid of bolus 66 can wick along an external surface 71 of the dosing head 46 at a location adjacent the tip 61 under surface tension forces, and adhere to the external surface 71, thereby defining a residual quantity 68 of API. In particular, while the API-containing liquid 25 that travels from the dosing head to the substrate travels out of the dosing head along a forward or downward direction, residual API-containing liquid can wick up the external surface 71 of the dosing needle 64 in a rearward or upward direction. The external surface 71 can be defined by an external side wall of the dosing needle 64. As API-containing liquid is added to the bolus 66 during operation of the pump 49, the bolus 66 grows in size. When the bolus 66 becomes sufficiently large to overcome surface tension and other retention forces, the bolus 66 is delivered to the substrate 23.

Continuous operation of the pump 49 can cause a continuous or intermittent stream of the API-containing liquid that is then delivered to the substrate 23. Alternatively, the API-containing liquid can be delivered in the form of droplets. The present inventors have discovered that the residual quantity 68 of API from the boluses 66 and from the stream and/or droplet can remain adhered to the external side wall of the needle 64. This residual quantity 68 of API can be referred to as adhered residual API. The adhered residual API 68 that remains adhered to the external surface of the external side wall of the needle 64 is thus not delivered to the substrate 23 with the initial volume of API-containing liquid. Thus, the adhered residual API 68 can define a first component of the total residual API.

Further, as described above and referring to FIG. 7C, a second component of the total residual API can be defined by the API in the residual API-containing liquid 25 that has amassed at the tip of the dosing head 46 as a remainder bolus 75 that is insufficiently large to be delivered to the substrate 23 with the initial volume of API-containing liquid. In this regard, it should be appreciated that the pump 49 can be discontinued when the predetermined number of incremental displacements have been performed, thereby driving out of the dosing head a corresponding volume of API-containing liquid that contains the predetermined dosage of API to be delivered to the substrate 23. Thus, the initial volume of API can be delivered to the substrate 23.

When the initial volume of API-containing liquid is delivered to the substrate 23 in the form of droplets, it is recognized that the predetermined or adjusted volume of API-containing liquid may not be divisible by the volume of API in the droplets that are formed and delivered to the substrate 23. In other words, after a final droplet of the plurality of droplets has been delivered to the substrate 23, a difference can remain between the number of predetermined or planned number of incremental quantities of the API-containing liquid 25 delivered through the dosing head outlet 63, and the actual number of incremental quantities of the API-containing liquid delivered through the dosing head outlet 63. However, the difference may be less than the number of incremental quantities of the API-containing liquid that would be sufficient to form a droplet that is delivered to the substrate 23.

Thus, a final number of subsequent increments of the API-containing liquid 25 can continue to travel out of the outlet 63 of the dosing head 46 during operation of the pump motor until an entirety of the predetermined or planned number of incremental advancements of the API-containing liquid 25 have traveled out of the outlet 63. The present inventors have recognized that the API-containing liquid 25 of the final number of increments can have a mass that is insufficient to be delivered to the substrate 23. Thus, the API-containing liquid 25 of the final number of increments can remain adhered or suspended at the tip 61 as a remainder bolus 75 of API-containing liquid 25. The total residual API can be defined by the adhered residual API 68 and the API in the remainder bolus 75. The total residual API can also define a total residual API dosage.

In other examples whereby the initial volume of API-containing liquid is delivered to the substrate 23 in the form of a continuous or intermittent stream, when operation of the motor is discontinued, the initial volume of API-containing liquid can separate from a remainder bolus 75 as it travels to the substrate 23. The remainder bolus 75 thus remains on the dosing head 46 without having been delivered to the substrate 23.

With continuing reference to FIG. 7C, the dosing system 20 can include a wash station 80 that is configured to perform a wash operation that removes substantially all of the total residual API from the dosing head 46 and deliver substantially all of the total residual API from the dosing head 46 to the underlying substrate 23. The wash station 80 can include wash conduit 82 having a wash tip 84 that defines a wash outlet 86. The wash conduit 82 can be supported such that the wash conduit tip 84 is supported relative to the dosing head 46. For instance, the wash conduit 82 can be fixedly supported relative to the dosing head 46. In one example, the wash conduit 82 can be supported by a common support structure 83 that also supports the dosing head 46.

In one example, the wash conduit tip 84 can be disposed against and in contact with the external surface of the dosing head 46, and in particular the dosing nozzle or needle 64. For instance, the wash conduit tip 84 can be in contact with the external surface of the dosing head 46 at a location spaced above an adhesion region where the adhered residual API 68 adheres. The wash conduit 82 can receive wash fluid 88 from a wash fluid tank 90, and dispense the wash fluid 88 to the external surface of the dosing head 46, such as the dosing needle 64. As will be described in more detail below, the wash fluid 88 is configured to flush, or remove, substantially all of the total residual API from the dosing needle 64, and deliver the removed total residual API to the underlying substrate 23 that is aligned with the dosing needle 64. The wash fluid tank 90 can be supported by the support structure 83 or externally supported as desired.

In one example, the wash conduit 82 can be configured as a wash needle 92. Thus, the tip 84 can define a wash needle tip. The wash needle 92 can be a metal such as stainless steel, titanium, or any alloy thereof, or a polymer such as Teflon, poly-ether-ether-ketone (PEEK), perfluoroalkoxy (PFA), or any suitable alternative metal or plastic or alternative material. The tip 84 can be configured as a bevel tip as shown in FIG. 7C. It should be appreciated, of course, that the tip 84 can have alternative shapes, such as a flat tip shown with respect to the dosing needle in FIG. 7E, or any suitable alternative shape. The wash needle 92 can be oriented such that an input end of the wash needle 92 that receives the wash fluid 88 from the wash fluid tank 90 is disposed above the wash outlet 86. Further, the wash needle 92 can be oriented such that the central axis of the wash needle 92 is at an oblique angle relative to the dosing needle 64. Thus, the wash outlet 86 can be directed at the external surface of the dosing needle. The wash station 80 can include a wash pump, such as a syringe pump configured as described above with respect to the pump 49. Thus, the wash pump is configured to incrementally advance the wash fluid into and out of the wash needle 92 and the wash outlet 86.

The velocity of the wash fluid flow out of the wash needle 92 can be controlled by the speed of the wash pump operation.

Figure 7D:
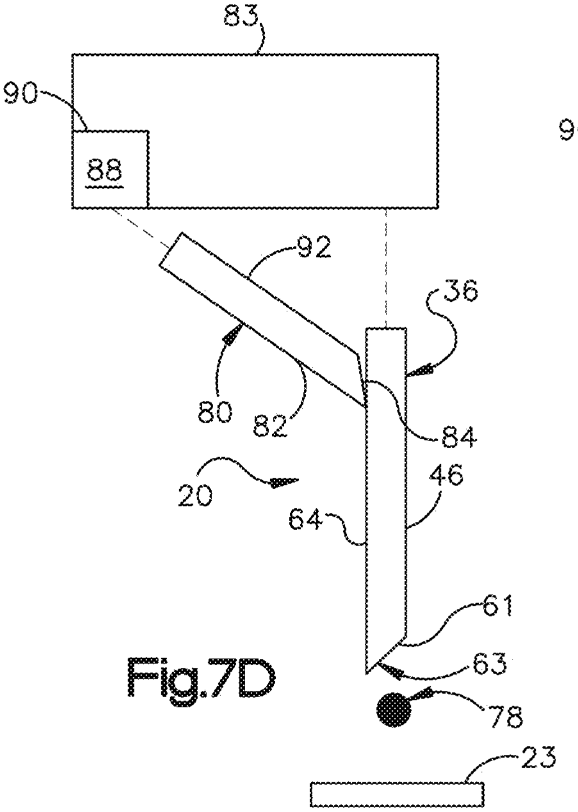
FIG. 7D shows the schematic side view of FIG. 7C, but showing the residual API being delivered to the substrate.
Figure 7E:
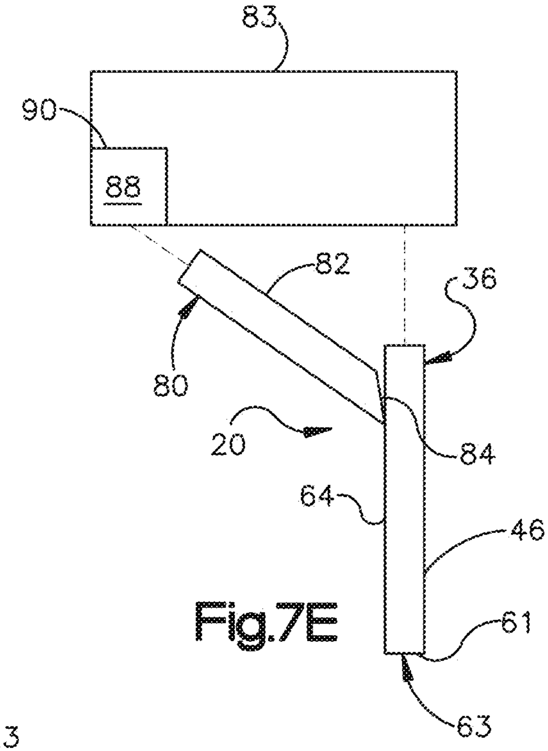
FIG. 7E shows the schematic side view of FIG. 7A, but showing the dosing head having a flat tip in one example.

During operation, the controller 57 can control the delivery of the wash fluid to the dosing head 46, and in particular to the external surface of the dosing head 46. The wash fluid 88 can be delivered as a flow from the wash fluid tank 90 to the wash needle 92, and out of the wash outlet 86 in any manner as desired. For instance, the wash pump can induce a pressure that causes the wash fluid 88 to flow out of the wash outlet 86 at any suitable velocity as desired. In this regard, it should be appreciated that the wash pump can control both the volume of the wash fluid 88 and the velocity of the wash fluid 88 that exits the wash outlet 86. The wash fluid 88 flows out of the wash outlet 86 and onto the external surface of the dosing needle 64. The wash needle tip 84 can direct the wash fluid to the external surface of the dosing needle 64. The wash fluid 88 then travels along the external surface of the dosing needle 64 under gravitational forces. Surface tension between the wash fluid 88 and the external surface of the dosing needle 64, and a sufficient flow rate of the wash fluid 88 out of the wash outlet 86, causes the wash fluid to travel about an entirety of the perimeter of the external surface of the dosing needle 64. As the wash fluid 88 travels along the external surface of the wash needle toward the dosing needle tip 61, the wash fluid 88 travels through the adhesion region, where it contacts the adhered residual API 68, and causes substantially all of the adhered residual API 68 to become removed. In one mode of operation, the adhered residual API 68 can become dislodged from the external surface of the dosing needle 64. Alternatively or additionally, the adhered residual API 68 can be dissolved in the wash fluid 88, albeit non-homogenously. The volume of wash fluid 88 sufficient to remove the adhered residual API 68 can depend on factors such as the material composition of the API and the dosing needle, the diameter of the dosing needle, and the volume of API being dosed, among others. In some examples, a single drop of the wash fluid 88 can be sufficient. In other examples, multiple drops or a continuous or intermittent stream of the wash fluid 88 is used. Once the adhered residual API 68 is removed from the external surface of the dosing needle, the removed residual API 68 free of the dosing head 46 can travel under gravitational forces to the underlying substrate 23. In one example, as shown in FIG. 7D, the removed residual API 68 can travel with the wash fluid 88 under gravitational forces to the underlying substrate 23. Thus, the removed residual API 68 is dosed to the substrate 23.

Figure 7F:
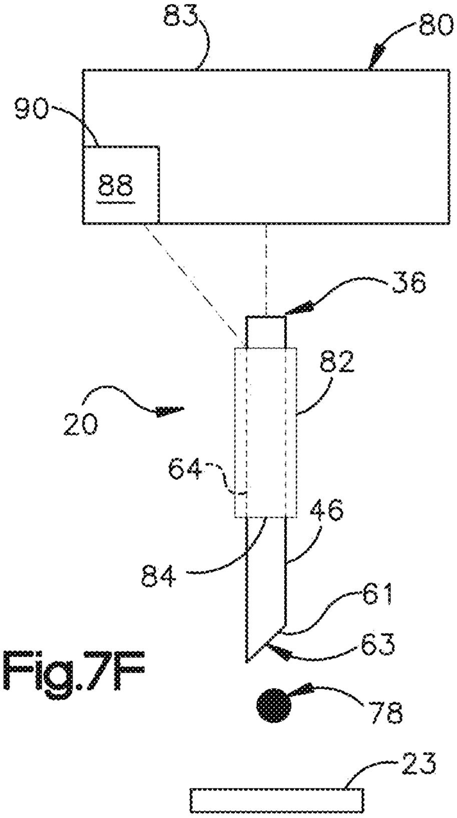
FIG. 7F shows the schematic side view of FIG. 7A, but showing the wash station configured in accordance with another example.
Figure 7G:
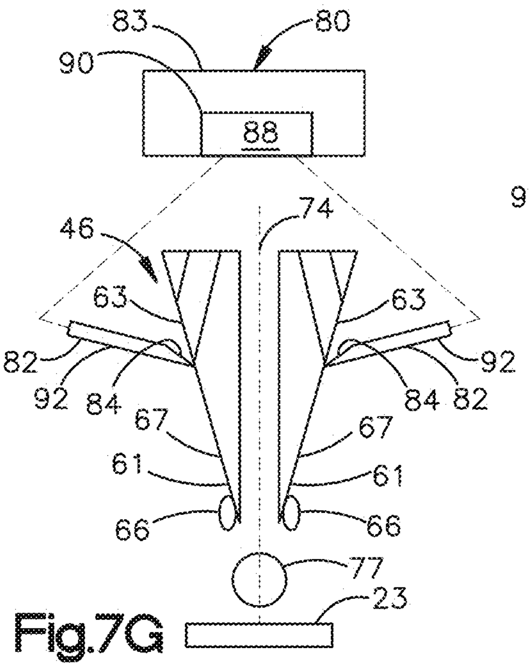
FIG. 7G shows the schematic side view similar to FIG. 7A, but showing the dosing head having opposed sloped dosing surfaces in one example.

The wash fluid 88 continues to travel along the external surface of the dosing needle 64 to the dosing needle tip 61. The wash fluid 88 thus contacts the remainder bolus 75, and causes the remainder bolus 75 to separate from the dosing head 46, and in particular from the dosing needle 64. Specifically, the wash fluid 88 removes the remainder bolus 75 from the tip of the dosing needle 64, or any alternative location of the dosing head to which the remainder bolus 75 is attached. The remainder bolus 75, free from the dosing head 46, thus travels under gravitational forces to the underlying substrate 23. In one example, as shown in FIG. 7D, the remainder bolus 75 travels with the wash fluid 88 under gravitational forces to the underlying substrate 23. It is thus appreciated that the substrate 23 is dosed with the total residual API. Further, the removed residual API 68 can combine with the remainder bolus 75 as they travel to the substrate 23, or can remain separate. It should be appreciated that the wash fluid can be directed to the residual API 68 and the reminder bolus 75 in accordance with any suitable dosing head configuration as desired. For instance, the wash fluid 88 can be directed to each of the dosing surfaces 67 along respective wash conduits 82 as shown in FIG. 7F to remove any residual quantity of API-containing liquid as well as a remainder bolus 75 from either or both of the dosing surfaces 67.

As described above, surface tension between the wash fluid 88 and the external surface of the dosing needle 64, and a sufficient flow rate of the wash fluid 88 out of the wash outlet 86, can cause the wash fluid to travel about an entirety of the perimeter of the external surface of the dosing needle 64. Accordingly, any residual API can be dislodged by the wash fluid and delivered to the substrate. Alternatively, referring now to FIG. 7F, the outlet 86 of the wash station can surround at least a portion of the external surface dosing head. For instance, the outlet 86 can be configured as an annulus that surrounds an entirety of the outer perimeter defined by the external surface of the dosing head. The annulus can be configured as a ring or can have any suitable alternative shape as desired. In one example, the annulus can be concentrically arranged about the dosing head. During operation, the outlet 86 can deliver the wash fluid to multiple sides of the external surface of the dosing head to remove the residual API and deliver the total residual API to the substrate 23 in the manner described above. In one example, the outlet 86 can deliver the wash fluid to an entire outer perimeter of the dosing head to remove the residual API and deliver the residual API to the substrate. Thus, the wash fluid can define a continuous path about an entire perimeter of the external surface of the dosing head. In one example, the dosing head 46 and the wash conduit 82 can be integrated into a single unitary structure having an inner lumen defined by the dosing head 46, and an outer lumen defined by the wash conduit 82 that surrounds the inner lumen. Alternatively, the dosing head 46 and the wash conduit 82 can be defined by separate structures.

In some examples, controlling the flow direction of the API-containing liquid in the dosing head can assist in separating the remainder bolus 75 from the API-containing liquid that is intended to be delivered to a subsequent substrate. In this regard, it is recognized that the pump 49 can perform steps in a forward direction so as to advance the API-containing liquid in a forward direction out the dosing head. The pump 49 can also be reversible so as to cause the API-containing fluid to travel in the delivery line 59 in a or rearward direction away from the dosing head 46 and toward the pump 49. In particular, the pump 49 can perform steps in a rearward direction so as to drive the API-containing liquid to flow in the reverse direction away from the dosing head. Reverse operation of the pump 49 can cause API-containing liquid to flow into the reservoir 26. Alternatively, if it is desired to dispose of the API-containing liquid, for instance if it is suspected or determined that the API-containing liquid in the delivery line is defective, the API-containing liquid in the delivery line 59 can be diverted and redirected out of the delivery line 59 to a refuse container prior to flowing into the reservoir 26 during reverse operation of the pump 49. The API-containing liquid in the delivery line 59 can be diverted and redirected to the refuse container at a position downstream of the pump 49, between the pump and the reservoir 26, at the outlet of the tank, or between the pump 49 and the dosing head 46 as desired. After completion of the dosage displacement conducted by the pump 49, which in turn delivers substantially the predetermined dosage of API to the substrate, the controller can command the pump to perform a reverse pump step to decouple the remainder bolus from the stream of API-containing liquid in the output line 89, and then actuate a wash to deliver both adhered residual API and the remainder bolus to the same substrate.

During operation, when the wash fluid 88 is applied to the dosing head to remove the remainder bolus 75, the pump 49 can operate in the reverse direction, which in turn can cause the API-containing liquid in the dosing head 46 to move in a rearward direction away from the dosing head 46 and into the second conduit 53. The movement of the API-containing liquid in the rearward direction can create separation forces that assist in separating the remainder bolus 75 from the API-containing liquid in the dosing head upon application of the wash fluid 88. Once the remainder bolus 75 has been separated and delivered to the substrate, the pump 49 can perform the same number of steps in the forward direction that were performed in the rearward direction, thereby advancing the API-containing liquid in the dosing head to the same location as it was prior to operation of the pump 49 in the rearward direction.

In one example, the wash fluid 88 can be delivered to the dosing needle 64 after the predetermined volume of API-containing liquid to be delivered to the substrate 23 has been displaced by the pump 49, which can be referred to as a dosage displacement. It is understood that during normal operation, the amount of API-containing liquid displaced by the pump 49 is emitted out of the dosing head, and is thus either delivered to the substrate or defines the remainder bolus. Therefore, the wash fluid 88 can be delivered to the dosing needle 64 after the pump 49 has completed the dosage displacement.

In some examples, for instance when the API-containing liquid is delivered to the substrate 23 in the form of droplets, the wash fluid 88 can be delivered to the dosing needle 64 after a final droplet of the droplets of API-containing liquid have been delivered to the substrate 23. In other examples, for instance when the API-containing liquid is delivered to the substrate 23 in the form of a continuous or intermittent stream, the wash fluid can be delivered once an entirety of the initial volume of API-containing liquid has been delivered. Thus, in both examples whereby the API-containing liquid is delivered in the form of droplets and whereby the API-containing liquid is delivered in the form of a stream, the wash fluid can be delivered once the predetermined number of volume displacements of the motor have been performed to deliver the predetermined dosage of API to the substrate 23. In some examples, the wash fluid 88 can be delivered to the dosing head 46 only after the predetermined number of volume displacements of the motor have been performed. In other examples, the wash fluid 88 can be delivered to the dosing head 46 when it is determined that a threshold quantity of residual API is adhered to the dosing head. Thus, the wash fluid 88 can be delivered to the dosing head both before and after the predetermined number of volume displacements of the motor have been performed.

It should thus be appreciated that the wash fluid 88 can be a liquid, such as an alcohol. For instance, the alcohol can be ethanol or any suitable alternative alcohol. In this regard, it will be appreciated that the wash fluid 88 can be the same liquid as the solvent in the API-containing liquid 25, when the API-containing liquid is a solution. Alternatively still, the wash fluid 88 can be any suitable liquid as desired that is configured to dislodge the adhered residual API and the remainder bolus 75 from the dosing needle 64. Any volume of wash fluid 88 can be applied to the external surface of the dosing needle 64 as desired, such that the volume of wash fluid 88 is sufficient to dislodge the residual API from the dosing needle 64. In one example, the volume of wash fluid 88 can be delivered as a wash drop. In some examples, when the API-containing liquid is delivered to the substrate 23 as droplets, the volume of the wash drop is no greater than the cumulative volume of each of the droplets. In other examples, the volume of the wash fluid 88 can be less than 20%, such as less than 10%, such as less than 5%, such as less than 3%, such as approximately 1% of the predetermined volume of the API-containing liquid that contains the dosage of API delivered to the substrate 23. In some examples, the wash fluid 88 can be heated to a temperature greater than ambient temperature prior to delivery of the wash fluid 88. The increased temperature of the wash fluid 88 can cause the wash fluid 88 to more effectively remove the residual API. Alternatively or additionally, the wash needle 92 can be heated to a desired temperature greater than ambient temperature to thereby heat the wash fluid 88 as it exits the wash needle 92. It is recognized that after the wash fluid 88 has travelled to the substrate 23, the wash fluid 88 can evaporate in the manner described herein with respect to the liquid carrier of the API-containing liquid, leaving the total residual API remaining on the substrate 23.

It is therefore appreciated that substantially all of the API-containing liquid 25 that is incrementally advanced by the pump 49 during a dosage displacement, and thus substantially all of the API in the API-containing liquid 25 that has been incrementally advanced by the pump 49, can be delivered to the substrate 23. The controller 57 can thus track, or determine, the total delivered API dosage delivered to the substrate 23. Otherwise stated, instructing the pump motor to perform the predetermined or planned number of steps to produce the predetermined number of incremental advancements of the API-containing liquid can cause substantially all of the predetermined or planned API quantity or dosage to be delivered to the substrate 23, both directly out of the dosing head, and as residual API. It should be noted that the system 20 is configured to deliver substantially all of the predetermined or planned API dosage to the substrate 23 without relying on imaging and analysis of droplets that travel from the dosing head 46 to the underlying substrate 23, as is the case with certain conventional dosing systems. In particular, the dosage of API delivered to the substrate is the product of the concentration of API in the API-containing liquid, the quantity (volume or mass) of API-containing liquid 25 that is incrementally advanced in each incremental advancement of the API-containing liquid 25, and the number of incremental advancements of the API-containing liquid. The number of incremental advancements of the API-containing liquid can be defined by the number of steps performed by the pump motor when the pump motor is a stepper motor. Further, because the planned API dosage can be determined based on the planned number of incremental volumetric advancements of the API-containing liquid 25, the planned API dosage can be determined without calculating a planned number of droplets to be delivered to the substrate 23. Further, because the total delivered API dosage delivered to the substrate 23 can be determined based on the number of incremental advancements of the API-containing liquid 25 performed by the pump 49, the total API dosage can be determined without determining the number of droplets delivered to the substrate 23.

Figure 7H:
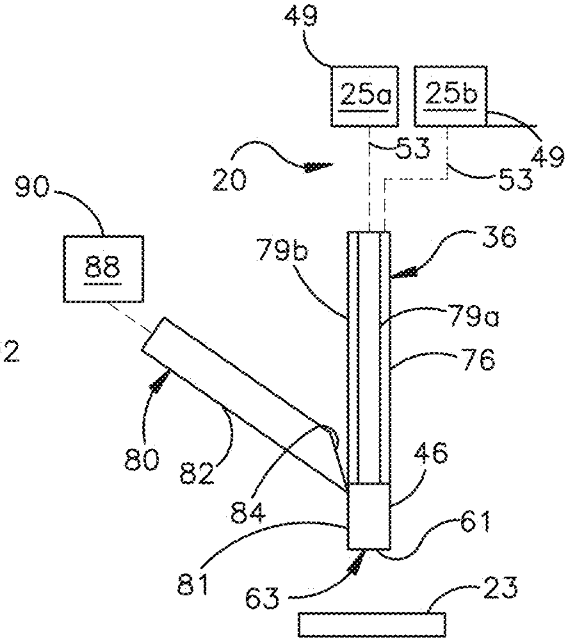
FIG. 7H shows the schematic side view similar to FIG. 7A, but showing the dosing head having concentric dosing tips in another example.

Referring now to FIG. 7H, it should be appreciated that the system 20 can be configured to dose more than one API-containing liquid to the substrate 32. In one example, a second pump 49 that is connected to a second reservoir 26 containing a second API-containing liquid can be delivered to the substrate. In another example shown in FIG. 7H, the system 20 can include a plurality of pumps 49 that each deliverers a respective API-containing liquid to the substrate 23 in the manner described herein. For instance, a first pump 49 can deliver a first API-containing liquid 25*a*, and a second pump 49 can deliver a second API-containing liquid 25*b* to the substrate 23.

In one example, the dosing station 36 can include a cannula 76 that defines multiple delivery lumens that each contains a respective API-containing liquid. For instance, the cannula 76 can define a first delivery lumen 79*a* and a second delivery lumen 79*b*. The first and second delivery lumens 79*a* and 79*b* can be disposed adjacent each other. In one example, the second delivery lumen 79*b* can surround the first delivery lumen 79*a*. For instance, the second delivery lumen 79*b* can be concentrically arranged about the first delivery lumen 79*a*. The second delivery lumen 79*b* can thus be referred to as an outer lumen, and the first delivery lumen 79*a* can be referred to as an inner lumen. In other examples, the first and second delivery lumens can be arranged side-by-side. It should be appreciated that each lumen can have its own inline pressure sensor, or a combined flow cell can sense the merged stream at the outlet as desired.

The first delivery lumen 79 *a* can receive a first API-containing liquid 25 *a* from a first pump 49, and deliver the first API-containing liquid 25*a* to the substrate 23 through a respective first dosing conduit 53. The second delivery lumen 79*b* can receive a second API-containing liquid 25*b* from a second pump 49, and deliver the second API-containing liquid 25*b* to the substrate 23 through a respective second dosing conduit 53 that is separate from the first dosing conduit. In one example, the first and second API-containing liquids 25*a* and 25*b* can include the same API. For instance, the first and second API-containing liquids 25*a* and 25*b* can be in the form of different liquids, such as a solution, suspension, mixture, emulsion, or any suitable alternative liquid. In other examples, the first and second API-containing liquids 25*a* and 25*b* can include different APIs. The delivery lumens 79*a* and 79*b* can isolate the API-containing liquids 25*a-b* from each other.

As shown at FIG. 7H, the delivery lumens 79 *a* and 79 *b* can terminate at a dosing head 46. When first and second API-containing liquids 25*a-b* flow into the combined dosing head 81, the first and second API-containing liquids 25*a-b* can be combined to define a combined API-containing liquid. Thus, the dosing head 46 can be referred to as a combined dosing head 81, which in some examples can define a combined nozzle. The combined liquid can then be travel from outlet 63 at the tip 61 of the combined dosing head 81 to the substrate 23 in the manner described herein.

After each of the pumps 49 have caused the respective predetermined volumes of API-containing liquids 25*a* and 25*b* to flow into the combined dosing head 81, the wash fluid 88 can be directed to the combined dosing head 81 to remove the adhered residual API defined by the combined API-containing liquid (and thus defined by the first and second API-containing liquids 25*a* and 25*b*), along with any remainder bolus that may remain from the combined API-containing liquid (and thus defined by the first and second API-containing liquids 25*a* and 25*b*), in the manner described herein. In one example, the wash conduit 82 can deliver the wash fluid 88 to one or more sides of the combined dosing head 81 in the manner described herein. Thus, the wash conduit 82 can be disposed adjacent at least one of the delivery lumens. In some examples, the outlet 86 of the wash conduit 82 can surround either or both of the cannula 76 (such as the second lumen 79*b*) and the combined dosing head 81 in the manner described herein. For instance, the cannula 76 can define the outlet 86 that surrounds the second delivery lumen 79*b*.

Figure 7I:
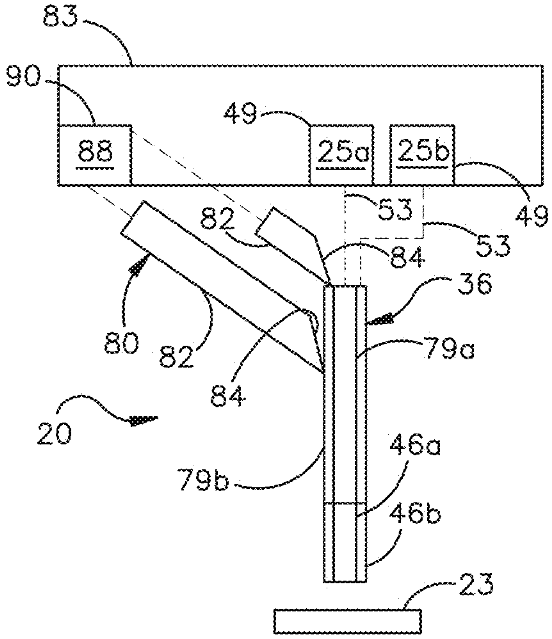
FIG. 7I shows the schematic side view similar to FIG. 7H, but a wash station including dedicated wash conduits configured to deliver a wash fluid 88 to a respective one of the conduits.

In other examples, referring to FIG. 7I, the delivery lumens 79*a* and 79*b* can terminate at respective first and second dosing heads 46*a* and 46*b* that can each be configured as described herein. The delivery lumens 79*a* and 79*b* and the dosing heads 46*a* and 46*b* can isolate the first API-containing liquid 25*a* to the second API-containing liquid 25*b*. Thus, when the first and second API-containing liquids 25*a-b* flow into the respective dosing heads 46*a* and 46*b*, the first and second API-containing liquids 25*a-b* can travel separately to the substrate 23 until the respective predetermined volumes have been delivered to the substrate 23. In some examples, the first and second API-containing liquids can be delivered to separate locations of the substrate 23 and remain separated. In other examples, the first and second API-containing liquids can be delivered to the same location of the substrate 23 whereby the can combine. The wash station 80 can include first and second wash conduits 82 that can deliver the wash fluid 88 to the first and second dosing heads 46*a* and 46*b*, respectively, in the manner described herein.

It is recognized that the substrates to be dosed can be arranged on a tray or other support structure. When the substrates on a given support structure have been dosed, the support structure can be removed, and a new support structure with substrates to be dosed can be delivered to the dosing machine. Alternatively, a new substrate supported by the same support structure can be brought into alignment with the dosing head. In order to prevent the API from drying in dosing head while transitioning from a prior support structure whose substrates have been dosed to a new support structure having substrates to be dosed, the system 20 can enter an idle mode. During the idle mode, the dosing machine can continue operating the pump to continue the flow of the API-containing liquid through the dosing machine. In this manner, the conduits containing the API-containing liquid can be prevented from drying out and/or clogging while transitioning from the prior support structure to the new support structure. Idle mode thus can maintain the throughput of the dosing machine and reduce maintenance. During idle mode, the API-containing liquid can be pumped at the same pace at which it is pumped while dosing the substrate or at a slower pace as desired. To the extent that any API-containing liquid is dispensed during idle mode, the dispensed API-containing liquid can be captured in any suitable refuse container.

Figure 8B:
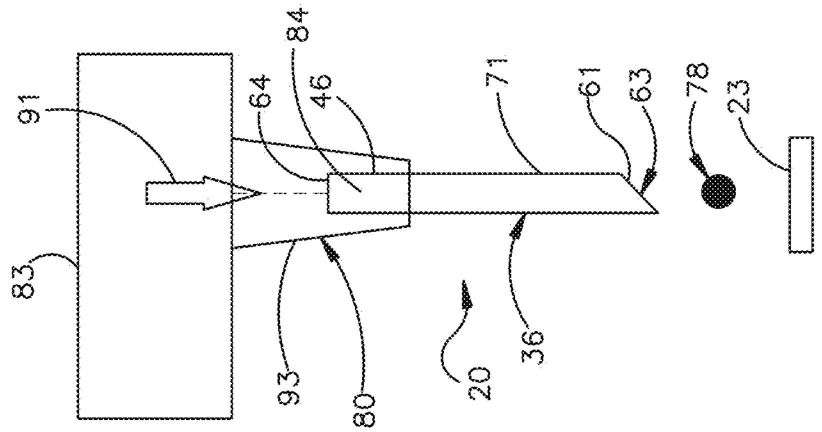
FIG. 8B shows the schematic side view of FIG. 8A, but showing the residual API being delivered to the substrate.
Figure 8A:
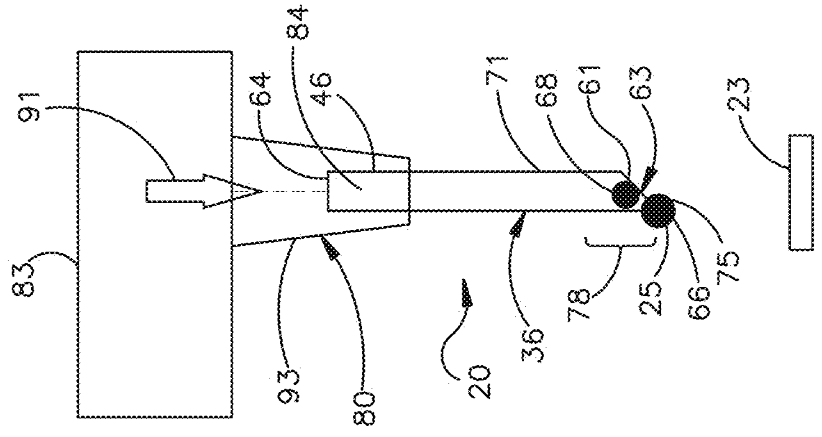
FIG. 8A shows a schematic side view of a portion of a dosing system constructed in accordance with another example, showing residual API adhered to a dosing head, and a wash fluid configured as a gas configured to remove the residual API.

Referring now to FIGS. 8A-8B, while the wash fluid 88 can be a liquid as described above, it is appreciated in other examples, that the wash fluid 88 can be a pressurized gas 91. In particular, the wash station 80 can be configured to deliver the pressurized gas 91 to the external surface 71 and the residual API dosage 78 to remove the residual API dosage 78 from the external surface 71. In one example, the wash station 80 can include a pressurized gas nozzle 93, and the pressurized gas 91 can travel through the nozzle to increase the velocity of the gas 91 as it travels to the residual API dosage 78 and the external surface 71. The velocity of the pressurized gas 91 can be sufficient to remove the residual API dosage 78 and cause the residual API dosage 78 to travel to the underlying substrate. In one example, the nozzle 93 can be oriented coaxially with the dosing needle. Thus, the pressurized gas 91 can travel in a direction coaxial with the dosing needle. It should be appreciated, however, that the pressurized gas 91 can travel in any direction as desired. The pressurized gas can be oxygen, nitrogen, air, or any suitable alternative gas as desired.

It is appreciated that once the desired volume of API-containing liquid 25, and corresponding dose of API, has been delivered to the substrate 23 aligned with the dosing head 46, the substrate 23 can be removed from alignment with the dosing head 46, and subsequent substrate 23 can be brought into alignment dosed in the manner described above. Once the subsequent substrate 23 has been dosed, the subsequent substrate 23 can be removed from alignment with the dosing head 46, and a new subsequent substrate 23 can be brought into alignment dosed in the manner described above. This process can continue until a desired predetermined number of substrates 23 (on the order of thousands or more) have received substantially the desired predetermined volume of API-containing liquid 25, and thus substantially the predetermined desired dose of API, in the manner described above. Thus, the system 20 can be used to perform a batch production method for dosing substrates 23 that are individually and sequentially aligned with the dosing head 46 with an accurate, repeatable predetermined dosage of API.

It should be appreciated that substantially the predetermined dosage of API is delivered to the substrate 23 to produce a dosed substrate. In contrast to conventional excipients used in common oral dosage forms, in which the excipients have less than 1 calorie, the substrate 23 can have a caloric value of at least 1 calorie, such as at least 2 calories, such as at least 3 calories, such as at least 4 calories, such as at least 5 calories, such as at least 6 calories, such as at least 7 calories, or more depending on the nature of the food product. For instance, traditional gummy candies have a caloric value greater than 5 calories. If desired, the dosed substrate can include conventional excipients, but in reduced quantities with respect to conventional pharmaceutical dosage forms. For instance, while up to 90% by weight or volume of conventional pharmaceutical dosage forms can be defined by excipients, the dosed substrate of the present disclosure can include less than approximately 50% of excipient by weight or volume, such as less than approximately 40% of excipient by weight or volume, such as less than approximately 30% of excipient by weight or volume, such as less than approximately 20% of excipient by weight or volume, such as less than approximately 10% of excipient by weight or volume, such as less than approximately 5% of excipient by weight or volume.

Figure 9:
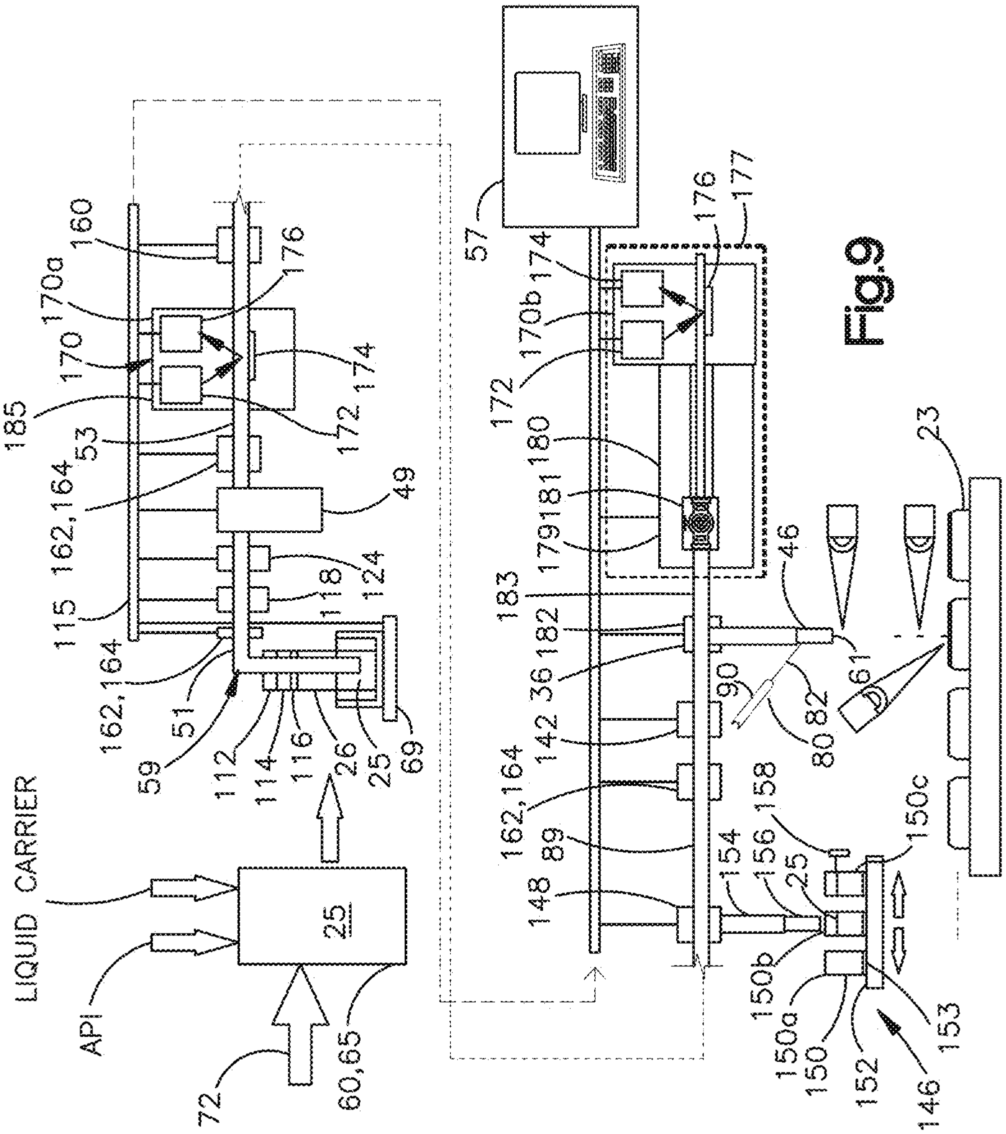
FIG. 9 is another schematic view of a dosing system.

The system 20 will now be further described with initial reference to FIG. 9. In particular, the system 20 can include a number of features that allows the controller 57 to ensure that the system 20 runs properly, and to identify error conditions, thereby ensuring that a predetermined dosage of API is delivered accurately and repeatably to the underlying substrates as they are brought into alignment with the dosing head 46. The controller 57 can be in communication with any and all components of the system 20 over a data communication bus 115 or any suitable alternative data communication system as desired. The system 20 can include the reservoir 26, the first conduit 51 that places the reservoir 26 in fluid communication with the pump 49, and the second conduit 53 that places the pump 49 in fluid communication with the dosing head 46. The first conduit 51 can therefore be referred to as a supply conduit. The second conduit 53 can be referred to as a dosing conduit. One or more up to all components of the system 20 can be manufactured using conventional technology. Alternatively, one or more up to all of the components of the system 20 can be fabricated using MEMS technology as desired.

Figure 10:
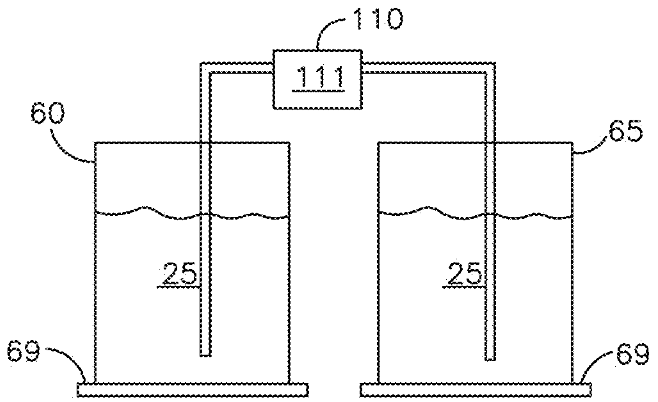
FIG. 10 is a schematic view showing a debubbler removing bubbles from API-containing liquid.

Referring now to FIG. 10, in one example, the API-containing liquid 25 can be produced in any suitable container 60. In particular, as shown at FIG. 9, the API and the liquid carrier can be delivered to the container 60 at a desired predetermined API concentration, thereby producing the API-containing liquid. The system 20 can further stir, sonicate, and/or add heat to the liquid carrier to promote solubility of the API in the liquid carrier during production of the API-containing liquid. Further, it is recognized that the solubility of some APIs may be partially dependent on the pH of the solvent. Accordingly, when the liquid-containing API is a solution and the solute includes an API that is sensitive to the pH of the solvent, the pH of the API-containing liquid 25 can be measured. An acid or base can be added to the API-containing liquid to correspondingly increase or reduce the pH of the API-containing liquid to a desired level to promote solubility of the API while producing the API-containing liquid. After the API-containing liquid has been produced, the API-containing liquid 25 can then transferred to the reservoir 26, via a delivery conduit, via a pouring operation, or by any suitable form of transfer from the container 60 to the reservoir 26.

The system 20 can further include a debubbler 110 that is configured to remove bubbles that may have been produced during production of the API-containing liquid 25. The debubbler 110 can remove bubbles that may form in the API-containing liquid 25 in the container 113 upon production of the API-containing liquid 25. As understood by one having ordinary skill in the art, the debubbler 110 can include a vacuum chamber 111 that receives the API-containing liquid 25 from the container 60 to remove gaseous bubbles from the API-containing liquid 25 and produce a debubbled API-containing liquid. The debubbler 110 can then deliver the debubbled API-containing liquid to the container 60 for subsequent delivery to the reservoir 26, or can deliver the debubbled API-containing liquid to a separate delivery container 65 for subsequent delivery to the reservoir 26 in the manner described above.

It should be appreciated that the system 20 can further be configured to measure the concentration of API in the API-containing liquid 25 after the API-containing liquid has been debubbled by the debubbler 110 using any suitable method and apparatus appreciated by one having ordinary skill in the art. For instance, a calibrated spectrometer, interferometer, or high-performance liquid chromatography (HPLC) can be used to determine the concentration of API in the debubbled API-containing liquid in the manner described in more detail below. It should be appreciated, of course, that any suitable alternative method and apparatus for determining the concentration of API in the API-containing liquid can be used. Additional API or liquid carrier can be added to the API-containing liquid 25 if the concentration is lower or greater, respectively, than desired. The API-containing liquid 25 can again be debubbled, if desired, prior to delivering the API-containing liquid 25 to the reservoir 26.

Referring again to FIG. 9, it is recognized that it may be desired to minimize or eliminate the presence of ambient oxygen-containing air from the reservoir 26, thereby reducing or preventing oxidation of the API-containing liquid 25 disposed in the reservoir 26, which can extend the shelf life of the API-containing liquid disposed in the reservoir 26. As described above, the reservoir 26 contains a supply of the API containing liquid 25 that is delivered to the pump 49. The reservoir 26 can include a cover 112 that can encapsulate the reservoir 26. The reservoir 26 thus can define a head space 114 defined between the level of the API-containing liquid 25 in the reservoir 26 and the cover 112. The system 20 can insert an inert gas backfill into the reservoir 26 so as to drive previous gas, which can include oxygen-containing ambient air, from the reservoir 26. In one example, the inert gas can be nitrogen. Alternatively or additionally, the reservoir 26 can include a septum 116 that is disposed on the API-containing liquid 25 in the reservoir 26. The septum 116 can float on top of the API-containing liquid 25 in the reservoir 26, and can isolate the API-containing liquid 25 from ambient air disposed in the head space 114 with respect to fluid communication.

The system 20 can further be configured to confirm a property of interest of the API-containing liquid in the reservoir 26. Thus, the system can confirm that the API-containing liquid 25 is suitable for delivery to the pump 49, and ultimately for delivery to the substrate 23. It is appreciated that operation of the pump causes a quantity of API-containing liquid to be delivered to the second conduit 53, which can also be referred to as a dosing conduit. When the second conduit 53 and dosing head 46 are full with API-containing liquid, the volume of API-containing liquid that is pumped from the pump 49 to the second conduit 53 is equal to the volume of API-containing liquid that is delivered from the dosing head 46 to the substrate 23. If either or both of the second conduit 53 and the pump 49 are not full with API-containing liquid, creating a head space in either or both of the second conduit 53 and the pump 49) then the volume of API-containing liquid to be delivered to the substrate 23 is the volume of API-containing liquid pumped into the second conduit 53 plus the cumulative head space in the second conduit 53 and the dosing head 46 that does not contain API-containing liquid, in addition to the volume of any API-containing liquid that is delivered to any offline stations of the system 20, such as a validation station 146 and an HPLC station 177 that can include a high performance liquid chromatography (HPLC) device 181, as described in more detail below with reference to FIG. 9.

In one example, the property of interest can be a concentration of the API in the API-containing liquid 25. Thus, the system 20 can confirm the concentration of API in the API-containing liquid 25 in the container 60, 65 prior to delivering the API-containing liquid 25 to the reservoir 26. In this regard, it is appreciated that the container 60 has a larger volume than the reservoir 26, and as a result quantities of API-containing liquid can be stored for lengthy durations of time in the container 60, 65 prior to delivering a quantity of the API-containing liquid 25 to the reservoir 26. It can be desired to ensure that the concentration of the API in the API-containing liquid has not changed in the output line, for instance due to evaporation, precipitation, phase separation, or the like. One method of determining the concentration of API in the API-containing liquid in the container 60, 65 is to weigh the container 60, 65 using any suitable scale 69 to determine a first or initial mass of the API-containing liquid 15 disposed in the container at an initial time that can be defined as being upon completion of producing the API-containing liquid and/or debubbling the API-containing liquid. After the expiration of a duration of time from the initial time, the container can be again weighed to determine a second mass of the API-containing liquid. The first mass can be compared to the second mass to determine whether some of the liquid carrier has evaporated, thereby increasing the concentration of API in the API-containing liquid.

If the second mass is substantially equal to the first mass, for instance within 0.1%), it can be determined that the concentration of API in the API-containing liquid has not changed due to evaporation since production of the API-containing liquid. The API-containing liquid can then be delivered to the reservoir 26. If the second mass is less than the first mass, it can be concluded that evaporation of the API-containing liquid has taken place. As a result, a second concentration of API in the API-containing liquid at the second time is greater than an initial or first concentration of API in the API-containing liquid at the initial time when the API-containing liquid was produced. In this situation, additional liquid carrier can be added to the container to arrive at the first mass, and thus the first concentration of API in the API-containing liquid, prior to transferring the API-containing liquid to the reservoir 26. Alternatively, the API-containing liquid at the higher API concentration can be delivered to the reservoir 26, and the system 20 can deliver a correspondingly reduced volume of API-containing liquid to the substrate 23 to deliver the predetermined dosage of API to the substrate 23. If desired, the API-containing liquid in the container can be debubbled immediately prior to determining the second mass. It should be appreciated that the above-described method of weighing the API-containing liquid can also be performed at the reservoir 26 to determine whether any API-containing liquid 25 has evaporated from the reservoir 26 from the initial time when the API-containing liquid 25 has been transferred to the reservoir 26 to a second time when a quantity of API-containing liquid 25 is to be delivered from the reservoir 26 to the pump 49. The amount of liquid carrier in the reservoir 26 can be increased, or a reduced quantity of API-containing liquid can be delivered from the reservoir 26 to the substrate 23 as desired, as described above. It is understood that the measured masses can be determined by subtracting the known mass of the container or tank from the measured masses.

As an alternative to the method of weighing, or in addition to the method of weighing, the system 20 can determine if the concentration of API in the API-containing liquid in the container and/or tank has decreased using any suitable sensor 72. In one example, the sensor 72 can be an optical sensor configured as a UV-Vis (ultraviolet-visible) spectrometer or interferometer, which can also be referred to herein as a UV-Vis device. During operation, a sample of the API-containing liquid in the container and/or tank can be directed into a flow cell of the UV-Vis device. In one example, the UV-Vis device can emit UV light and visible light to the flow cell to measure the frequency or frequencies at which the light is absorbed by the molecules of the sample disposed in the flow cell. The UV-Vis device can output a spectrum that shows that frequencies at which the light is absorbed. Based on known absorption frequency or frequencies of the molecules in the API-containing liquid, the molecules of the API-containing liquid can be identified on the spectrum. Further, the concentrations of each of the molecules of the API-containing liquid can be determined based on the absorption frequency or frequencies of each of the molecules. Thus, the concentration of the API in the liquid carrier can be determined at different points in time, for instance continuously in real-time, to determine whether the concentration has changed over time. If the absorption frequency or frequencies of the API is unknown, the system can include an HPLC that can receive the API-containing liquid and provide an identification of the molecules and their respective absorption frequencies in the manner described below.

In other examples, a first index of refraction of the API-containing liquid, and a subsequent second index of refraction of the API-containing liquid, can be determined, for example, by directing a spectrometer or an interferometer at the API-containing liquid in the container and/or tank. The first index of refraction and the second index of refraction can be compared to each other to determine whether a quantity of the liquid carrier has evaporated, thereby increasing the concentration of API in the API-containing liquid. If the first index of refraction substantially equals the second index of refraction, it can be determined that the concentration of API in the API-containing liquid has not changed from the initial time to the second time. A difference between the first index of refraction and the second index of refraction can indicate that evaporation of a quantity of the liquid carrier or some other circumstances have caused the concentration of API in the API-containing liquid to change.

In one example, the first index of refraction can be compared to a reference index of refractions of the API-containing liquid, such as a lookup table, to confirm whether the first index of refraction corresponds to the desired predetermined concentration of API in the API-containing liquid 25 upon production of the API-containing liquid. For instance, at the initial time, a first index of refraction of the API-containing liquid can be determined. In one example, the first or initial concentration of the API in the API-containing liquid can be determined by correlating the measured first index of refraction to the corresponding API concentration in the reference index. More API or API carrier can be added to the API-containing liquid 25 as desired to arrive at the predetermined concentration of API in the API-containing liquid. Alternatively, the predetermined volume of API-containing liquid to be delivered to the substrate 23 can be adjusted based on the concentration of API. If the second index of refraction is different than the first index of refraction, the second index of refraction can similarly be compared to the reference index of refractions to determine the second concentration of API in the API-containing liquid.

If the second index of refraction indicates that the second concentration of API in the API-containing liquid is greater than the predetermined concentration or initial concentration, additional liquid carrier can be added to the API-containing liquid until the index of refraction indicates that the concentration of API in the API-containing liquid is substantially equal to (e.g., within 0.1%) the predetermined concentration or the initial concentration. Alternatively the volume of API-containing liquid to be delivered to the substrate 23 can be correspondingly reduced so that the API-containing liquid delivered to the substrate 23 also delivers the desired predetermined dosage of API. If the second index of refraction indicates that the concentration of API in the API-containing liquid is less than the predetermined concentration, additional API can be added to the API-containing liquid until the index of refraction indicates that the concentration of API in the API-containing liquid is substantially equal to (e.g., within 0.1%) the predetermined concentration. Alternatively the volume of API-containing liquid to be delivered to the substrate 23 can be correspondingly increased so that the API-containing liquid delivered to the substrate 23 also delivers the desired predetermined dosage of API.

In other examples, either or both of the first concentration and the second concentration of API in the API-containing liquid can be determined by delivering a sample of the API-containing liquid from the container or tank to an HPLC, and using the HPLC to both identify the API in the liquid carrier of the API-containing liquid and the concentration of API in the API-containing liquid.

With continuing reference to FIG. 9, the system 20 can be configured to ensure that the steps performed by the pump 49 drive the predetermined volume of API-containing liquid through the second conduit 53 and thus out the dosing head 46 (less any head space in the delivery line 59 and/or pump

49 that does not include API-containing liquid when the pump 49 begins delivery to a new substrate 23). Accordingly, in one example, the system 20 can further include a filter 118, also known as a frit, that is configured to remove contaminants from the API-containing liquid 25, for instance in the event that contaminants were introduced in the API-containing liquid 25 during production, storage, transfer, or in the reservoir 26. The filter 118 can be an inline filter, meaning that the filter 118 is disposed in the delivery line 59. The filter 118 can be disposed in the second conduit 53 or in the first conduit 51 as desired. In one example, the filter 118 can be disposed between the reservoir 26 and the pump 49. Thus, the filter 118 can be disposed upstream of the pump 49 in the first conduit 51 to prevent or minimize travel of debris in the API-containing liquid 25 from reaching the pump 49. Unless otherwise indicated, the terms “upstream” and “downstream” and derivatives thereof as used herein refer to the direction of the flow of API-containing liquid during normal or forward operation of the pump 49 that delivers API-containing liquid to the dosing head 46.

Figure 11:
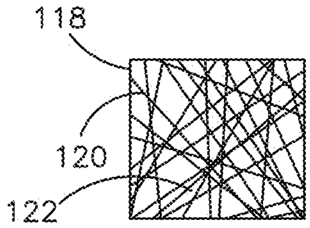
FIG. 11 is a schematic view of an inline filter of the dosing system of FIG. 9.

The API-containing liquid can thus travel through from the reservoir 26 through the filter 118 and to the pump 49. In one example, the filter 118 can be a mechanical filter configured to entrap unwanted particles that may be present in the API-containing liquid. As shown in FIG. 11, the filter 118 can include a plurality of filaments 120 that are arranged so as to define interstices 122 that are configured to entrap contaminants as the API-containing liquid travels through the filter 118. The interstices 122 can have any suitable average pore size as desired. In one example, the average pore size can be in a range from approximately 10 micrometers to approximately 20 micrometers. The filaments 120 can be made from metal, polymer, or any suitable alternative material as desired. It is recognized that the filter 118 can be removed from the fluid delivery line 59 and either cleaned or replaced by a new filter 118 as desired. It should be appreciated that the system 20 can include any suitable alternatively constructed filter as desired.

Referring again to FIG. 9, the instance, the system 20 can be configured to remove unwanted gas in the API-containing liquid 25 from the fluid delivery line 59. In particular, the system 20 can include a degasser 124 that is disposed in the fluid delivery line 59, and is configured to remove dissolved gas in the API-containing liquid in the fluid delivery line 59. The degasser 124 can include a degasser membrane, or a membrane contactor, having open volumes. As the API-containing liquid flows through the degasser 124, gas that is dissolved in the fluid delivery line flows into the open volumes and is removed from the API-containing liquid. In one example, the membrane can include hollow polymeric filaments that define the interstices. The degasser 124 can be disposed upstream of the pump 49 with respect to the forward flow direction of API-containing liquid toward the dosing head 46. In one example, the degasser 124 can be disposed in the first conduit 51 between the reservoir 26 and the pump 49. For instance, the degasser 124 can be disposed between the filter 118 and the pump 49. Therefore, the API-containing liquid can be filtered before flowing through the degasser 124, and filtered and degassed before flowing to the pump 49.

With continuing reference to FIG. 9, the system 20 can further include a bubble detector 142 that is configured to detect whether the API-containing liquid includes gas in the fluid delivery line 59. The bubble detector 142 can be an inline bubble detector, meaning that the bubble detector 142 can identify the presence of gas in the API-containing liquid in the delivery line 59 without diverting the API-containing liquid out the delivery line. The bubble detector 142 can be located immediately upstream of the dosing head 46 with respect to the direction of forward flow of API-containing liquid in the fluid delivery line 59 toward the dosing head 46, thereby ensuring that the API-containing liquid 25 does not contain gas when the API-containing liquid 25 is emitted out of the dosing head 46 and ultimately delivered to the substrate 23. The bubble detector 142 can be in communication with the controller 57, so that the controller 57 can enter an alarm condition when gas is detected in the fluid delivery line 59. Alarm conditions from the controller 57 can identify a detected condition that caused the alarm condition to the user. In some instances, depending on the nature of the alarm condition, the controller 57 will cause the system 20 to enter an idle mode, as described in more detail below. In other instances, the nature of the alarm condition will provide output to the user, who can adjust a setting of the system in response to the alarm condition or perform diagnostics as desired.

The bubble detector 142 can rely on any suitable conventional technology to sense the presence of gas in the fluid delivery line 59. In one example, the bubble detector 142 can rely on ultrasound or light scattering to detect gas or bubbles in the API-containing liquid. Further, as is described in more detail below, the system 20 can include one or more pressure sensors 162 that are disposed in the second conduit 53. The pressure measured by the pressure sensors 162 can also detect a presence of bubbles in the API-containing liquid. In particular, a decrease of the pressure of the API-containing liquid in the second conduit 53 as sensed by the pressure sensor 162 can indicate a presence of bubbles in the API-containing liquid. It is further recognized that a decrease of the pressure in the API-containing liquid in the second conduit 53 can also indicate a leak in the second conduit and a decrease in API concentration in the API-containing liquid. Therefore, an unexpected decrease in the pressure of the API-containing liquid can cause the controller 57 to detect each of the presence of bubbles, a leak, and a decrease in concentration. The system 20 can enter the alarm condition, and the controller 57 can output an feedback indicating the possible presence of bubbles, a leak, and a decrease in concentration. The system 20 can enter the idle condition whereby a user can inspect the system for bubbles and leaks, and can inspect the API-containing liquid for a reduction in concentration.

In other examples, the system can include a light scattering device that is configured to detect the presence of bubbles or contaminants in the API-containing liquid that flows through the output line 89. The light scattering device can be inline with the output line 89, and in particular with the second conduit 53, and can detect the presence of bubbles or contaminants in real time as it flows through the second conduit 53. The light scattering device can include a light source that is directed into the flow of the API-containing liquid, and one or more detectors can detect light that has scattered off particles or bubbles in the API-containing liquid. If scattered light is detected, the controller 57 can enter an alarm condition that indicates that a presence of a bubble and/or particle contaminant is present in the API-containing liquid.

As will be described in more detail below, the system can include either or both of a UV-Vis spectrometer and a high-performance liquid chromatography (HPLC) that can determine the concentration of the API, and can also determine whether bubbles exist in the API-containing liquid. Accordingly, if a decrease in pressure of the API-containing liquid is observed, and the spectrometer and/or HPLC does not indicate the presence of bubbles or a decrease in concentration, the controller 57 can determine by process of elimination that the decrease in pressure indicates a leak in the output line 89. If, on the other hand, the spectrometer and/or HPLC indicates the presence of bubbles, then the controller 57 can confirm the presence of bubbles in the output line 89. If the spectrometer and/or HPLC indicates a decrease of API concentration in the API-containing liquid, then the controller 57 can confirm that the concentration of the API has decreased.

Figure 12A:
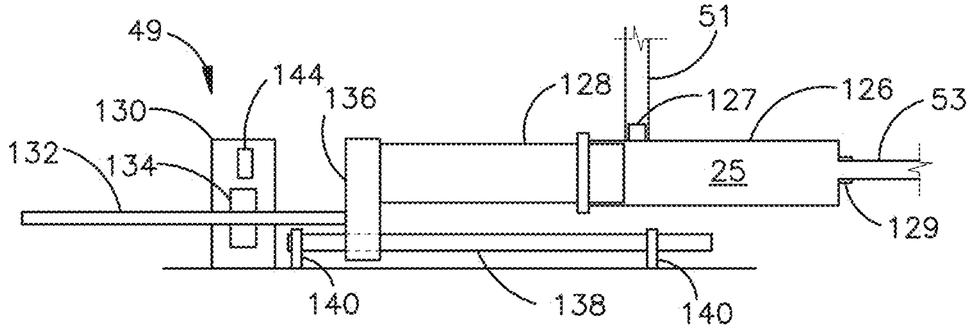
FIG. 12A is a schematic view of a pump of the dosing system of FIG. 9, the pump having a plunger and a syringe.

The pump 49 will now be described with reference to FIGS. 9 and 12A. As described above the pump 49 can be a positive displacement pump. For instance, the pump 49 can be a positive displacement syringe pump having a syringe 126 that can include an input valve 127 at an interface between the first conduit 51 and the syringe 126. The input valve 127 is movable between an open position and a closed position. When the input valve 127 is in the open position, the syringe is open to the first conduit 51. Accordingly, a quantity of the API-containing liquid 25 is allowed to flow from the reservoir 26 and the first conduit 51 into the syringe 126 during a filling operation. After the filling operation, the input valve 127 is moved to the closed position, which prevents the API-containing liquid 25 from flowing through the valve, thereby isolating the syringe 126 from the first conduit 51. The input valve 127 can be a one-way valve, such that when the input valve 127 is in the open position, the input valve 127 only allows for flow of the API-containing liquid through the input valve 127 in a direction from the reservoir to the pump 49, and prevents the API-containing liquid from flowing through the valve in a direction from the pump 49 to the reservoir 26.

The syringe 126 can have an outlet coupling 129 that is coupled to the second conduit 53. The pump 49 can further include a plunger 128 that is configured to translate in the syringe 126 in a forward direction so as to drive the API-containing liquid out the outlet of the syringe 126 and into the second conduit 53 in the forward direction. The plunger 128 can further be configured to translate in the syringe in a rearward direction so as to drive the API-containing liquid in the second conduit 53 and in the dosing head 46 in the rearward direction toward the pump 49, and in particular toward the syringe 126. When the syringe 126 is empty, the pump 49 can enter an intake cycle whereby the input valve 127 is opened, the plunger 128 is driven to move in the rearward direction, and API-containing liquid 25 flows into the syringe 126 from the reservoir 26 and/or the first conduit 51. When a desired volume of API-containing liquid is in the syringe 126, the pump can enter a delivery cycle whereby the input valve 127 is closed, and translation of the plunger 128 in the forward direction causes API-containing liquid to flow from the pump 49 into the second conduit 53. The input valve 127 can be a zero dead volume valve or any suitable alternative valve as desired. The API-containing liquid can be incompressible. Accordingly, when a volume of API-containing liquid flows from the pump into the second conduit 53, the same volume of API-containing liquid advances in the second conduit. Accordingly, when the second conduit 53 and dosing head 46 are full with API-containing liquid, the same volume of API-containing liquid is emitted from the dosing head 46.

A full stroke of the plunger 128 causes the plunger 128 to be fully driven in the forward direction in the syringe 126, which thus causes substantially all of the API-containing liquid 25 to be driven from the syringe 126 to the second conduit 53. The syringe 126 can have any suitable volume capacity as desired. In some examples, the volume capacity can be in a range from approximately 50 microliters to approximately 1 liter. For instance, the volume capacity can be in a range from approximately 50 microliters to approximately 250 microliters. In other examples, the capacity can be in a range from approximately 250 microliters to approximately 1 liter. The volume capacity of the syringe 126 can be determined, at least in part, by the amount of API-containing liquid to be dosed to the substrate 23, and how many substrates 23 can be dosed by the volume of API-containing liquid in the syringe 126 before the syringe 26 needs to be refilled with API-containing liquid from the reservoir 26. In some examples, a stroke of the pump 49 can define a full delivery to a substrate 23 that is aligned with each at least one dosing head. In other examples, a full delivery to a substrate that is aligned with each at least one dosing head can be accomplished by performing a portion of a stroke of the pump 49. It is recognized that the pump 49 can deliver the API-containing liquid to a single dosing head or to a plurality of dosing heads (for instance through a manifold).

Figure 12B:
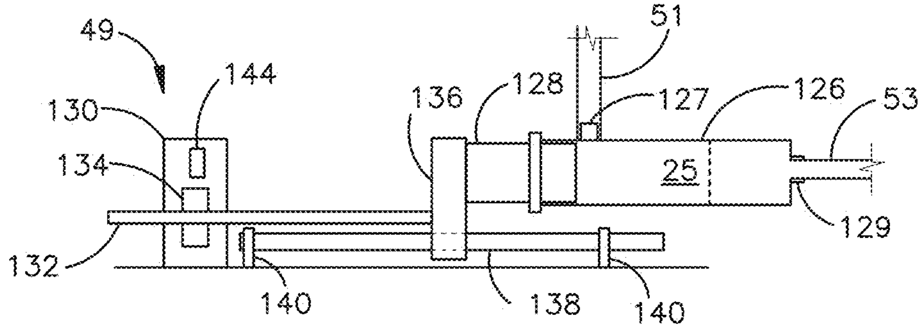
FIG. 12B is a schematic view of the pump of FIG. 12A, shown in a delivery position whereby the plunger is moved in a forward direction in the syringe so as to deliver API out of the pump.

The pump 49 includes a motor 130 that is operable to selectively drive the plunger 128 in the forward direction and the rearward direction. In one example, the motor 130 can include a threaded drive shaft 132 that is coupled to the plunger 128. For instance, the motor 130 can include an attachment member 136 that is attached to each of the drive shaft 132 and the plunger 128. Thus, the drive shaft 132 is translatably coupled to the plunger 128. The attachment member 136 can be translatable along guide rods 138 that, in turn, are supported by guide support members 140. The motor 130 can further include a drive member such as a drive wheel 134 that is threadedly mated to the drive shaft 132. The drive wheel 134 is rotatable in a first direction of rotation that causes the threaded engagement with the drive shaft 132 to drive the drive shaft 132 to move in the forward direction, which thereby causes the plunger to translate in the forward direction with the drive shaft 132 as shown in FIG. 12B. The drive wheel 134 is rotatable in a second direction of rotation opposite the first direction of rotation that causes the threaded engagement with the drive shaft 132 to drive the drive shaft 132 to move in the rearward direction, which thereby causes the plunger to translate in the rearward direction with the drive shaft 132.

It should be appreciated that the drive wheel 134 is operable to rotate in incremental steps, which thereby causes the plunger 128 to likewise translate in incremental displacement steps. Thus, each step of the drive wheel 134 corresponds to a step of the plunger 128. Each incremental step of the plunger 128 drives a corresponding incremental volume of API-containing liquid 25 out of the syringe 126 and into the second conduit 53. Thus, the successive steps of the pump 49, and in particular of the plunger 128, can cause the corresponding incremental volumes of the API-containing liquid 25 to be expelled out of the outlet of the dosing head 46. Each incremental step can be substantially (within manufacturing tolerances) equal to each other. The drive wheel 134, and thus the plunger 134, can perform a number of successive incremental steps that causes the pump 49, and in particular the plunger 128, to perform a full stroke in the forward direction which drives substantially the entire volume of the API-containing liquid 25 from the syringe 126 to the second conduit 53 when the entire volume capacity of the syringe 126 is full of API-containing liquid 25. In one example, the number of steps that empties the entire volume capacity from the syringe 126 can be in a range from approximately 100,000 steps to approximately 500,000 steps, such as from approximately 100,000 steps to approximately 400,000 steps, such as from approximately 200,000 steps to approximately 400,000 steps, such as from approximately 300,000 steps to approximately 400,000 steps. In one example, the number of steps can be in a range from approximately 350,000 steps to approximately 400,000 steps such as approximately 384,000 steps. In one example, the pump can be a C-Series or CX-Series precision OEM syringe pump commercially available from TriContinent having a principal place of business in Auburn, CA.

The large number of incremental steps performed by the pump to empty the syringe 128 defines a dosing resolution that allows for the volume of API-containing liquid 25 that is delivered to the substrate 23 to be more precisely and repeatably controlled with respect to conventional systems that deliver individual drops. In particular, the conventional systems determine a volume of API-containing liquid that has a dosing resolution equal to the volume of each droplet delivered to the substrate. Otherwise stated, the volume of API-containing liquid to be delivered to the substrate in conventional drop-based systems can be determined only as a multiple of the volume of an individual drop delivered on a drop-by-drop basis. Conventional drop-based systems are incapable of delivering a volume of API-containing liquid that not entirely divisible by the volume of a full droplet to the underlying substrate 23. Therefore, the quantity of API delivered to the substrate in a drop-based system is necessarily divisible by the quantity of API in each drop. The present inventors have recognized that the volume of API-containing liquid to be delivered to the substrate 23 can be determined as a multiple of the volume displacements, or steps, performed by the pump 49. Thus, the volume of the API-containing liquid 25 to be delivered to the substrate 23 is evenly divisible by each incremental volume of the API-containing liquid 25 that is driven into the second conduit 53 in response to each incremental step of the pump 49, and in particular of the plunger 128. The incremental volume is therefore significantly less than the volume of each of droplets of conventional drop-based systems. Thus, the system 20 is configured to more accurately control the volume of API-containing liquid 25, and thus the dosage API in the API-containing liquid, that is delivered to the underlying substrate 23. Otherwise stated, the dosage variances can be limited to the quantity of API in the API-containing liquid delivered in a single step of the pump 49. Operation of the pump 49 in the forward direction can be discontinued immediately when it is determined that a final step has caused an entirety of the predetermined dosage of API, and/or the corresponding volume of API-containing liquid, to be emitted from the dosing head 46. Operation of the pump in the forward direction can resume when a new substrate is moved into alignment with the dosing head 46 to be dosed.

The controller 57 can provide feedback that the pump 49 is performing the incremental steps as described above. In this regard, it is recognized that the pump 49 operates on input electrical power. Accordingly, the system 20 can include an electric circuit monitor that detects increases and decreases of electrical current in the input electrical power to the pump 49 that might impact reliable operation of the pump 49.

The system 20 can further include a pump confirmation device to ensure that the pump 49 is performing the each of the incremental steps as described above. In one example, the pump confirmation device can be configured as an optical encoder 144 that is able to detect whether each stroke of the pump 49 has been performed. In one example, the encoder 144 can be an internal encoder of the pump 49. The optical encoder 144 can have an encoder resolution that is equal to the number of steps performed by the pump 49, such that the encoder 100 can confirm whether the pump 49 is performing all of the desired positive displacement steps during operation of the pump 49. That is, the encoder resolution can be the length of the stroke of the pump 49 divided by the number of steps per stroke of the pump 49. During normal operation, the light beam from the optical encoder will detect the motion of the pump 49 associated with positive displacement of the pump 49 during each step. For instance, if the pump 49 fails to detect the motion of the pump 49, it can be determined that at least one of the expected positive displacement steps has not taken place. The controller 57 can be in communication with the optical encoder 144, and can enter an alarm condition upon determination that the pump 49 is not performing all of the positive displacement steps. During an alarm condition, the controller can activate an audible alarm, a visual alarm, a remote alarm, and/or can deactivate the system 20 until the alarm condition has been corrected.

With continuing reference to FIG. 9, the system 20 can further be configured to ensure that each step of the motor advances a desired quantity of API into the second conduit 53, and thus out of the dosing head 46 (less any head space that may be present in the second conduit 53 and/or dosing head 46 when the pump 49 begins dosing a new substrate). If head space exists in the second conduit 53 and/or the dosing head 46, the pump 49 can operate to drive the API-containing liquid to a position flush with the tip 61. The pump 49 can then begin driving the predetermined volume of API-containing liquid 25 to the conduit 53, which thus causes the predetermined volume of API-containing liquid 25 out of the dosing head outlet 63, which in turn causes the predetermined dosage of API to be delivered to the underlying substrate. The controller 57 can thus determine a number of incremental steps to be performed by the pump 49 to deliver the desired predetermined dosage of the API to the underlying substrate.

In one example, a predetermined volume of API-containing liquid to be delivered to the substrate 23 can be calculated by dividing the desired predetermined dosage by the concentration of API in the API-containing liquid. A predetermined number of pump steps can then be calculated by dividing the predetermined volume of API-containing liquid to be delivered to the substrate 23 by the volume of API-containing liquid that is advanced in the second conduit 53 from each incremental step of the pump 49. When a predetermined number of steps to be performed by the pump 49 drives a predetermined volume of API-containing liquid into the second conduit 53 when no head space exists in the second conduit 53 and/or dosing head 46, that volume of API-containing liquid is therefore emitted out of the dosing head 46. The emitted API-containing liquid either travels to the substrate, or remains on the dosing head 46 as a remainder that is then delivered to the substrate by the wash station in the manner described above. Thus, substantially all of the emitted API-containing liquid is ultimately delivered to the substrate. When the API-containing liquid in the conduit 53 has a constant predetermined concentration of API, the predetermined volume of API-containing liquid delivered to the substrate 23, in turn, delivers the predetermined dosage of API to the underlying substrate 23. Once the predetermined dosage of API has been delivered, the substrate 23 can be removed from alignment with the dosing head 46, and a subsequent substrate 23 can be brought into alignment with the dosing head 46 to be dosed.

As described above, the pump 49 is operable in a reverse direction, which causes API-containing liquid to flow from the second conduit 53 into the syringe 126. When the pump operates in the reverse direction, the distal end of the API-containing liquid that has traveled through the second conduit 53 can retract in the dosing head 46 or into the second conduit 53. Therefore, after operating the pump 49 to drive the predetermined volume of API-containing liquid out of the dosing head 46, the pump 49 can be subsequently operated in a reverse direction that causes the API-containing liquid in the second conduit 53 to flow in a direction away from the dosing head 46 and toward the pump 49. It should be appreciated that operating the pump 49 in the reverse direction can bring the API-containing liquid in the dosing head 46 to a predetermined location. The location can be flush with the tip or outlet of the dosing head 46, or can be spaced from the outlet to create a head space. In some examples, the location can be consistent after the predetermined volume of API-containing liquid has been delivered to each substrate 23. As a result, each dosing operation begins with the same volume of API-containing liquid in the output line 89. If the volume of API-containing liquid in the output line 89 creates a head space in the output line 89, the pump can operate until the API-containing liquid terminates at a location flush with the tip or outlet of the dosing head 46. The pump can then begin to dose the predetermined volume of liquid to a subsequent substrate. It should be appreciated that the terminal or distal end of the API-containing liquid in the output line 89 can be in a repeatable start position after to dosing a substrate and prior to dosing a subsequent substrate that be brought in alignment with the dosing head 46. The pump 49 can therefore drive a consistent volume of API-containing liquid in the forward direction from the repeatable start position to dose each substrate with the predetermined volume of API-containing liquid, and thus the desired dosage of API.

In one example, operating the pump 49 in the reverse direction can also avoid or reduce spillage of the API-containing liquid out the dosing head 46, for instance after the predetermined volume of API-containing liquid has been delivered to the substrate 23. When the pump 49 operates in the reverse direction, the API-containing liquid is drawn inward from the outlet of the dosing head 46 toward the pump 49. Therefore, operation of the stepper motor in the reverse direction can reduce or avoid wicking of the API-containing liquid along the external surface of the dosing head. Further, operating the stepper motor in the reverse direction can separate the remainder bolus 75 (see FIG. 7C) from the initial volume of API-containing liquid that travels to the substrate 23. Operating the stepper motor in the reverse direction can also separate the remainder bolus 75 from the API-containing liquid that is intended to be delivered to a subsequent substrate 23, in the manner described above. Operating the stepper motor in the reverse direction can also reduce the volume of the remainder bolus 75. Further, when the input valve 127 (see FIG. 12A) of the pump 49 is in the open position, operation of the stepper motor in the reverse direction can cause API-containing liquid to flow to the reservoir 26. For instance, it may be desired to deliver the API-containing liquid from the pump 49 to the reservoir 26 as part of a procedure that shuts down the system 20, or when the system 20 is in an alarm condition and it is desired to remove the API-containing liquid from the delivery line 59 and the output line 89.

With continuing reference to FIGS. 9 and 12, after the pump 49 has performed a plurality of steps to deliver a predetermined volume of the API-containing liquid 25 to the delivery line, and thus out of the dosing head to one or more substrates, the controller 57 can verify whether the actual volume delivered is equal to the predetermined volume. For instance, a quantity of API-containing liquid can be delivered from the reservoir 26 to the pump 49 so that the pump has a known volume of the API-containing liquid in the syringe 126. The known volume can be defined by a full volume of the syringe 126 in some examples. The plurality of steps of the pump 49 can then be performed, which decreases the volume of API-containing liquid in the syringe 126. In some examples, the delivery line 59 can be primed, such that the delivery line 59 and the dosing head 46 are full with API-containing liquid, before the plurality of steps of the pump 49 are performed. Accordingly, the volume of API-containing liquid that the pump 49 drives into the second conduit 53 is correspondingly emitted from the dosing head.

The syringe 126 can then be replenished with the API-containing liquid from the reservoir 26 until the syringe 126 again has the known volume of API-containing liquid. It is recognized that the replenishing step decreases the volume of API-containing liquid in the reservoir 26. It can then be determined whether the decreased volume of API-containing liquid in the reservoir 26 equals the predetermined volume of API-containing liquid that was to be dosed to the at least one substrate.

In one example, the decreased volume of API-containing liquid in the reservoir 26 can be calculated by performing a series of steps. First, the reservoir 26 can be weighed to determine a first weight before the quantity of API-containing liquid is delivered from the reservoir 26 to the pump 49 so that the pump has a known volume of the API-containing liquid in the syringe 126. A first mass of API-containing liquid can be determined from the first weight. The reservoir 26 can also be weighed to determine a second weight after the syringe 126 has been replenished with the API-containing liquid from the reservoir 26 until the syringe again has the known volume of API-containing liquid. A second mass of API-containing liquid can be determined from the second weight. The mass difference of API-containing liquid in the reservoir 26 can be calculated by subtracting the second mass from the first mass. Finally, the calculated mass difference can be multiplied with the specific density of the API-containing liquid to calculate the decreased volume in the reservoir 26. If the calculated decreased volume in the reservoir 26 (which defines the actual volume of API-containing liquid that was dosed to the at least one substrate) is substantially different (for instance greater than 0.1%) than the predetermined volume, the controller 57 can enter an alarm condition. It is recognized that the decreased volume can be compared to the total volume of the reservoir 26, and based on the decreased volume, it can be determined when to replenish the reservoir 26 with an additional quantity of the API-containing liquid 25.

The method of verifying whether the actual volume delivered is equal to the predetermined volume can include the step of successively aligning a plurality of substrates with the dosing head 46, and performing the steps of the pump 49 delivers API-containing liquid to each of the successively aligned substrates. The calculated decreased volume of API-containing liquid 25 in the reservoir 26 can be divided by the number of substrates to determine an average volume of API-containing liquid that has been delivered to each of the substrates. If desired, an actual average dosage of API delivered to the substrates 23 can be calculated by multiplying the average volume and the concentration of API in the API-containing liquid 25. The calculated average dosage of API delivered to each of the substrates can then be compared to a predetermined dosage of API that corresponds to the plurality of steps performed by the pump 49. If the calculated average dosage is different than the predetermined dosage by a threshold amount (e.g., by more than 0.1%), the controller 57 can enter the alarm condition.

In other examples, the actual decreased volume in the reservoir 26 can also be determined by identifying a first level of the API-containing liquid in the reservoir using an optical sensor before the API-containing liquid is delivered to the pump to achieve the known volume in the syringe 126. A second level of the API-containing liquid in the reservoir can be identified using the optical sensor after API-containing liquid in the reservoir 26 is delivered to the pump 49 to replenish the syringe 126. The decreased volume in the reservoir 26 can thus be determined by multiplying a cross-sectional area of the reservoir and a difference between the first and second levels.

With continuing reference to FIG. 9, the controller 57 can be configured to perform an alternative method to confirm whether the pump 49 is driving the correct volume of API-containing liquid 25 into the second conduit 53. Thus, the controller 57 can confirm that the incremental steps of the pump 49 are repeatably and accurately delivering the predetermined volume output of the API-containing liquid. In this regard, the system 20 can include a validation station 146. A validation valve 148 can be positioned downstream of the pump in the second conduit 53. The validation valve 148 can be a zero dead volume valve or any suitable alternative valve as desired. When the validation valve 148 is in a first or closed position, the API-containing liquid travels continuously and uninterrupted past the validation station 146 without flowing into the validation station 146. When the validation valve 148 is in second or open position, the volume of API-containing liquid that is driven to the second conduit 53 during operation to the pump 49 is diverted and redirected through the validation valve 148 and into the validation station 146. It is appreciated that the volume of API-containing liquid that is driven to the second conduit 53 during operation to the pump 49 is diverted and redirected through the validation valve 148 and into the validation station 146 because the API-containing liquid is incompressible. Therefore, the volume of API-containing liquid that is driven into the second conduit 53 is equal to the volume of API-containing liquid that is driven out of the second conduit 53 when the validation valve 148 is in the open position, assuming no head space exists in the second conduit 53. The validation valve 148 can be a one-way valve, such that when the validation valve 148 is in the open position, the validation valve 148 only allows for flow of the API-containing liquid through the validation valve 148 in a direction from the second conduit 53 to the validation station 146, and prevents the API-containing liquid from flowing through the validation valve 148 in a direction from the validation station 146 to the second conduit 53.

The controller 57 can determine a total predetermined validation volume based on actuation of the pump 49. For instance, when the pump 49 includes a stepper motor, the total predetermined validation volume can be based on the predetermined number of steps performed by the pump 49 when the API is diverted to the validation station 146 (also referred to as validation steps). In particular, the total predetermined validation volume can be calculated by multiplying the validation steps and the predetermined known volume of API-containing liquid that is driven to the second conduit 53 in each step. It should be appreciated that when validation valve is in the open position, the validation station 146 receives a total actual validation volume that is delivered during the performance of the validation steps by the pump 49. The controller 57 can thus compare the total actual validation volume validation volume to the total predetermined validation volume. If the total actual validation volume predetermined validation volume is substantially equal to the total predetermined validation volume, the controller 57 concludes that the pump 49 is performing normally. If the total actual validation volume is substantially different than the total predetermined validation volume, the controller 57 can enter an error condition, and diagnostics and repairs can be performed on the system 20.

The controller 57 can determine the total actual validation volume that is driven to the validation station 146 in any suitable manner as desired. In one example, the validation station 146 can include at least one validation tube 150 such as a plurality of validation tubes 150 that are supported on a movable support surface 152. The validation tubes 150 can have any suitable diameter as desired, such as from approximately 50 micrometers to approximately 3 millimeters. The validation system 146 further includes a validation conduit 154 that is configured to receive the diverted API-containing liquid 25, and a validation nozzle 156 that is configured to deliver the diverted API-containing liquid selectively to the validation tubes 150. Each validation tube 150 can be disposed on a scale 153, such that the initial weight of each validation tube 150 when empty is known. The support surface 152 can be movable so as to place the validation tubes selectively in alignment with the validation nozzle 156.

In one example, the validation tubes can receive different individual volumes of the total actual total validation volume. Thus, the individual volumes of each validation tube are defined by different corresponding numbers of steps performed by the stepper motor when the API-liquid is diverted to the validation system. Further at least two or more up to all of the individual volumes can be different from each other. Thus, a first validation tube 150*a* can receive a first individual volume of API-containing liquid that travels to the validation station 146 due to a first number of validation steps of the pump 49. A second validation tube 150*b* can receive a second individual volume of API-containing liquid that travels to the validation station 146 due to a second number of validation steps of the pump 49. The second number of validation steps can be different than the first number of validation steps. A third validation tube 150*c* can receive a third individual volume of API-containing liquid that travels to the validation station 146 due to a third number of validation steps of the pump 49. The third number of validation steps can be different than the first and second numbers of validation steps. The total actual validation volume can be the sum of all individual validation volumes.

Each individual volume of API-containing liquid in the tubes 150 can be measured by weighing the respective tubes 150 after they have received their respective individual volumes of API-containing liquid. The initial weight can be subtracted from the measured weight to arrive at the individual volume. Alternatively, an optical detector 158 can be applied to each of the validation tubes 150 to determine the level of API-containing liquid in each tube, and thus each individual volume of each tube.

Each individual volume of API-containing liquid in the tubes 150 can be compared to a predetermined volume of API that corresponds to the respective number of validation steps associated with each tube. In particular, the predetermined volume that corresponds to each number of validation steps can be calculated by multiplying the respective number of validation steps and the known volume of API-containing liquid delivered with each step of the pump 49. The actual validation volume can be discarded after the validation process has been completed. It should be appreciated that a total number of validation steps of the pump 49 that is driven to the validation station 146 can equal the cumulative number of validation steps associated with each tube 150. In one example, the total number of validation steps can equal a number of steps of the pump 49 that are associated with a desired quantity of the API-containing liquid that is delivered to the substrate 23 to deliver a predetermined desired dosage of API to the substrate.

While the system 20 is shown at FIG. 9 as including the pump 49, it is appreciated that the system 20 can include first and second pumps 49 that are each in fluid communication with the reservoir 26 and the second conduit 53 in the manner described above. During operation, as one of the pumps 49 is delivering the API-containing liquid from its syringe 126 to the second conduit 53, syringe 126 of the other one of the pumps 49 can receive the API-containing liquid from the reservoir 26 in the manner described above. Thus, while one of the pumps 49 performing a delivery step, the other of the pumps 49 can perform a filling step. When the API-containing liquid in the pump 49 that is delivering the API-containing liquid to the second conduit 53 decreases to a threshold level, the pump can initiate a filling sequence whereby the pump receives API-containing liquid into the syringe while the other pump begins delivering the API-containing liquid to the second conduit 53.

With continuing reference to FIG. 9, the system 20 can also monitor the flow of the API-containing liquid 25 in the second conduit 53 as it travels from the pump 49 to the dosing head 46. In one example, the system 20 can include a flow meter 160 that is configured to measure the flow rate in the second conduit 53. The flow meter 16 is in electrical communication with the controller 57. The flow meter 160 can be an inline flow meter that can be installed in the second conduit 53, such that the API-containing liquid flows through the flow meter 16. Alternatively, the flow meter 160 can be an insertion meter that is inserted through an aperture in the second conduit 53 to measure the flow rate of the API-containing fluid 25 in the second conduit 53. Alternatively still, the flow meter 160 can be clamped onto an exterior of the second conduit 53 to measure the flow rate of the API-containing liquid 25 in the second conduit 53.

The flow meter 160 can be configured to detect a flow rate reduction of the API-containing liquid in the second conduit 53. For instance, a flow reduction can be due to any one of a buildup of residue in the second conduit 53, foreign matter disposed in the second conduit 53, bubbles disposed in the second conduit 53, a buildup of residue at the dosing head 46, or performance issues with the pump 49. When the flow meter 160 detects an unexpected flow rate reduction, the controller 57 can enter an alarm condition, and diagnostics and repairs can be performed on the system 20 as warranted.

With continuing reference to FIG. 9, the dosing system 20 can include an imaging system having a field of view that is configured to image at least one region of interest. The region of interest can include any one or more up to all of the substrate 23, the external surface of the dosing head 46, and the API-containing liquid as it travels from the dosing head 46 to the substrate 23. For instance, the imaging system can include an optical imaging system having, for instance, a camera that generates image data that can be forwarded to the controller 57 and accessed by a user. The optical imaging system can capture images of any one or more up to all of a landing zone of the substrate (a zone on the surface of the substrate that faces the dosing head 46 to which the API-containing liquid is delivered), the API-containing liquid as it travels from the dosing head 46 to the substrate 23, and the external surface of the dosing head 46. In one example, the optical imaging can be performed by respective cameras. For instance, a square area of the landing zone can be determined and compared to a predetermined landing zone. The cameras can be configured to produce images by having between 25 times and 100 times magnification.

In one example, the imaging system can include detectors 95 that are configured to sense an object of interest. For instance, the detectors 95 can be configured as cameras that capture images of the object of interest. In one example, the object of interest can include the surface of the substrate 23 that faces the dosing head 46, including the API-containing liquid on the substrate 23 (during or after the predetermined volume of API-containing liquid has been delivered to the substrate), a liquid carrier on the substrate 23 prior to evaporation of the liquid carrier, the API that remains on the substrate 23 after evaporation of the liquid carrier. One or more of the detectors are configured to detect the API-containing liquid as it travels from the dosing head 46 to the substrate 23. One or more of the detectors can be configured to sense API that has adhered to the dosing head 46, such as the external surface of the dosing head 46. The images of the object of interest can be captured in any suitable manner as desired. For instance, a reference image can be taken of a region of interest that includes or will include the object of interest at a first time. A subsequent image of the region of interest can then be taken a second time after the first time to produce a second image. The reference image can then be subtracted from the second image to detect changes to the object of interest that occurred between the first time and the second time. In one example, the reference image can be defined by the external surface of the dosing head 46, and object of interest can be defined by residual API. In another example, the reference image can be defined by the dosing surface of the substrate 23, and the object of interest can be one or more up to all of the API-containing liquid, the API, and the carrier liquid. In another example, the reference image can be defined by the API-containing liquid as it travels from the dosing head 46 to the substrate 23. It should be appreciated that a plurality of subsequent images at different times over a duration of time as desired, and the reference image can be subtracted from the subsequent images to identify changes to the external surface with respect to the reference image at each of the times. In another example, a previously-captured subsequent image can be subtracted from a later-captured subsequent image to identify changes to the external surface at various time durations.

Alternatively or additionally, the detectors 95 that can be configured to output voltage data to the controller 57 regarding the object of interest. In one example, the object of interest can include any one or more up to all of API-containing liquid on the substrate 23, liquid carrier on the substrate 23 prior to evaporation of the liquid carrier, API-containing liquid traveling from the dosing head 46 to the substrate 23, and residual API on the external surface of the dosing head 46. The detectors can be configured to generate, for instance, optical diffraction patterns of the object of interest. Thus, for example, the detectors can generate an optical diffraction pattern of the external surface of the dosing head. In other examples, the imaging system can define a droplet counter that counts the droplets after ejection from the dosing head, when the API-containing liquid is delivered in the form of droplets. The imaging system can also determine one or more of a shape and a volume of the API-containing liquid being delivered to the substrate.

The controller 57 can respond to the images or detected objects. For instance, the controller 57 can initiate a washing sequence whereby the wash fluid is delivered to the external surface of the dosing head 46 when a threshold quantity of residual API is detected on the dosing head, for instance at the external surface of the dosing head 46, which causes the threshold quantity of residual API to be dislodged and delivered to the substrate 23. The threshold quantity can be dislodged while the pump 49 is operating to deliver API-containing liquid to the substrate 23. Thus, the wash fluid can deliver residual API to the substrate while the initial volume of API is being delivered to the substrate 23, for instance when the threshold quantity of residual API has been detected. The threshold quantity of residual API can be detected once or more than once while the initial volume of API is delivered to the substrate. Therefore, the wash can dislodge residual API and deliver residual API to the substrate more than once while the initial volume of API is delivered to the substrate. Residual API can also be delivered to the substrate after the initial volume of API has been delivered to the substrate 23 in the manner described above. The imaging system can further define a wicking detector, whereby the controller 57 can determine that the API-containing liquid that has wicked along an external surface of the dosing head. The controller can then generate an alert if desired.

Accordingly, as described above, the wash solution can dislodge residual API from the dosing head and deliver the dislodged API to the substrate while the initial volume is being delivered, and after the initial volume has been delivered. It has been found that removal of the adhered residual API from the dosing head 46 can reduce or prevent API clogs from forming at the outlet of the dosing head 46. It can further be desirable to deliver wash fluid to the dosing head 46, and in particular to the external surface of the dosing head 46, when the system 20 is in the idle mode. In particular, a refuse container can be aligned with the dosing head 46, such that wash fluid delivered to the dosing head 46 that flows off of the dosing head 46 travels to the refuse container. The wash fluid can be delivered to the dosing head 46 to maintain a desired level of cleanliness of the dosing head 46, thereby preventing or reducing API clogging of the dosing head 46 while the system 20 is in the idle condition. In one example, the wash fluid can be delivered when it is observed that API has wicked along the dosing head 46. Alternatively, the wash fluid can be delivered upon expiration of a predetermined length of time since the wash fluid was previously delivered to the dosing head 46. It is recognized that the was fluid may have delivered some API from the free terminal end or *meniscus* of the wash fluid in the dosing head. Therefore, when it is time to discontinue the idle mode and begin delivering the API-containing liquid to a new substrate, it may be desirable to operate the pump 49 in the forward direction to deliver a sacrificial volume of the API-containing liquid proximate to the free terminal end to the refuse container. After the sacrificial volume has been emitted from the dosing head 46, a substrate 23 can be aligned with the dosing head 46, and the system 20 can deliver the predetermined volume of API-containing liquid to the substrate in the manner described above. The system can thus position the *meniscus* of the API-containing liquid in the output line 89 at the substantially same position when beginning a dosing operation for all substrates.

With continuing reference to FIG. 9, the system 20 can include either or both of at least one pressure sensor 162 and at least one temperature sensor 164 that are each in communication with the controller 57, for instance over the bus 115. Each of the pressure sensor 162 and the temperature sensor 164 can provide pressure and temperature data, respectively, of the output line 89 and thus of the API-containing liquid in the outlet line 89, to the controller 57. For instance, at least one pressure sensor 162 and at least one temperature sensor 164 can be positioned in the second conduit 53 at a location between the pump 49 and the dosing head 46. The temperature sensor 164 can be located at substantially the same location as the pressure sensor, so that the temperature of the API-containing liquid in the second conduit 53 can be measured at approximately the same location that the pressure of the API-containing liquid in the second conduit 53 is measured. The pressure and temperature sensors can measure the pressure and temperature, respectively, of the API-containing liquid in the second conduit can be measured constantly in real time, or continuously at predetermined intervals in real time as desired.

In one example, the at least one pressure sensor 162 can be a static pressure sensor. In another example, the at least one pressure sensor 162 can be a dynamic pressure sensor. In still other examples, the pressure sensor 162 can be configured to measure both static pressure and dynamic pressure. In one example, the pressure sensor 162 can be configured as a pitot tube. The temperature sensor 164 can be configured as a thermocouple, or can measure the temperature of the API-containing liquid using interferometry. Either or both of the at least one pressure sensor 162 and the temperature sensor 164 can be conventionally fabricated, or can be MEMS devices as desired.

In some examples, the temperature sensor 164 can extend into the second conduit 53 to measure the temperature of the API-containing liquid directly. In other examples, the at least one temperature sensor 164 can measure the temperature of the second conduit 53, which corresponds to the temperature of the API-containing liquid. Accordingly, the temperatures sensed by the at least one temperature sensor 164 that measures the temperature of the conduit 53 might not be equal to the temperature of the API-containing liquid in some circumstances. However, it has been found that a change of the temperature of the second conduit 53 substantially equals to a change of the temperature of the API-containing liquid. Therefore, changes in temperature of the API-containing liquid can be determined either by subtracting temperature measurements of the API-containing liquid directly, or by subtracting temperature measurements of the API-containing liquid indirectly by subtracting temperature measurements of the second conduit 53. Changes in temperature of the API-containing liquid that are determined by subtracting temperature measurements of the API-containing liquid directly can be referred to as direct temperature changes of the API-containing liquid. Changes in temperature of the API-containing liquid that are determined by subtracting temperature measurements of the second conduit 53 can be referred to as indirect temperature changes of the API-containing liquid. Reference herein to the changes of the temperature of the API-containing liquid include both direct and indirect temperature changes of the API-containing liquid. Further, reference herein to temperature measurements of the API-containing liquid include direct temperature measurements of the API-containing liquid, and indirect temperature measurements of the API-containing liquid that are obtained by measuring temperatures of the second conduit 53.

The at least one pressure sensor 162 can include a first pressure sensor disposed adjacent and downstream of the pump 49. Thus, the pressure of the API-containing liquid 25 can be measured in the second conduit 53 after the liquid has been delivered to the second conduit and before it travels through the flow meter 160. Alternatively, the at least one pressure sensor 162 can be disposed downstream of the flow meter 160. In other examples, the flow meter is not present in the system 20. Alternatively or additionally, the at least one pressure sensor 162 can include a second pressure sensor adjacent the dosing head 46. Thus, the pressure of the API-containing liquid 25 can indicate the pressure of the API-containing liquid when the liquid flows into the dosing head 46. The second pressure sensor 162 can be disposed upstream or downstream of the bubble detector 142 as desired. In this regard, as will be described in more detail below, the pressure sensor 162 can also detect the presence of bubbles in the API-containing liquid 25. Thus, the second pressure sensor 162 can replace the bubble detector 142 if desired. Alternatively, the second pressure sensor 162 and the bubble detector 142 can each be included in the system to provide confirmation upon detection of a bubble.

Figure 16:
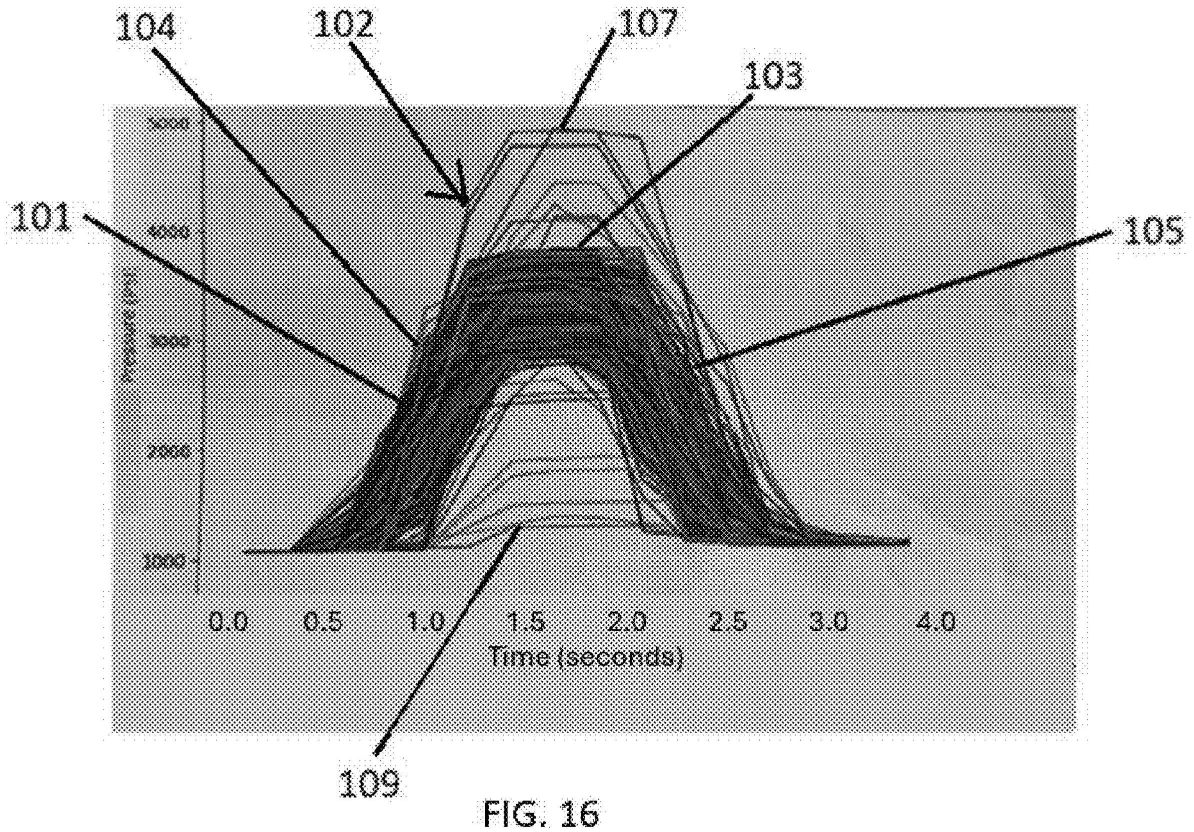
FIG. 16 is graphic showing measured pressure as a function of time during a number of dosing operations.

Referring now also to FIG. 16, measured pressure of the pressure sensor 162 at a respective location in the second conduit 53 is illustrated over a period of time during the dosing operation of a plurality of substrates 23. FIG. 16 illustrates a plurality of pressure profiles 102 including reference pressure profiles 104. In particular, a dosing operation of the system 20 that delivers the predetermined dosage of API in an API-containing liquid to the substrate in the manner described herein can produce a standard dosing profile. The standard reference pressure profile begins at a nominal pressure, produces an initial increase 101 in pressure followed by a substantially horizontal plateau 103 followed by a decrease 105 in pressure. The increase in pressure can be produced when the pump is initiated in the forward direction, which introduces API-containing liquid into the second conduit 53 in the manner described above. Once the pressure in the output line 89 builds to a point where API-containing liquid is driven out of the dosing head 46 at the same rate that the API-containing liquid is delivered to the second conduit 53 from the pump, the pressure curve produces the plateau 103. Finally, when the pump has achieved the predetermined volumetric displacement sufficient to deliver the predetermined dosage of API to the substrate 23, the operation of the pump is discontinued. However, because the output line 89 is pressurized, the API-containing liquid continues to travel out of the dosing head to the substrate, which causes the pressure in the output line 89 to decrease, thereby producing the decrease in pressure 105. A return of the pressure to the nominal pressure can indicate that the initial volume of API-containing liquid has been delivered to the substrate 23, and the washing sequence can be performed to deliver the residual API to the substrate in the manner described above.

The pressure profiles 102 of FIG. 16 can further include deviated pressure profiles that are deviated from the reference profiles 104, and thus indicate a potential defect in the dosing operation. The defect can include a change in concentration and/or viscosity of the API, a leak in the output line 89, a clog in the output line 89, and bubbles in the API-containing liquid in the output line 89. Thus, the controller is configured to use pressure thresholds and/or threshold changes of pressure and/or differences with respect to signature fingerprints for the API-containing liquid, such as the reference profiles 104, to identify an indication of the defect. During operation of each substrate, the pressure levels as sensed by each pressure sensor 162 can be measured over the duration of the dosing operation of the substrate. The measured pressure levels can be compared to the pressure levels of the reference pressure profiles 102 to validate the dosing operation of the substrate, or to determine if a defect exists. For instance, an increase of concentration, and thus viscosity, of the API can cause the measured pressure to increase. A decrease of concentration, and thus viscosity, of the API can cause the measured pressure to decrease. A leak in the output line 89 can cause the measured pressure to decrease. A clog in the output line 89 can cause the measured pressure to increase. It should therefore be appreciated that reference herein to a pressure increase or a pressure decrease that indicates a defect when dosing an API-containing liquid can be identified with respect to a reference pressure profile of that API-containing liquid.

Thus, for a given API, the measured pressure levels can be plotted to define a pressure profile over time, and the pressure profile can be compared to the reference pressure profile of that API. For instance, the plot of pressure as a function of time of a dosing operation can be compared to the plot of the reference pressure profile. Alternatively or additionally, the difference between the measured pressure for the dosing operation prior to dosing and the pressure level of the plateau can be compared to that of the reference pressure profile. Alternatively or additionally, the slope and/or length of the initial increase in pressure 101 can be compared. Alternatively or additionally, the slope and/or length of decrease in pressure 105 can be compared. Thus, when the API-containing liquid is delivered to the substrate 23, the controller 57 can determine, based on the measured pressure in the second conduit 53 and the known reference pressure profile of the API-containing liquid, if a defect exists in the system 20, such as a change in concentration and/or viscosity, a leak in the output line 89, a clog in the output line 89, and bubbles in the output line 89. If a difference between the measured pressure levels and the corresponding pressure levels of the reference pressure is greater than a predetermined threshold, then the controller 57 can enter an alarm condition and output one or more indicated defects to the user. The threshold can be any percentage deviation as desired, wherein the deviation causes a dosage of API to be delivered that is outside a predetermined accuracy range with respect to the predetermined target dosage. If a plurality of reference pressure profiles exist, then the threshold can be with respect to an averaged reference pressure profile of the plurality of reference pressure profiles.

The reference pressure profile can be determined for a given API-containing liquid by measuring the pressure as a function of time as the API-containing liquid is delivered to the substrate or a plurality of substrates. The absence of potential defects in the output line 89 can all be verified in order to validate the reference pressure profile. For instance, the concentration of API in the API-containing liquid can be independently measured and verified by a UV-Vis device and/or an HPLC device as described herein. A leak can be determined in the line by closing a gate valve adjacent the dosing head 46, and subsequently inducing a positive pressure in the line to determine if any of the API-containing liquid leaks from the output line 89, or a vacuum in the line to determine whether the output line 89 can sustain the vacuum. Bubbles can be detecting using the bubble detector 142 as described above. A clog in the output line 89 can be identified by a sizable and easily identifiable increase in pressure that continues to increase during operation of the system 20. During operation, when none of the defects are found to exist, one or more dosing operations can generate a corresponding one or more reference pressure profiles based on the pressure measured during the dosing operation.

Thus, the system 20, and in particular the controller 57, can determine at least one pressure characteristic such as a plurality of pressure characteristics of either or both of the second conduit 53 and the API-containing liquid based at least in part on the pressure measured by the at least one pressure sensor 62 during a dosing operation. In one example, at least one pressure characteristic can be determined by the controller 57 based on the measured pressure alone. In one example, at least one pressure characteristic can be determined by the controller 57 based on each of the measured pressure of the API-containing liquid and the measured temperature of either or both of the API-containing liquid and the second conduit 53, it being appreciated that the temperature of the API-containing liquid can be substantially equal to the temperature of the second conduit 53. Thus, the at least one pressure characteristic can be determined based on the measured pressure, the measured temperature, or both, of the API-containing liquid.

In one example, the at least one pressure characteristic can include a concentration of the API in the API-containing liquid. In this regard, it is recognized that the respective slopes, lengths, amplitudes, shapes, and sizes of each of the increase 101, the plateau 103, and the decrease 105, as well as the area under the curve defined by the increase 101, the plateau 103, and the decrease 105 can be compared to previous dosing operations to validate a given dosing operation. In some examples, an increase 107 in the measured pressure with respect to the standard dosing profile as sensed by at least one pressure sensor can be detected. The increase in pressure can indicate an increase of concentration of API in the API-containing liquid, which also increases the viscosity of the API-containing liquid. In some examples, a decrease 109 in the measured pressure with respect to the standard dosing profile as sensed by at least one pressure sensor can be detected. For instance, a decrease in pressure with respect to the standard dosing profile can indicate a decrease of concentration of API in the API-containing liquid, which also decreases the viscosity of the API-containing liquid.

In other examples, the pressure characteristic can include a clog in the output line 89. The clog can be caused for instance, by a quantity of API that amasses in the conduit or in the dosing head 46 in the manner described above. For instance, evaporation of the liquid carrier in the second conduit 53 can cause the API to crust in the conduit 53, which can cause the clog. An increase in the measured pressure without a subsequent decrease in pressure can indicate the presence of a clog. The increase in the measured pressure can occur as gradually or as abruptly as the formation and severity of the clog in the second conduit. While such an increase in measured pressure can also indicate other conditions, the controller 57 can provide an output to the user who can then investigate the second conduit for a potential clog. For instance, in response to the increase in measured pressure, the system 20 can enter the idle mode, and the clog can be removed in accordance with any suitable method, such as the methods described herein. A clog in the output line 89 can be indicated by an increase in measured pressure, for instance when the increase in pressure is not due to an increase in concentration. In other examples, the pressure characteristic can include a leak in the output line 89, which can be indicated by a decrease in the measured pressure, for instance when the decrease in pressure is not due to a decrease in concentration.

In another example, the pressure characteristic can include a bubble in the API-containing liquid in the second conduit 53. A decrease in the measured pressure of the API-containing liquid in the second conduit 53, as sensed by the pressure sensor, can indicate the presence of a bubble, it being appreciated that bubbles in liquid lines have a higher pressure than the surrounding liquid. Further, the surrounding liquid, which is defined by the API-containing liquid, can have a decreased pressure. Therefore, a decrease in the measured pressure to a decreased level with an immediate momentary spike in the measured pressure that subsequently returns to the decreased level can indicate the presence of a gaseous bubble in the API-containing liquid in the second conduit 53. If a degasser 124 is disposed between first and second pressure sensors 62 in the second conduit 53, and the first pressure sensor indicates the presence of a bubble, and the second pressure sensor 62 does not indicate the presence of a bubble, the controller can conclude that the bubble was eliminated. If a degasser is not present, and the measured pressure indicates one or more bubbles in the API-containing liquid, the decision can be made to enter idle mode and deliver the API-containing liquid in the second conduit 53 into the refuse container as described above. In some instances, if a low threshold presence of bubbles is detected, the decision can be made, if desired, to continue delivering the API-containing liquid to the substrate 23.

In another example, a change in measured pressure (for instance, a first measured pressure at a first time being different than a second measured pressure at a second time after the first time) can indicate that a new batch of API-containing liquid has a defect. In particular, and as described above, when the API-containing liquid in the reservoir 26 gets depleted, a new batch of API-containing liquid can be delivered to the reservoir 26. When the at least one pressure sensor 162 indicates a change in pressure in the second conduit following the delivery of a new batch of API-containing liquid delivered from the reservoir 26 to the pump 49, the controller 57 can indicate to the user that the new batch of the API-containing liquid may be defective. In other examples, when the new batch of API-containing liquid has a different formulation than the previous API-containing liquid, a change in the measured pressure of the API-containing liquid can be expected. An unchanged measured pressure and/or temperature can indicate that the new batch of API-containing liquid is performing similarly to the previous batch of API-containing liquid, thereby validating the new batch.

It is further appreciated that a change, such as an increase or a decrease, in the concentration of API in the API-containing liquid can be detected based in-part on the measured pressure. The change of measured pressure indicating a concentration change is more gradual than the change of measured pressure that indicates a bubble. An increase in the measured pressure can indicate an increase of the concentration. Conversely, a decrease in the measured pressure can indicate a decrease of the concentration. However, the present inventors have also recognized that changes in temperature of the API-containing liquid (for instance, a first measured temperature at a first time being different than a second measured temperature at a second time after the first time) can also affect the concentration.

The system 20, and in particular the controller 57, can determine whether a change in the measured pressure that indicates a detected change of the concentration in the output line 89 with respect to the concentration of API in the reservoir 26 is at least in-part due to a temperature change of the API-containing liquid. In this regard, it is recognized that an increase of the temperature of the API containing liquid can cause the liquid carrier to expand and occupy a greater volume, which therefore decreases the concentration of API in the API-containing liquid. Conversely, a decrease of the temperature of the API containing liquid can cause the liquid carrier to contract and occupy a smaller volume, which therefore increases the concentration of API in the API-containing liquid.

However, when a concentration change is due to the measured temperature of the API-containing liquid, then it can be concluded that the API-containing liquid itself does not a defect in the concentration of the API. In such instances, and in some examples in all instances whereby a concentration change is detected, the volume of API-containing liquid to be delivered to the substrate 23 can be correspondingly changed to account for the temperature-induced concentration change. For instance, either or both of a delivery speed of the pump (speed at which the pump 49 delivers API-containing liquid into the conduit 53 thus out the and dosing head 46 to the substrate 23) and a duration of delivery of the pump (duration of which the pump drives volumes of API-containing liquid into the conduit 53 that are thus delivered to the substrate 23) to compensate for the concentration change, and to the dosage of the API that was predetermined prior to the measured pressure changes. Thus, the predetermined number of volume displacements to be performed can be changed from an initial predetermined number of volume displacements of the pump 49 to an adjusted predetermined number of volume displacements of the pump 49. The initial predetermined number of volume displacements can deliver the initial predetermined volume of API-containing liquid to the substrate 23. The adjusted predetermined number of volume displacements can deliver the adjusted predetermined volume of API-containing liquid containing the predetermined dosage of API to the substrate 23.

If the concentration change produces an increased concentration (and in some instances if the concentration change is not temperature induced), the volume of API-containing liquid that is delivered to the substrate 23 can be correspondingly reduced to maintain the substantially predetermined dosage of API that is delivered to the substrate 23. Alternatively or additionally, heat can be added to the API-containing liquid in the second conduit, for instance when the temperature-induced concentration change is due to a decrease of the temperature of the API-containing liquid in the second conduit 53. Heat can also be added to the API-containing liquid in the second conduit when the concentration increase is not temperature induced. Conversely, if the concentration change produces a decreased concentration, the volume of API-containing liquid can be correspondingly increased to substantially maintain the predetermined dosage of API that is delivered to the substrate 23. Alternatively or additionally, heat can be removed from the API-containing liquid in the second conduit 53, for instance when the temperature-induced concentration change is due to an increase of the temperature of the API-containing liquid in the second conduit 53. Heat can also be removed from the second conduit 53 when the concentration decrease is not temperature induced. It is appreciated that the increase or decrease of the temperature of the API-containing liquid in the second conduit can be determined based on the temperature of the API-containing liquid in the second conduit 53 as sensed by the temperature sensor 164. In some examples, a thermal insulation cover can at least partially or fully surround either or both of the reservoir 26, the first conduit 51, and the second conduit 53, to minimize unwanted temperature changes to the API-containing liquid.

During operation, the controller 57 can determine an indicated change of concentration of API in the API-containing liquid in the conduit based on a change in the measured pressure as measured by the at least one pressure sensor. For instance, the controller 57 can determine the indicated change of concentration from a lookup table based on the change in the measured pressure at the measured temperature. In one example, the lookup table can identify concentrations of the API-containing liquid that correspond to different measured pressures at different points in time in the second conduit 53 at the measured temperature, and the difference or differences between the identified concentrations defines the concentration change. Alternatively, the lookup table can identify the indicated change of concentration of the API-containing liquid that correlates to a particular pressure change at the measured temperature. In other examples, the controller 57 can formulaically calculate the indicated change of concentration based on the change of the measured pressure at the measured temperature. As described above, the indicated change of concentration of API in the API-containing liquid may identify an actual concentration change in the API-containing liquid, can be due to a temperature change that affects the concentration, or can be due to both.

Next, the controller 57 can determine whether a temperature-induced concentration change accounts for an entirety of the indicated change of concentration, a portion of the indicated change of concentration, or none of the indicated change of concentration. In particular, it is determined whether the at least one temperature sensor 164 indicates a change of temperature of the API-containing liquid during the timeframe that corresponds to the timeframe measured change of pressure of the API-containing liquid. If a change of temperature of the API-containing liquid is sensed, the controller 57 confirms a temperature-induced concentration change. The temperature-induced concentration change can be subtracted from the indicated change of concentration to arrive at a net concentration change. Based on the net concentration change, the controller 57 can determine if the indicated change of concentration is at least partially due to the change of measured temperature. For instance, the controller 57 can access a lookup table to correlate the temperature induced concentration change based on the measured temperature change. In one example, the lookup table can identify concentrations of the API-containing liquid that correspond to different measured temperatures at the different points in time that correspond to the different measured pressures in the second conduit 53, and the difference or differences between the identified concentrations defines the temperature-induced concentration change. Alternatively, the lookup table can identify a temperature-induced concentration change of the API-containing liquid that correlates to a particular measured temperature change. Alternatively, the controller 57 can formulaically calculate the temperature induced concentration based on the measured temperature change.

The controller 57 determines that the API-containing liquid has undergone a non-temperature induced change of concentration of the API when the temperature-induced concentration change, if it exists, is substantially less than the indicated change of concentration, such that the net concentration change is substantially greater than zero. Therefore, it can be concluded that the API-containing liquid contains a defect that affects the concentration of API in the API-containing liquid. If the temperature-induced concentration change is substantially equal to the indicated change of concentration (i.e., as measured by the at least one pressure sensor 162), then the net concentration is greater than zero, and the controller 57 can conclude that the API-containing liquid has not undergone a non-temperature induced change of concentration of API. The controller 57 can therefore conclude that the API-containing liquid does not have an API concentration defect.

Further, when the concentration change is induced by a temperature change, the controller 57 can change the temperature of the API-containing liquid in the conduit 53 to eliminate the temperature-induced concentration change, which can eliminate a substantial entirety of the concentration change when the concentration change is temperature-induced. For instance, the controller can add heat to the API-containing liquid in the conduit 53 or remove heat from the API-containing liquid or remove heat from the API-containing liquid in the conduit 53 to eliminate the temperature change of the API-containing liquid, thereby eliminating the change of concentration of the API-containing liquid in the conduit 53. Alternatively, the volume of API-containing liquid can be adjusted in the manner described above to deliver the predetermined dosage of API to the substrate 23.

In other examples, the API-containing liquid in the second conduit 53 can be maintained at a controlled substantially constant temperature. Accordingly, when the at least one pressure sensor 162 senses a pressure change that indicates a concentration change of the API-containing liquid, the controller 57 can determine that the concentration change is a non-temperature induced concentration change that is not due to a temperature change of the API-containing liquid in the second conduit 53. It is further recognized that the system 20, and in particular the controller 57, can independently verify a non-temperature induced concentration change of the API in the API-containing issue. For instance, the system 20 can include either or both of a UV-Vis device 170 (such as a spectrometer or other optical imaging device such as an interferometer) and a high-performance liquid chromatography (HPLC) that can each determine the concentration of API in the API-containing liquid, and thus detect a change in the concentration of API in the API-containing liquid.

It is further appreciated that a change, such as an increase or a decrease, in the viscosity of the API-containing liquid can be detected based in-part on the measured pressure. For instance, an increase in the measured pressure can indicate an increase of the viscosity. Conversely, a decrease in the measured pressure can indicate a decrease of the viscosity. However, the present inventors have also recognized that changes in temperature of the API-containing liquid (for instance, a first measured temperature at a first time being different than a second measured temperature at a second time after the first time) can also affect the viscosity. The system 20, and in particular the controller 57, can determine whether a change in the measured pressure that indicates a potential change of the viscosity is, in fact, a change in the viscosity of the API-containing liquid, or whether the potential change of the viscosity is instead due to a temperature change of the API-containing liquid.

However, when the viscosity change is due to the temperature of the API-containing liquid, then it can be concluded that the API-containing liquid itself does not have a viscosity defect that affects the flow of the API-containing liquid in the second conduit. In such instances, heat can be delivered to the API-containing liquid in the second conduit when a viscosity increase is due to a decrease of the temperature of the API-containing liquid in the second conduit 53. Conversely, heat can be removed from the API-containing liquid in the second conduit 53 when the viscosity decrease is due to an increase of the temperature of the API-containing liquid in the second conduit 53. It is appreciated that the increase or decrease of the temperature of the API-containing liquid in the second conduit can be sensed by the temperature sensor 164.

During operation, the controller 57 can determine an indicated change of viscosity of API in the API-containing liquid in the conduit based on a change in the measured pressure as measured by the at least one pressure sensor 162. For instance, the controller 57 can determine the indicated change of viscosity from a lookup table based on the change in the measured pressure. For instance, the controller 57 can determine the indicated change of viscosity from a lookup table based on the change in the measured pressure. In one example, the lookup table can identify viscosities of the API-containing liquid in the second conduit 53 that correspond to different measured pressures at different points in time, and the difference or differences between the identified concentrations defines the viscosity change. Alternatively, the lookup table can identify the indicated concentration change of the API-containing liquid that correlates to a particular measured pressure change. In other examples, the controller 57 can formulaically calculate the indicated change of viscosity based on the change of the measured pressure. As described above, the indicated change of viscosity of the API-containing liquid may identify an actual viscosity change in the API-containing liquid, or can be due to a temperature change that affects the viscosity, or can be both.

Next, the controller 57 can determine whether a temperature-induced viscosity change accounts for an entirety of the indicated change of viscosity, a portion of the indicated change of viscosity, or none of the indicated change of viscosity. In particular, it is determined whether the at least one temperature sensor 164 indicates a change of temperature of the API-containing liquid during the timeframe that corresponds to the measured change of pressure of the API-containing liquid. If a change of temperature of the API-containing liquid is sensed, the controller 57 confirms a temperature-induced viscosity change. The temperature-induced viscosity change can be subtracted from the indicated change of viscosity based on a pressure change as sensed by the pressure sensor to arrive at a net viscosity change. Based on the net viscosity change, the controller 57 can determine if the indicated change of viscosity is at least partially due to the change of measured temperature. For instance, the controller 57 can access a look-up table to correlate the temperature induced viscosity change based on the measured temperature change. In one example, the lookup table can identify viscosities of the API-containing liquid in the second conduit 53 that correspond to different measured temperatures at different points in time, and the difference or differences between the identified viscosities defines the temperature-induced viscosity change. Alternatively, the lookup table can identify a temperature-induced viscosity change of the API-containing liquid that correlates to a particular measured temperature change. Alternatively, the controller 57 can formulaically calculate the temperature induced viscosity change based on the measured temperature change.

The controller 57 determines that the API-containing liquid has undergone a non-temperature induced change of viscosity of the API when the temperature-induced viscosity change, if it exists, is substantially less than the indicated change of viscosity, such that the net viscosity change is substantially greater than zero. Therefore, it can be concluded that either the API-containing liquid contains a defect that affects the viscosity of API in the API-containing liquid, or a clog exists in the second conduit 53. The controller 57 can enter an alarm condition that allows the user to investigate the cause of the viscosity change. If the temperature-induced viscosity change is substantially equal to the indicated change of viscosity (i.e., as measured by the at least one pressure sensor 162), then the net viscosity change is greater than zero, and the controller 57 can conclude that the API-containing liquid has not undergone a non-temperature induced change of viscosity of API. Therefore, the controller can conclude that the API-containing liquid does not have an API viscosity defect.

In other examples, the API-containing liquid in the second conduit 53 can be maintained at a controlled substantially constant temperature. Accordingly, when the at least one pressure sensor 162 senses a pressure change that indicates a viscosity change of the API-containing liquid, the controller 57 can determine that the viscosity change is a non-temperature induced viscosity change that is not due to a temperature change of the API-containing liquid in the second conduit 53. It is further recognized that the system 20, and in particular the controller 57, can independently verify a non-temperature induced viscosity change of the API in the API-containing issue. For instance, the flow meter can provide an indication of whether the flow rate of the API-containing liquid in the second conduit 53 has increased, thereby indicating a decrease of the viscosity of the API-containing liquid in the second conduit 53. Conversely, the flow meter can provide an indication of whether the flow rate of the API-containing liquid in the second conduit 53 has decreased, thereby indicating an increase of the viscosity of the API-containing liquid in the second conduit 53.

It should be appreciated that at least one pressure sensor 162 and at least one temperature sensor 164 can also be positioned in the first conduit 51, if desired. For instance, the pressure sensor 162 can detect a leak in the first conduit 51 as the API-containing liquid travels from the reservoir to the pump 49. The pressure sensor 162 can further detect a leak in the second conduit. The pressure sensor, both alone and in combination with the temperature sensor, can also detect any of the conditions described above with respect to the second conduit 164.

While the system 20 has been described in connection with at least one pressure sensor 162 in the second conduit 53, it should be appreciated that at least one pressure sensor 162 can also be disposed in the first conduit 51. Accordingly, the system 20, and in particular the controller 52, can identify the existence of any of the pressure characteristics in the first conduit 51 as described above with respect to the second conduit 53. For instance, a decrease of the measured pressure in the first conduit 51 without a subsequent increase can indicate a potential leak in the second conduit 51. While such a decrease in measured pressure can also indicate other conditions, the controller 57 can provide an output to the user who can then investigate the integrity of the first conduit 51. The at least one pressure sensor 62 can further detect pressure changes that indicate the presence of one or more bubbles in the API-containing liquid as it flows from the reservoir 26 to the pump 49.

With continuing reference to FIG. 9, and as described above, the system can include at least one temperature sensor 164 that is configured to measure the temperature and/or temperature changes of the API-containing liquid directly or indirectly, in either or both of the first and second conduits 51 and 53. At least one temperature sensor 164 at the first conduit 51 measures temperature of the API-containing liquid between the reservoir 26 and the pump 49. At least one temperature sensor 164 at the second conduit 53 measures temperature of the API-containing liquid between the pump 49 and the dosing head 46.

It is recognized that the controller 57 can determine a temperature characteristic based at least in part on the measured temperature and/or temperature change. In some examples, the controller 57 can determine an indication of a defect. As described above with respect to the at least one pressure sensor 162, an indication of a defect based on a temperature change as sensed by the at least one temperature sensor 164 may not necessarily prove the existence of the defect, but the controller can enter an alarm condition that allows the user to perform diagnostics related to the indicated defect, and perform repairs if necessary. In some examples, the controller 57 can change the delivery speed at which the API-containing liquid is delivered to the second conduit 53 and/or a delivery duration in which that API-containing liquid is delivered to the second conduit, and thus out the dosing head 46 to the substrate 23. While it is recognized that temperature fluctuations will likely occur over the course of time, and that normal temperature fluctuations will not impact the performance of the system, other larger temperature fluctuations can indicate a defect. Therefore, in some examples, the controller 57 can be programmed to enter an alarm condition upon measurement of a temperature gradient that is greater than a threshold over a specified duration of time.

In one example, the temperature characteristic can include at least one of a faulty pump, a degradation of the API in the API-containing liquid, a clog in the second conduit 53, a density of the API-containing liquid, a viscosity of the API-containing liquid, and a concentration of the API-containing liquid. It is recognized that some of the temperature characteristics, such as the viscosity and the concentration, can also be referred to as pressure characteristics.

The measuring step can be performed at any suitable location of the dosing system 20 as desired to detect any one or more up to all of the temperature characteristics. For instance, temperature of the API-containing liquid can be measured at a first location closer to the pump 49 than the dosing head 46. In one example, the temperature of the API-containing liquid can be measured at a location proximate to the pump, such that measured increases of the temperature of the API-containing liquid indicate that the pump is faulty.

Alternatively or additionally, the measuring step can be performed at a second location closer to the dosing head 46 than the pump 49. In one example, the temperature of the API-containing liquid can be measured at a location proximate to the dosing head 46, such that in increased in measured temperature of the API can indicate one or both of a clog in the output line 89 and an increased in a volume of API-containing liquid that is or will wick along an exterior surface of the dosing head. In this regard, it is recognized that temperature-induced clogs can be more likely to occur in the dosing head 46 or at an interface between the second conduit 53 and the dosing head 46.

In some examples, a temperature-induced expansion of the API-containing liquid in the second conduit 53 can cause either or both of the viscosity of the API-containing liquid and the concentration of API in the API-containing liquid to selectively increase or decrease. For instance, an increase of measured temperature can cause the API-containing liquid to expand in the conduit. The expansion can be calculated based on the coefficient of thermal expansion of the API-containing liquid. It is recognized that expansion of the API-containing liquid can decrease the viscosity of the API-containing liquid. Expansion of the API-containing liquid can also decrease the concentration of API in the API-containing liquid. Conversely, a decrease in measured temperature can indicate either or both of an increase in the viscosity of the API-containing liquid and an increase in the concentration of API in the API-containing liquid. In this regard, the API-containing liquid can be maintained at a temperature that causes the API-containing liquid to have a desired viscosity.

As will be described in more detail below, the system 20 can include one or more analysis stations (which can be online or offline) that can direct light to the API-containing liquid or individual components thereof to determine the concentration of the API in the API-containing liquid to verify whether the change in the concentration has occurred. If the analysis station indicates that the concentration of the API in the API-containing liquid does not correlate to the change of concentration as calculated based on the measured temperature change, the controller 57 can provide an alarm condition that indicates that the API-containing liquid may be defective.

At least one temperature sensor 164 can further be configured to measure the temperature of the API-containing liquid in the first conduit 51. Thus, the at least one temperature sensor 164 can be disposed between the reservoir 26 and the pump 49. The at least one temperature sensor can be configured to measure temperature changes that indicate defects of suitable temperature conditions as described above. In one example, the at least one temperature sensor 164 can be disposed proximate to the pump such that a measured increase of the temperature of the API-containing liquid can indicate that the pump 49 is faulty. Alternatively or additionally, at least one temperature sensor 164 can be positioned proximate to the reservoir. In this regard, it is recognized that a measured temperature increase can indicate degradation of the API in the API-containing liquid. Diagnostics can be performed on the existing batch of API-containing liquid in the reservoir 26, and the existing batch can be replaced by a new batch if the existing batch is found to be defective.

Figure 13:
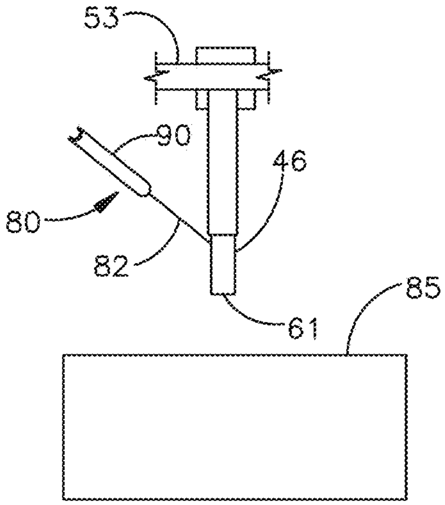
FIG. 13 is a schematic view of a dosing station of the dosing system of FIG. 9, shown configured to deliver API-containing liquid to a refuse container.

Referring now to FIGS. 9 and 13, the present inventors recognize that periods of time will exist when it is desired for the system 20 to enter an idle mode, which allows the API-containing liquid to be emptied from the output line 89. The idle mode can be entered in response to the presence of an idle parameter among a set of idle parameters. In one example, the set of idle parameters can include an expiration of a duration of time (e.g., duration of time since a previous idle mode), or after a predetermined number of substrates 23 have been dosed. Thus, the set of idle parameters can include as preventative maintenance parameters. In other examples, the set of idle parameters can include a sensed condition of the system 20. In one example, the sensed condition can be any condition that is sensed or indicated that can cause an alarm condition. For instance, the sensed condition can be a clog of the API-containing liquid, or the API, in the output line 89. For instance, if the liquid carrier evaporates in the second conduit 53 or in the dosing head 46, the concentration of API in the API-containing liquid can reach a level that causes the API to crust, which can increase the pressure of the API-containing liquid in the system 20 that can be sensed by a pressure sensor in the fluid delivery line 59. The output line 89 can be emptied after the API has crusted, or at time durations designed to prevent the API from crusting.

In another example, the sensed condition can be a sensed presence of particles or gas in the output line 89, or a sensed change in concentration of API in the API-containing liquid. In other examples, the sensed condition can be a detected presence of bubbles in the API-containing liquid as it travels in the output line, and a detected leak in the output line 89. In still other examples, the set of idle parameters can include an identity of the API or API-containing liquid, and thus a determination to change the API-containing liquid to deliver a new API-containing liquid. In this circumstance, it may be desirable to also empty the entire dosing line 59 as well as the output line 89. In another example, the set of idle parameters can include a parameter that may be an identity of the wash fluid 88, and thus a determination to change the wash fluid 88.

When it is desired to empty the output line 89, the substrate 23 can be removed from alignment with the dosing head. It is appreciated that substrates can be brought into and out of alignment with the dosing head by either moving the support surface that supports the substrate 23 to correspondingly move the supported substrate 23, and/or by moving the dosing head 46. Once the substrate 23 has been removed from alignment with the dosing head 46, a refuse container 85 can be brought into alignment with the dosing head 46. Next, the pump 49 can operate to drive API-containing liquid into the second conduit 53, which drives a sacrificial volume of API-containing liquid out of the dosing head 46 and into the refuse container. If desired, a cleaning agent, which can be defined by the wash fluid or any suitable cleaning agent, can be loaded into the pump syringe 126 and driven through the output line 89 and out the dosing head 46 into the refuse container 85, thereby dislodging substantially all API that may have adhered to the output line 89, and delivering the dislodged API to the refuse container 85. It should be appreciated that the duration of the idle mode, and in some examples the sacrificial volume of API-containing liquid or cleaning agent, can be adjusted based on the idle parameter.

Figure 14:
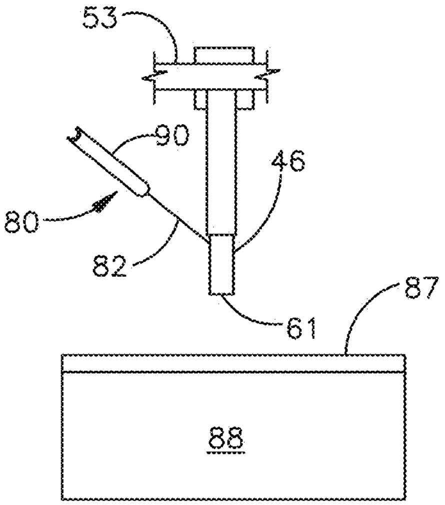
FIG. 14 is a schematic view of a dosing station of the dosing system of FIG. 9, shown configured to submerge a dosing head in a wash bath.

Referring now to FIGS. 9 and 14, in some instances, during the idle mode, it may be desired to at least partially submerge the dosing head 46 in a bath 87 of cleaning agent. The cleaning agent can be a liquid, such as an alcohol, for instance ethanol. In one example, the cleaning agent can be defined by the wash fluid 88 to dislodge any residual API and crusted API from the dosing head 46. Accordingly, when the dosing head 46 is at least partially submerged in the bath 87, the cleaning agent can remove API both from the exterior surface of the dosing head, and from inside the outlet of the dosing head 46. The API in the bath 87 can then be discarded.

The dosing head 46 can be aligned with the bath 87. Subsequently, the dosing head 46 can be submerged in the bath 87 for any time duration as desired. It is envisioned that the API can be dislodged from the dosing head within approximately 1 minute, for instance within approximately 30 seconds, and less than approximately 15 seconds in one example. In one example, the cleaning agent of the bath 87 can be agitated by the dosing head. In other examples, the dosing head 46 can be repeatedly inserted into the bath 87 and removed from the bath 87. The dosing head 46 can be inserted into the bath 87 by bringing the bath 87 up to the dosing head, by bringing the dosing head down to the bath 87, or by detaching the dosing head, and placing the dosing head in the bath 87. Once the submerging step has been completed, the dosing head 46 can then be aligned with a new substrate for delivery of the predetermined volume of the API-containing liquid to the substrate.

With continuing reference to FIG. 9, the system 20 can include at least one analysis station 179 that can be configured to analyze the API-containing liquid 25 and measuring a property of the API in the API-containing liquid. The at least one analysis station 179 can be in communication with the controller 57 over the bus 115. In one example, the analysis station 179 can include an offline analysis station 180. The offline analysis station 180 can include an offline optical sensor. In one example, the offline analysis station 180 can define the HPLC station 177. Thus, in one example, the offline optical sensor can be configured as the HPLC device 181. The HPLC device 181 can be offline from the output line 89, and in particular from the second conduit 53. Thus, the offline analysis station 180, including the HPLC device 181, is configured to receive an analysis volume of the API-containing liquid from the second conduit 53. Once the analysis volume has travelled to offline analysis station 180, the analysis volume remains isolated from the second conduit and unable to flow to the second conduit 53.

The offline analysis station 180 can include an analysis junction that defines an interface with the second conduit 53. The junction can be disposed between the pump 49 and the dosing head 46. In one example, the junction is configured as an analysis valve 182. The analysis valve 182 can be a zero dead volume valve or any suitable alternative valve as desired. The analysis valve 182 can be actuated between a first or closed position and a second or open position. When the analysis valve 182 is in a first or closed position, the API-containing liquid travels continuously and uninterrupted past the offline analysis station 180 toward the dosing head 46. When the analysis valve 182 is in second or open position, the API-containing liquid that is driven to the second conduit 53 toward the dosing head 46 that travels to the analysis valve 182 as the analysis volume is diverted and redirected through the validation valve 148 and to the offline analysis station 180. For instance, the analysis volume can be diverted from the second conduit 53 into an analysis conduit 183 of the offline analysis station 180 that extends from the second conduit at the analysis junction. The analysis volume can then travel through the analysis conduit 183 to the HPLC device 181. Respective analysis volumes can be diverted to the HPLC device 181 at predetermined time intervals, or when the user inputs a command to the controller 57.

The volume of API-containing liquid that is driven into the second conduit 53 can be equal to the volume of API-containing liquid that is driven out of the second conduit 53 when the analysis valve 182 is in the open position, assuming no head space exists in the second conduit 53 and the validation valve is closed. The analysis valve 182 can be a one-way valve, such that when the analysis valve 182 is in the open position, the analysis valve 182 only allows for flow of the API-containing liquid through the analysis valve 182 in a direction from the second conduit 53 to the offline analysis station 180, and prevents the analysis volume of API-containing liquid from flowing through the valve in a direction from the offline analysis station 180 to the second conduit 53.

The present inventors have recognized that the system 20 is devoid of gate valves that modulate the API-containing liquid dispensed to the substrate 23 as in conventional systems. In particular, conventional systems can include gate valves that prevent the API-containing liquid from being emitted from the dosing machine when the gate valves are closed, and allow the API-containing liquid to be emitted from the dosing machine when the gate valves are open. Such conventional dosing machines are susceptible to the formation of clogs defined by the API at the gate valves. In one example, the present system 20 can be devoid of gate valves. Thus, although the system 20 can include the input valve 127, the validation valve 148, and the analysis valve 182, these valves can divert fluid flow but they do not selectively prevent and allow the flow of the API-containing liquid to the substrate 23. Accordingly, the system is less susceptible to API clogs that form at the valves compared to conventional system.

The HPLC device 181 can be configured to measuring at least one property of the API-containing liquid of the analysis volume, and output the at least one measured property to the user. The at least one property of the API-containing liquid can be measured by the HPLC device 181. Further, the at least one property can be measured by another analysis station 179, which can be configured as an inline or offline analysis station that includes an optical sensor configured as a UV-Vis device 170, which can be configured as a spectrometer or interferometer by way of example. The at least one measured property can include one or more up to all of a concentration of the API in the API-containing liquid, a material purity of the API, degradation of the API, and oxidation of the API. In this regard, as described above, if the net viscosity of the API-containing liquid based on analysis of the measured pressure and temperature of the API-containing liquid in the second conduit is greater than zero, the controller 57 can conclude that either the API-containing liquid has a defect, or a clog exists in the output line 89. Because the analysis station 179 is configured to measure the concentration of the API in the API-containing liquid, the analysis station 179 can provide an output that confirms whether the concentration of API in the API-containing liquid has changed, or can confirm that the clog exists if the concentration of API in the API-containing liquid is substantially unchanged. Once the at least one property has been measured by the HPLC device, the analysis volume can be discarded, for instance into a refuse container.

Further, it is appreciated that based on a concentration change of the API in the API-containing liquid as determined by the system 20, and the predetermined volume of the API-containing liquid to be delivered to the substrate prior to determining the concentration change, the controller 57 can determine a total dosage of the API that will be delivered to the substrate. It is recognized that the concentration change will cause the dosage to be different then a predetermined dosage. Therefore, in response to the concentration change, the controller 57 can adjust the volume of API-containing liquid to be delivered to the substrate such that an actual total dosage of API delivered to the substrate substantially equals a predetermined dosage of API. It is recognized that the API-containing liquid can include a single API or multiple APIs. When the API-containing liquid contains multiple APIs, the HPLC device 181 can determine the property of each of the APIs of the API-containing liquid.

The HPLC device 181 contains a high-pressure fluid pump 184 and an elution column 186 which separates molecules carried by the liquid carrier of the API-containing liquid. During operation, the separated molecules travel through the column 186. The molecules exit the column 186 after a retention time, which can be typically on the order of 1-2 minutes for the more compact and simpler molecules, and can be significantly of longer direction, such as up to 30 minutes or more, for larger molecules with complex ligand appendages and folds. This retention-time ordering of the molecules as they exit the column defines a separation of the molecules that is ultimately displayed on the elution plot or chromatogram that is output by the HPLC device 181. The molecules that travel out of the column 186 then travel from the HPLC device 181 to a spectrometer system, such as an offline UV-Vis device **170*b*. As described in more detail below, the UV-Vis device 170*b* of the HPLC station 177 is configured to generate a spectrum that includes a sequence of peaks of the chromatogram, each peak representing optical absorption by a different molecule. While the HPLC station 177 can include the UV-Vis device 170*b* in combination with the HPLC device, it should be appreciated that the HPLC station 177** can alternatively include the HPLC device and any one or more of at least one mass spectrometer such as a plurality of mass spectrometers or mass spectrometer designs.

Reference to chromatogram compendia (such as the Federal Drug Administration (FDA), the United States Pharmacopeia (USP), the International Organization for Standardization (ISO), and the International Council for Harmonisation of Technical Requirements for Pharmaceuticals for Human Use (ICH)) to determine the identify of each molecule in the liquid carrier of the API-containing liquid. Once the identity of each molecule in the liquid carrier has been identified, the concentration of each molecule can be determined. In particular, the sequence of peaks can be compared to known empirically derived data of the API-containing liquid at different API concentrations. Based on this comparison, the concentration of the API can be determined, and compared to the predetermined concentration of API in the API-containing liquid. The volume of API-containing liquid to be delivered to the substrate can be correspondingly increased if the determined concentration is less than the predetermined concentration. Conversely, the volume of API-containing liquid to be delivered to the substrate can be correspondingly decreased if the determined concentration is greater than the predetermined concentration.

The identity of each of the molecules and concentration of the API indicated by the peaks output by the UV-Vis device **170*b* can thus calibrate a UV-Vis device 170*a* that is inline with the output line 89. As is described in more detail below, the inline UV-Vis device 170*a* is configured to generate a spectrum that includes a sequence of peaks that indicate the optical absorption of the molecules in the API-containing liquid. The peaks can be compared to the peaks output by the offline UV-Vis device 170*b* to determine whether the concentration has changed. API-containing liquid can be directed to the HPLC station 177 in the manner described above when the peaks output by the inline UV-Vis device 170*a* differs from the peaks output by the offline UV-Vis device 170*b*. One example of a suitable UV-Vis device 170*a*** is commercially available from Ocean Optics, Inc. having a principal place of business in Orlando, FL.

The UV-Vis devices 170 will now be described in more detail with continuing reference to FIG. 9. In particular, the at least one analysis station 179 can further include an inline analysis station 185. The inline analysis station 185 can include an inline optical sensor. In one example, the optical sensor can be configured as a UV-Vis (ultraviolet-visible) spectrometer or interferometer, which can also be referred to herein as a UV-Vis device 170. Reference to the inline optical sensor can refer to one or more up to all of a spectrometer, an interferometer, and an optical refractometer. The UV-Vis device 170 can be include either or both of an inline UV-Vis device **170*a* and an off-line UV-Vis device 170*b*. The off-line UV-Vis device 170*b* can be included in the HPLC station 177 that also includes the HPLC 181**.

When the UV-Vis device 170 is an inline UV-Vis device 170*a*, the API-containing liquid passes through the UV-Vis device 170*a* as it travels in the second conduit 53.

Figure 15:
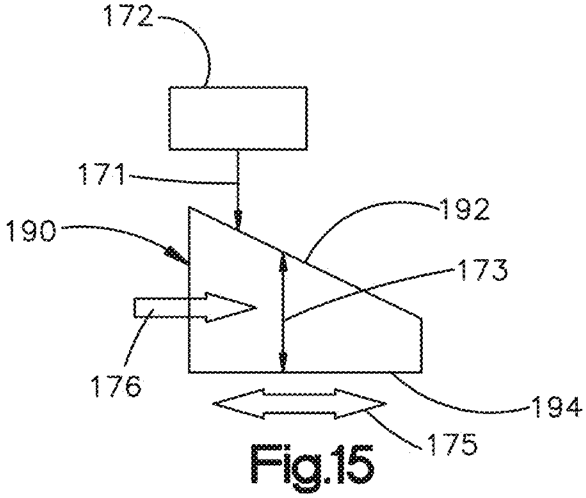
FIG. 15 is a schematic view of a flow cell of a UV-Vis device in one example.

Referring also to FIG. 15, the UV-Vis device 170 can include an optically transparent flow cell 190 (see FIG. 15) that is inline with the second conduit 53 and can be considered to be part of the output line 89. Thus, the UV-Vis device 170 can direct a light beam 171 from a light source 172, through the flow cell 190 along a thickness direction 173 of the flow cell, and through the API-containing liquid as it travels through the flow cell to a reflector, where the light reflects and travels to a detector in the usual manner. The light beam can be can be a visible light beam or an ultraviolet light beam as desired. While the system 20 can include an optical absorption spectrometer as described herein, it is envisioned that the system can alternatively include a vibrational spectrometer configured for infrared spectroscopy or Fourier transform infrared spectroscopy (FTIR) or Raman spectroscopy to sense molecular vibration of the molecules of the API-containing liquid flowing through the vibrational spectrometer, and concentration changes of API in the API-containing liquid can be determined based on sensed changes of molecular vibration.

The thickness of the flow cell 190 through which the light source 172 travels flow cell 190 can be adjustable to match the fluid properties of the API-containing liquid traveling through the flow cell 190 in the forward direction 176. In this regard, it is recognized that darker liquids have a higher absorbance than lighter liquids, and absorb more light from the light source 172 than lighter liquids. Accordingly, it can be desired to direct light from the light source 172 through a lesser path length of the liquid when the liquid is darker in color, and through a greater path length of the liquid when the liquid is lighter in color. Accordingly, the flow cell 190 can have regions having different path lengths defined by the thickness direction 173 of the flow cell 190. The path lengths can extend from an optically transparent upper wall 192 to an optically transparent lower wall 194 that is opposite the upper wall 192 along the thickness direction 173. The light beam 171 travels through the flow cell 190 along the path length through the upper wall 192 to the lower wall 194.

As the liquid travels through the flow cell 190, the position of the flow cell 190 can be adjusted forward and backward in an adjustment direction 175. When the API-containing liquid has a darker color, the flow cell 190 can be adjusted to a position whereby the light beam 171 travels through a region of the flow cell having a shorter path length. When the liquid traveling through the flow cell is lighter in color, the position of the flow cell can be adjusted so that the light from the light source 172 travels through a region of the flow cell having a longer path length. In one example, the flow cell 190 can be wedge shaped so as to accommodate liquids of substantially all colors.

For instance, a distance from the upper wall 192 to the lower wall 194 can define the path length of the flow cell 190 along the thickness direction. The path length can be adjustable depending on the color of the liquid traveling through the flow cell. The adjustment direction 175 can be parallel with the flow direction of the API-containing liquid, and perpendicular to the thickness direction. Thus, as the flow cell is moved in an expansion direction along the adjustment direction 175, progressively greater thicknesses of the flow cell 190 become aligned with the light from the light source 172, thereby increasing the optical path length through the API-containing liquid in the flow cell 190. Accordingly, when the API-containing liquid flows through the light beam 171, the flow cell 190 can be moved in the expansion direction along the adjustment direction 175 when the API-containing liquid is lighter in color. Conversely, as the flow cell is moved in a second direction that is opposite the expansion direction, progressively smaller depths of the flow cell 190 become aligned with the light beam 171, thereby decreasing the optical path length through the API-containing liquid in the flow cell 190. Accordingly, when the API-containing liquid flows through the light source, the flow cell 190 can be moved in the second direction when the API-containing liquid is darker in color. The adjustable position of the flow cell 190 causes light emitted from the light source 172 to travel through a correspondingly adjustable optical path length through the API-containing liquid.

The UV-Vis device 170 can output a spectrum identifying the absorption of light at different wavelengths that correspond to each of the molecules carried by the liquid carrier of the API-containing liquid. In this regard, the known molecules of the API-containing liquid can be identified on the spectrum based on their known wavelengths. Further, unknown molecules identified on the spectrum at wavelengths unassociated with the API can indicate the presence of unwanted contaminants in the API-containing liquid.

It is further appreciated that because the inline UV-Vis device 170*a* is disposed upstream of the HPLC device 181, the HPLC device 181 can analyze the same API-containing liquid that was previously analyzed by the UV-Vis device 170*a*. After the API-containing liquid is analyzed by the inline UV-Vis device 170*a*, a portion of the API-containing liquid subject to UV-Vis analysis can be subsequently diverted to the HPLC station 177 as the analysis volume of the API-containing liquid. The HPLC station 177 can include the HPLC device 181 that separates the molecules of the API in the API-containing liquid, and the offline UV-Vis device 171*b* that can output optical absorption peaks of each molecule of the API-containing liquid that was separated by HPLC device 181. It is appreciated that the API-containing liquid delivered to the substrate 23 is part of a batch of API-containing liquid, and the same batch flows through the UV-Vis device 170*a*, and defines the analysis volume that is diverted to the HPLC device 181. Further, each of the UV-Vis device 170 and the HPLC device 181 can be configured to detect a presence of bubbles in the API-containing liquid.

As shown in FIG. 9, the HPLC device 181 can be disposed downstream from the online UV-Vis device 170*a* so that the analysis volume of the API-containing liquid that is diverted to the HPLC has previously flowed through the online UV-Vis device 170*a*. However, not all API-containing liquid that travels through the UV-Vis device 170*a* is diverted to the HPLC station 177. A portion of the diverted analysis volume of the API-containing liquid that has traveled through the HPLC device 181 can further be directed through the offline UV-Vis device 170*b*, and the controller can correlate the molecules identified on the spectrum of the online UV-Vis device 170*a* with the identified molecules as determined by the HPLC station 177 and their known spectral characteristics (such as absorption characteristics) as determined by the offline UV-Vis device 170*b*. Thus, all molecules identified on the spectrum output by the online UV-Vis device 170*a* can be identified.

During operation, a sample of the API-containing liquid in the container and/or tank can be directed into a flow cell of the UV-Vis device. In one example, the UV-Vis device can emit UV light and visible light to the flow cell to measure the wavelengths at which the light is absorbed by the molecules of the sample disposed in the flow cell. The UV-Vis device can output a spectrum that shows wavelengths at which the light is absorbed. Based on known absorption wavelengths of the molecules in the API-containing liquid, the molecules of the API-containing liquid can be identified on the spectrum. Further, the concentrations of each of the API molecules of the API-containing liquid can be determined based on the absorption strength at the peak wavelength for each of the molecules. Thus, the concentration of the API in the liquid carrier can be determined at different points in time, such as continuously in real-time, to determine whether the concentration has changed over time. If the absorption peak wavelength of the API is unknown, the output of the HPLC that receives the API-containing liquid can provide an identification of the molecules and their respective absorption wavelengths. Therefore, because the absorption wavelengths associated with each of the API are known, the API can be identified on the output of the UV-Vis device 170, and its concentration can therefore be determined. It is recognized that the concentrations of the APIs can be determined by the HPLC as well, but the UV-Vis device 170*a* can generate outputs continuously in real-time inline with the second conduit 53, whereas the HPLC analysis takes place offline.

The concentration of each molecule of the API-containing liquid can therefore be determined by the online UV-Vis device 170*a* either continuously or intermittently in real-time. When the controller 75 identifies an unknown molecule, the controller 75 can indicate a contaminant and enter the alarm condition. When the controller 75 determines that there has been a change in concentration of the API in the API-containing liquid, the controller 75 can subtract any temperature-induced change of concentration in the manner described above, and determine whether the change of concentration is due to a defective API-containing liquid. The controller 75 can correspondingly adjust the volume of API-containing liquid that is delivered to the substrate as desired, so that the predetermined API dosage that was predetermined prior to the change of concentration is delivered to the substrate 23.

Further, as described above, if the net viscosity of the API-containing liquid based on analysis of the measured pressure and temperature of the API-containing liquid in the second conduit 53 is greater than zero, the controller 57 can conclude that either the API-containing liquid has a defect, or a clog exists in the output line 89. Because the UV-Vis device 170*a* is configured to measure the concentration of the API in the API-containing liquid, controller 57 can either confirm the concentration change, or can indicate that a clog exists if the concentration change is substantially constant. It is appreciated that the spectrometer data associated with each substrate 23 can be saved.

If desired, each substrate or packaging that contains the substrate or substrates can carry a tracking indicia that can be scanned to retrieve the spectrometer data or any other data associated with the API or the API-containing liquid that was delivered to the substrate as described herein. Thus, the tracking indicia can identify the API-containing liquid, the date that the substrate was dosed with the API, and storage instructions for the substrate. The indicia can be a bar code, RFID, or the like, that is scannable by the end user.

The present inventors recognize that the online UV-Vis device 170*a* and the HPLC device 181, alone or in combination with the offline UV-Vis device 170*b* can be used in any suitable system as desired whereby a liquid having a liquid carrier and at least one constituent component, such as a plurality of constituent components, carried by the liquid carrier, are delivered to a target use location. The method can include the step of causing the liquid to flow a main conduit, as opposed to the second conduit 53 described above. The UV-Vis device can measure a concentration of at least one of the constituent components as the liquid flows through the main conduit in the manner described above. A portion of the liquid can be diverted from the main conduit through an analysis conduit to an HPLC as an analysis volume of the liquid, and the HLPC can measure a property of at least one of the constituent components of the analysis volume of liquid using an HPLC in the manner described above. The liquid traveling along the main conduit can deliver the liquid to the target use location. Thus, the liquid delivered to the target use location can be the same liquid that was subjected to the step of measuring the concentration. After the analysis volume of the liquid is analyzed at the HPLC device, the analysis volume of the liquid can be discarded into a refuse container, and is thus prevented from being delivered to the target use location. The UV-Vis device 170*a* can be positioned upstream with respect to the HPLC device 181 as described above. Alternatively, the UV-Vis device 170*a* can be disposed downstream of the HPLC device 181.

While the UV-Vis device 170 has been described with respect to identifying the concentration of the API in the API-containing liquid, and the HPLC device 181 has been described with respect to confirming the identity of the API in the API-containing liquid as well as the concentration of the API in the API-containing liquid, it should be appreciated that either or both of the UV-Vis device 170 and the HPLC device 181 can analyze an API-containing liquid that includes more than one API. With respect to the UV-Vis device 170, when the APIs of the API-containing liquid have different known absorption frequencies that are separately plotted on the output spectrum. The HPLC device 181 can separate the individual molecules of the API-containing liquid, and the output chromatogram can identify each molecule of the APIs that are carried by the liquid carrier as well as the concentrations of each molecule carried by the liquid carrier in the manner described above.

Therefore, when the absorption wavelengths of the APIs are unknown when the API-containing liquid flows through the inline UV-Vis device 170*a*, the HPLC 181 can determine the identities of the APIs and provide the absorption wavelengths associated with each of the APIs. Thus, the respective concentrations of the APIs on future outputs from the UV-Vis device 170*a* can be identified based on the absorption wavelengths identified by the UV-Vis device 170*a*. In this manner, the HPLC 181 can calibrate the UV-Vis device 170*a* so that the UV-Vis device 170*a* can identify the concentration of each of the APIs. In other examples, if the absorption frequencies of the APIs overlap each other on the spectrum and are not individually identifiable, the HPLC output can provide an identification of each of the APIs and their respective concentrations.

While the UV-Vis device 170 and the HPLC 181 can identify the concentration of API based on the absorption wavelengths as described above, in other examples the concentration of API can be identified based on the index of refraction as measured by an optional optical refractometer (not shown).

It should be appreciated that while examples of optical sensors have been described, it should be appreciated that the analysis station 179 can include any suitable alternative optical sensor, which can be inline with the output line 89 or offline from the output line 89 as desired. For instance, in addition to or as alternatives to the visible and ultraviolet spectroscopy (UV-vis device 170), examples of optical sensors can include any one or more up to all of infrared (IR) device, interferometry (either mono or spectral light), microscopy, trajectory imaging, florescence imaging or microscopy, ellipsometry (mono or spectral light), Raman scattering or imaging, and infrared vibrational spectroscopy. Alternatively, the at least one analysis station 179 can be configured as a physical analysis station that measures a physical property of the API-containing liquid and components thereof to identify concentrations of the components of the API-containing liquid. In one example, at least one physical analysis station can be include one or more up to all of a surface tension measurement station that determines surface tension of the API-containing liquid by hanging drop metrology using blunt-tip needles, a gravimetrics station that that receives in-situ gravimetric station of drops or streams of the API-containing liquid in reduced air flow chambers employing microscope slides or cover slips for low-mass sampling, and a viscosity station that measures viscosity of the API-containing liquid using hanging drop metrology, as understood by one having ordinary skill in the art. It is envisioned that the physical analysis station can be offline from the output line 89, but can be inline with the output line 89 if the entire volume of the analyzed API-containing liquid is undisturbed and can be delivered to the substrate 23. In other examples, the system 20 can use IR (or FTIR) spectroscopy or Raman spectroscopy of API-containing liquids having multiple APIs to identify relative quantities of chemical molecules present and to detect degradation thereof as may occur by temperature excursions, light exposure or oxidation over time.

The present system 20 is configured to mass produce substrates dosed with API in any manner described herein. In particular, substrates 23 can be individually and sequentially aligned with the dosing head 46, dosed with substantially the predetermined dosage of API in the manner described above, and removed from alignment with the dosing head 46. The present system 20 is configured to emit a volume of API-containing liquid that travels to the substrate 23 that contains the substantially predetermined dosage of API in less than approximately 15 seconds per substrate 23 on average, such as less than approximately 10 seconds per substrate 23 on average, such as less than approximately 5 seconds per substrate 23 on average, such as less than approximately 3 seconds per substrate on average, including less than approximately 2 seconds per substrate on average, such as approximately 1 second per substrate on average. The system 20 can be configured to dose hundreds or thousands or more of substrates that are sequentially brought into alignment with the dosing head 46. Advantageously, each of the substrates can receive substantially the predetermined dosage of API. For instance, substantially all of the substrates can have respective dosages of API that are within approximately 5% of each other, such as within approximately 3% of each other, such as within approximately 2% of each other, and in one example within approximately 1% of each other. Thus, it should be appreciated that The present system 20 is a robust scalable high-volume manufacturing system that is configured to mass produce substrates dosed with a predetermined quantity of API.

It should be noted that the illustrations and discussions of the embodiments and examples shown in the figures are for exemplary purposes only and should not be construed limiting the disclosure. One skilled in the art will appreciate that the present disclosure contemplates a range of possible modifications of the various aspects, embodiments and examples described herein. Additionally, it should be understood that the concepts described above with the above-described embodiments and examples may be employed alone or in combination with any of the other embodiments and examples described above. It should further be appreciated that the various alternatives described above with respect to one illustrated embodiment can apply to all other embodiments and examples described herein, unless otherwise indicated. Reference is therefore made to the claims.

What is claimed:

1. A method of delivering an active pharmaceutical ingredient (API) to a substrate, the method comprising the steps of:

bringing the substrate into alignment with a dosing station having a conduit that terminates at a dosing head, and a pump in fluid communication with the conduit;

causing the pump to drive an API-containing liquid disposed in the conduit out of the dosing head, wherein the API-containing liquid contains the API and a liquid carrier;

measuring a concentration of the API in the API-containing liquid as the API containing liquid travels to the dosing head wherein the measuring step comprises directing a UV-Vis spectrometer at the API-containing liquid in the conduit; and wherein the measured concentration is based on a light absorption profile of the API determined by the spectrometer.

2. The method of claim 1, wherein the concentration is measured in real time.

3. The method of claim 1, wherein the spectrometer uses any one of UV, visible or infrared wavelengths of light, Fourier transform infrared spectroscopy (FTIR), infrared vibrational spectroscopy, or Raman spectroscopy.

4. The method of claim 1, wherein the API-containing liquid travels through a flow cell, and a light travels through the API-containing liquid along a depth of the flow cell.

5. The method of claim 4, wherein the depth is adjustable.

6. The method of claim 2, wherein the measuring step comprises directing a refractometer at the API-containing liquid in the conduit and determining the concentration based on a refractive index profile of the API-containing liquid.

7. The method of claim 1, wherein the API-containing liquid is defined by a batch of the API-containing liquid, and the API-containing liquid subjected to measurements by the UV-Vis spectrometer and an HPLC is defined by the same batch.

8. The method of claim 1, wherein the liquid is a suspension or an emulsion.

9. The method of claim 8, wherein the liquid carrier is an oil.

10. The method of claim 1, wherein the API-containing liquid comprises a solution.

11. The method of claim 10, wherein the liquid carrier comprises a solvent.

12. The method of claim 11, wherein the solvent is ethanol, ethyl acetate, or water, or an organic fluid including an oil.

13. The method of claim 1, comprising the step of causing the API-containing liquid to flow through the spectrometer and an HPLC to determine the concentration of at least one constituent component of the API-containing liquid.

14. The method of claim 13, wherein the API-containing liquid flows through the spectrometer prior to being diverted to the HPLC.

15. The method of claim 1, comprising the step of diverting the API-containing liquid as an analysis volume of API-containing liquid to an HPLC.

16. The method of claim 1, further comprising identifying a contaminant in an output of the spectrometer.

17. The method of claim 1, further comprising the steps of:

measuring either or both of a temperature and a pressure of the API-containing liquid in the conduit during the step of causing the pump to drive the API-containing liquid; and determining a characteristic based at least in part on the measuring step, wherein the characteristic comprises at least one of a faulty condition of the pump, a degradation of the API, a clog or a leak in the conduit, a change of density of the API-containing liquid, a change of viscosity of the API-containing liquid, and a change of concentration of the API in the API-containing liquid.

18. The method of claim 1, further comprising the step of directing a wash fluid to the dosing head, which removes API that has adhered to the dosing head.

19. The method of claim 18, wherein the API defines a first portion of API that is delivered to the substrate during the delivering step, and a second portion of the API defines the API that is adhered to the dosing head.

20. The method of claim 19, wherein the directing step causes the wash fluid and the second portion of the API to be delivered to the substrate.

21. The method of claim 20, wherein the step of delivering the wash fluid is performed upon completion of the delivery of the first portion of API to the substrate.

22. The method of claim 18, wherein at least a portion of the removed API is disposed in a bolus of API-containing liquid disposed at an outlet of the dosing head.

23. The method of claim 18, further comprising the step of entering an idle mode upon an indication of an idle parameter among a set of idle parameters.

24. The method of claim 23, wherein the idle parameters comprise an identity of the API-containing liquid, duration of time since a prior event of the idle mode, an identity of the wash fluid, and a sensed condition, and a step of delivering the wash fluid is performed during the idle mode.

25. A method of delivering an active pharmaceutical ingredient (API) to a substrate, the method comprising the steps of:

bringing the substrate into alignment with a dosing station having a conduit that terminates at a dosing head, and a pump in fluid communication with the conduit;

causing the pump to drive an API-containing liquid disposed in the conduit out of the dosing head, wherein the API-containing liquid contains the API and a liquid carrier;

measuring a concentration of the API in the API-containing liquid as the API containing liquid travels to the dosing head;

wherein the concentration is measured in real time; and wherein the measuring step comprises directing a refractometer at the API-containing liquid in the conduit and determining the concentration based on a refractive index profile of the API-containing liquid.

26. A method of delivering an active pharmaceutical ingredient (API) to a substrate, the method comprising the steps of:

bringing the substrate into alignment with a dosing station having a conduit that terminates at a dosing head, and a pump in fluid communication with the conduit;

causing the pump to drive an API-containing liquid disposed in the conduit out of the dosing head, wherein the API-containing liquid contains the API and a liquid carrier;

measuring a concentration of the API in the API-containing liquid as the API containing liquid travels to the dosing head; and diverting the API-containing liquid as an analysis volume of API-containing liquid to an HPLC.

27. The method of claim 26, further comprising the steps of:

measuring either or both of a temperature and a pressure of the API-containing liquid in the conduit during the step of causing the pump to drive the API-containing liquid; and determining a characteristic based at least in part on the measuring step, wherein the characteristic comprises at least one of a faulty condition of the pump, a degradation of the API, a clog or a leak in the conduit, a change of density of the API-containing liquid, a change of viscosity of the API-containing liquid, and a change of concentration of the API in the API-containing liquid.

28. A method of delivering an active pharmaceutical ingredient (API) to a substrate, the method comprising the steps of:

bringing the substrate into alignment with a dosing station having a conduit that terminates at a dosing head, and a pump in fluid communication with the conduit;

causing the pump to drive an API-containing liquid disposed in the conduit out of the dosing head, wherein the API-containing liquid contains the API and a liquid carrier;

measuring a concentration of the API in the API-containing liquid as the API containing liquid travels to the dosing head;

directing a wash fluid to the dosing head, which removes API that has adhered to the dosing head; and wherein the API defines a first portion of API that is delivered to the substrate during the delivering step, and a second portion of the API defines the API that is adhered to the dosing head.

29. The method of claim 28, wherein the directing step causes the wash fluid and the second portion of the API to be delivered to the substrate.

30. The method of claim 29, wherein the step of delivering the wash fluid is performed upon completion of the delivery of the first portion of API to the substrate.

* * * * *